(12) United States Patent
Brass et al.

(10) Patent No.: US 10,378,015 B2
(45) Date of Patent: Aug. 13, 2019

(54) TARGETING HEPATITIS B VIRUS (HBV) HOST FACTORS

(71) Applicant: University of Massachusetts, Boston, MA (US)

(72) Inventors: Abraham L. Brass, Newton, MA (US); Miles C. Smith, Oklahoma City, OK (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/712,633

(22) Filed: Sep. 22, 2017

(65) Prior Publication Data

US 2018/0112218 A1   Apr. 26, 2018

Related U.S. Application Data

(63) Continuation of application No. 15/268,119, filed on Sep. 16, 2016, now Pat. No. 9,771,590.

(60) Provisional application No. 62/220,080, filed on Sep. 17, 2015.

(51) Int. Cl.
    C07H 21/02       (2006.01)
    C07H 21/04       (2006.01)
    C12N 15/113      (2010.01)
    C12Q 1/18        (2006.01)

(52) U.S. Cl.
    CPC ........ C12N 15/1131 (2013.01); C12N 15/113 (2013.01); C12Q 1/18 (2013.01); C12N 2310/11 (2013.01); C12N 2310/14 (2013.01); C12N 2310/315 (2013.01); C12N 2310/321 (2013.01); C12N 2310/3231 (2013.01); C12N 2320/12 (2013.01); G01N 2500/04 (2013.01)

(58) Field of Classification Search
    CPC ............................ C12N 15/113; C12N 15/111
    See application file for complete search history.

(56) References Cited

U.S. PATENT DOCUMENTS

2011/0054005 A1*   3/2011   Naito et al. .......... C12N 15/113
2012/0315283 A1*  12/2012   Panigraphy et al. ......................
                                                        C12N 15/113

FOREIGN PATENT DOCUMENTS

JP        0 2014060992 A  *  4/2014  .......... C12N 15/111

OTHER PUBLICATIONS

Handrigan et al. (J. Med. Genet., 2013, 50, 163-173).*
Elbashir et al. (The Embo Journal, vol. 20, No. 23, pp. 6877-6888, 2001).*
Hoffman and Thio, "Clinical implications of HIV and hepatitis B co-infection in Asia and Africa," Lancet Infect Dis, Jun. 2007, 7(6): 402-409.
Sells et al., "Production of hepatitis B virus particles in Hep G2 cells transfected with cloned hepatitis B virus DNA," PNAS, Feb. 1987, 84(4): 1005-1009.
Yan et al., "Sodium taurocholate cotransporting polypeptide is a functional receptor for human hepatitis B and D virus," eLife, 2012, 1:e00049.

* cited by examiner

*Primary Examiner* — Amy H Bowman
(74) *Attorney, Agent, or Firm* — Fish & Richardson P.C.

(57) ABSTRACT

Described herein are methods of identifying host factors that modulate Hepatitis B virus (HBV) replication in mammalian, e.g., human cells, as well as factors identified by those methods, and methods of treating HBV infections by targeting those factors. Zinc finger, CCHC domain containing 14 (ZCCHC14) is an exemplary host factor.

12 Claims, 10 Drawing Sheets
Specification includes a Sequence Listing.

SEQUENCE LISTING

```
<160> NUMBER OF SEQ ID NOS: 40

<210> SEQ ID NO 1
<211> LENGTH: 6932
<212> TYPE: DNA
<213> ORGANISM: Homo sapiens

<400> SEQUENCE: 1
ggcgatgagt tcctgctgct gttcaccatg gcctccaacc acccggcctt cagcttccac      60
cagaagcagg tgctgcgcca ggagctcacg cagatccaga gcagcctgaa cggcggcggg     120
ggccacggcg gcaagggcgc gcccgggccg ggcggcgcgc tgcccacttg cccagcctgc     180
cacaagatca ctccaagaac tgaggcccct gtcagcagtg tcagtaatag tttggagaat     240
gccctgcaca catcagcaca ttccacggag gagtcgctgc ccaagaggcc cttaggaaaa     300
cacagcaaag tgagtgttga aaagatagac ctgaagggat tatcacacac aaaaaatgac     360
agaaatgttg aatgttcctt tgaggtcttg tggtctgatt cttcaataac atcagtaacc     420
aaatcttcct ctgaagtgac ggaatttatt tcaaagctat gtcagctcta tcctgaagag     480
aacttggaga aactcattcc ttgcttagct ggtccggacg cattttatgt ggagcgaaac     540
cacgtggatc tggactcagg cctgaggtac ctggcctcat taccttctca cgtgttgaaa     600
aatgaccatg tcaggaggtt tctcagcact tcctctcccc cacagcagct tcagagtcca     660
agtcctggca atccctccct ttctaaagta ggtaccgtga tgggcgtgtc tggaaggcct     720
gtgtgtggag tggctggtat cccgtcctcg cagagcggag cccagcacca cgggcagcac     780
ccggccggct ccgccgcccc cttgcctcac tgctcccatg cgggcagcgc gggctcagcc     840
ctggcctacc ggacccagat ggacacatca cctgccatcc tcatgccttc cagtctgcag     900
acccctcaga cccaggagca gaatgggatt ctagactggc ttaggaaact gcgtttgcac     960
aagtattacc ccgtctttaa gcagctctcc atggagaagt ttttgagcct tactgaagaa    1020
gatctgaata aatttgagtc tcttaccatg ggggcaaaga agaagctcaa gacccagctg    1080
gagctggaaa aggagaagtc agagagacgg tgcctgaacc cctcggcccc gccgctggtc    1140
accagcagtg gtgtggctcg agtgcccccc accagccacg tcgggcccgt gcagtcgggg    1200
cggggcagcc atgcagcaga gctgcgggtg gaagtggagc agcccatca ccagctgccc    1260 cgggaaggca gttcctcgga gtactccagc tcctcctcca gccccatggg ggtacaggcc    1320
cgggaagaga gctccgacag cgctgaggag aatgacagac gtgtggagat tcacttggag    1380
agctctgaca aggagaagcc ggtgatgctg ctgaatcact tcacttccag ttccgccaga    1440
cccacggccc aggttctccc tgtgcagaat gaggccagct ccaatccatc aggccaccac    1500
cccctgcccc cgcagatgct gagcgcagcc tcacacatca cacccatccg catgctgaat    1560
tccgtgcaca agccggaaag agggagcgcg gacatgaagc cctctcgtc ttctgtgcac    1620 tcacttttgt ctctagaaga aaggaataaa ggatctggac caagaagcag catgaaagtg    1680
gacaagagct ttggcagcgc catgatggac gtgctgcccg cgtccgcacc ccaccagcct    1740
```

-continued

```
gtgcaggtcc tctctgggct ttcggagagc agctccatgt cacccacagt ctcctttggt    1800
cccggacca aagtcgtgca tgcatccacg ctggacaggg tgctgaagac agcacagcaa    1860
ccggccctgg tcgtggagac cagcacggcc gccacgggga cgcccagcac agtcctccac    1920
gccgcccgtc cgcccatcaa actgctgctg tcgtcatctg ttcctgctga ttctgccatt    1980
tctgggcaaa cttcctgtcc taataatgtg caaataagtg tgcccctgc aataataaac    2040
ccccggactc tctgtacac agccaacacc aaagttgcct tttctgcaat gagcagtatg    2100
ccagtgggcc cctgcaggg tggcttctgt gcaaacagca acactgcctc tcccagcagc    2160
cacccctcca cgtcctttgc caacatggcc acgttgccca gctgcccagc ccccagctcc    2220
agcccggcgc tgtcctccgt ccctgaaagc agtttctata gcagcagtgg cggtggcggc    2280
tccacaggaa acattcctgc ctcgaatccg aaccaccacc accaccacca ccatcagcag    2340
ccccggcac ccccgcagcc cgccccaccc cgccaggct gcattgtgtg cacgtcctgt    2400
ggctgcagcg gcagctgcgg ctcgagtggc ctgactgtca gctacgccaa ctacttccag    2460
cacccgttct ccggtccgtc cgtgttcacc ttcccttct tgcccttcag tcccatgtgc    2520
agcagcggct acgtcagcgc ccagcagtac ggcggcggct ccaccttccc cgtcgtgcac    2580
gccccttaca gcagcagcgg gaccccagac cctgtcctga gtgggcagtc cacgtttgcc    2640
gtgccaccca tgcagaactt catggcaggg acagcagggg tgtaccagac ccaaggactg    2700
gtgggcagta gcaatggttc cagtcacaaa aagagcggga acctatcttg ttacaactgc    2760
ggggccactg gtcaccgcgc ccaggactgc aaacagccgt ccatggactt caaccggcca    2820
ggtacttta ggttgaaata cgcccctcca gcagaaagtc tggactccac agattgatat    2880
tttctctgg caacagaacg ttattaagcc atggagacat aaggaaaatt aaatacaaaa    2940
ctgagaagtc tagttgctgt tgagcttaat cttttaatc caaaggtgct ttacttttcc    3000
tagactggat agaaaatcta gcgtagaagt gcatcaaact cgatttattg ccaaaaccct    3060
agattggagc ttggtgtcag aactcgccta gtgggcatct ctgtggctgg tgagatcggc    3120
cacctccact tttggttgca gtgcagagac gccatgtctc ccgaagagca ttgccatcac    3180
tggccctcct aggctcacac gtcaattcca gggcagctac acgtggtctg aatcgagaac    3240
cgagcttgga gttctccaag tggagttcca cccgccggac tcctgacacc ctgggctag    3300
ggaaaatgtc gactttgttt tgttctgttc ctaaagtgat tagcactaat ctctgggatt    3360
tttaaggatt gcactacaga agaatgtacc ctgatgtaaa tctctgcggt tctgggagcc    3420
aaactcctct gagaacagtc agtgcaagag actccaataa tccatattga aagagtcagc    3480
accagcagag gctactcgac ttaggacgca acagaggttt tagtatttcc ttcctcctc    3540
caagcacttg tagcagtttc aggttttaa tttttttctg caaataaatc taaactacgt    3600
tattaaatag aaatagttta ctcgcaacaa cttaatttct aagggtccaa gtcccagaga    3660
atccatagtc gtcaaagctt tgagagtatc tttcttccca gccagtcagt ggctttgagc    3720
cctatcttcc actacaaatg acctctcgag ggggacggc gacagcgcgg ctctgtgagt    3780
ggctgtgagg atgctgcacg tcctcagcag agtttgcaag ttgctttatc tcccacgggc    3840
tccccaagaa cctccaaccc cgaggcttat cgctagcgga ttcacacctg agacagacat    3900
ttcaacaatg atacagtcct gtcatttatc agcaaaagat tgggaatttt ctcctgtcaa    3960
cttcttttgt attaggctgt gtattgatag ttaattccgt taaaaattac ttggaaaaca    4020
gtgggaagtg gtaggactct ggaagaggcc acacacccga gagctgcgag atctgtgcaa    4080
```

```
gtctggtttt ggttaggtag taataaaagt cctcactgta gatctctaaa tttcaaccca    4140
cggaaatgaa agccttttgt ctgaaattta cggacttaaa tcttcaaggt taaagggaat    4200
tttctgctca aataatactc ttatcgaaaa tgctaaagtc ttcaatgtta aaatactgat    4260
tggtaaaatc ttgcagttgg gattttgcag ttggatattt attttaaaaa aaattataat    4320
attcagacta ttcttaaaat gggacaatca gcctcatgaa aaattgatgt aaatcagaag    4380 aatacccctag aatgaggcct tgtgatgtga gcgttcaatt tgaagagcag ttcctaactt    4440
catagaaact aaagcagaaa gttgttacat ttttttttatg acaggctttt agtagaattt    4500 tttagttttta ttttagttga attttatttc tatgcaatgc agaattaaca gacctcttct    4560
cctcatggta cacagtatta cagtgttgaa gtaatggtga tgcttattac aacagctatt    4620
taggggaatg ttacgttgat ctcttaaatt gtaaacacta caaaatgtca aaataatgag    4680
aactgacaca actttgcctt aaagagtact agactggacc ttctcatatt acgtttaagg    4740
aagacttaga gtgttcattg atgtttacga ttttaatatt tctgaaggcc attacagtgg    4800
cctggatatg tgctgaaagc caaacttttta aattttttgg ttttttttaag caagaaata    4860 ttttaaataa atcctatttc aacactgaaa ttgttgaaaa ccgtctcata acaaaaggaa    4920
aaaacattgg aattttttgtt ttagtggtca gtataggga atgaaagcgt ctgttgttac    4980
ccacgtaact attttgataa gtattagagg ttaaccttaa atccagcaaa acattaaaac    5040
agaaactttt caacttggag cctgccattc agcgttgagg tagatgagtt ccgacactgt    5100
cacggctgtg ttcccagcag cgaaggcctc tgcggagctg ccagtcgtct tgaacgtgca    5160
tgggcggcgt gtgacatctc cagggaggcc gtccgaagtc gagaatcgtc agctgtaagt    5220
aggagctaca cagcgcagag aaaatggaac cacccatccg tgaggcctct ttccggaggg    5280
agccgcacac ttggacttga gagtttgcca gcagcgagct cggatgcatc tctccaaaag    5340
ccaccaaggt cggcgcgtct gaagagcgtt ttgcggtcat cagacttcct catctgaaaa    5400
cacagaacat actgaccctt tcaagtactt agtcatttttc ctgaaagtgt ggtctgtttc    5460
agaatgctgt ggcaaccagg taggtgtggc actggccatg tgccacgtct ttgcccttttg    5520 tagtctgtca gatattaaag tttctaaccc tgtttttttta atctccaaga atggggaaag    5580
tggaatgtag agatggaagc agaacgtgat gtttggatac aacagctatt taatccttttt    5640 ttattttttta agcaaaacac tcagttttct accttattttt ctaatgttga tttcatggta    5700
atactgacag ttggaagtgt ttaacataaa aactcattgc taaagagcac tgaggaaatg    5760
ggagctagcg cacttgtaat aaaaataaag acaaaatatt ttcttgaatg catatatgtg    5820
attgggtatt ttaaaaacca gtatcatctg tcatctccaa aagattacag gagtcagctt    5880
gttaatacag tagtgttagt aggttctgta tttttaattc agtacttaga attctaggtc    5940
ctttattgcc caaagtcagc acagttagtt tataccacag actctgtctt ggggcacagt    6000 agtgggcgg ggtagtgact ttgcctaaac atcacccagc tggaacagag gctgagcggg    6060
gctttaggca cttgccagat gggaactggg ttgcaccctc cttgctccct gtcatttttct    6120 tgtcactctt cctgcttccc agtgttttat tttatgcctt gctcgttgta catcatgatg    6180
actgatggtc ttcaaggttg tgaggaaagc cgtctccctg cttgactcga ctgctgtccc    6240
agaggagagt cctgtgcgac ctgagcgggg gtggctgcca tttccagcat gcaggtgact    6300
tccaaagaat gagtcaggtg gcactgaaag ccatgggttc tgaagaggcg aatttgttga    6360
aaagtcccaa gggtctgaat gaaagcatct ttaatcaaca ctcaacactc gcaatattct    6420
agaaaaccat atactgtgct ggttgaggcc aaaggttaac attgctccac tgttcaccaa    6480
```

```
ggaaggggc agtggccatc cgccgcggcc tcacgtgcgt tgtaacaagc cctcatcaca      6540
tgtgtgagtc ttacgtgcac aaaaagagaa ggctttggta ctgaaactgg acaccttgtg      6600
tactcgatac cttcacagct tctattggac atattttctt tttaggaatg aaggaaaatt      6660
ctcccatttt tgagccattc ttttgtcaat tctacaaaat tgcatgtaac tttataaata      6720 ttttaaaag atatagtttt gtaaatattt aatattccgc taatttgatt ttgaattgta       6780
aatgtcaagt attctgtttt tggggttttt atgtttatt atactttgtt aaaaaggaca       6840
aattgtacat ttttagaatg tttttatgag taaatttaat gtactgaaaa taaaaatttt      6900
aaaaaaggct gaaaaaaaaa aaaaaaaaaa aa                                    6932

<210> SEQ ID NO 2
<211> LENGTH: 949
<212> TYPE: PRT
<213> ORGANISM: Homo sapiens

<400> SEQUENCE: 2

Met Ala Ser Asn His Pro Ala Phe Ser Phe His Gln Lys Gln Val Leu
1               5                   10                  15

Arg Gln Glu Leu Thr Gln Ile Gln Ser Ser Leu Asn Gly Gly Gly Gly
            20                  25                  30

His Gly Gly Lys Gly Ala Pro Gly Pro Gly Gly Ala Leu Pro Thr Cys
        35                  40                  45

Pro Ala Cys His Lys Ile Thr Pro Arg Thr Glu Ala Pro Val Ser Ser
    50                  55                  60

Val Ser Asn Ser Leu Glu Asn Ala Leu His Thr Ser Ala His Ser Thr
65                  70                  75                  80

Glu Glu Ser Leu Pro Lys Arg Pro Leu Gly Lys His Ser Lys Val Ser
                85                  90                  95

Val Glu Lys Ile Asp Leu Lys Gly Leu Ser His Thr Lys Asn Asp Arg
            100                 105                 110

Asn Val Glu Cys Ser Phe Glu Val Leu Trp Ser Asp Ser Ser Ile Thr
        115                 120                 125

Ser Val Thr Lys Ser Ser Ser Glu Val Thr Glu Phe Ile Ser Lys Leu
    130                 135                 140

Cys Gln Leu Tyr Pro Glu Glu Asn Leu Glu Lys Leu Ile Pro Cys Leu
145                 150                 155                 160

Ala Gly Pro Asp Ala Phe Tyr Val Glu Arg Asn His Val Asp Leu Asp
                165                 170                 175

Ser Gly Leu Arg Tyr Leu Ala Ser Leu Pro Ser His Val Leu Lys Asn
            180                 185                 190

Asp His Val Arg Arg Phe Leu Ser Thr Ser Ser Pro Gln Gln Leu
        195                 200                 205

Gln Ser Pro Ser Pro Gly Asn Pro Ser Leu Ser Lys Val Gly Thr Val
    210                 215                 220

Met Gly Val Ser Gly Arg Pro Val Cys Gly Val Ala Gly Ile Pro Ser
225                 230                 235                 240

Ser Gln Ser Gly Ala Gln His His Gly Gln His Pro Ala Gly Ser Ala
                245                 250                 255

Ala Pro Leu Pro His Cys Ser His Ala Gly Ser Ala Gly Ser Ala Leu
            260                 265                 270

Ala Tyr Arg Thr Gln Met Asp Thr Ser Pro Ala Ile Leu Met Pro Ser
        275                 280                 285
```

-continued

Ser Leu Gln Thr Pro Gln Thr Gln Glu Gln Asn Gly Ile Leu Asp Trp
    290                 295                 300

Leu Arg Lys Leu Arg Leu His Lys Tyr Tyr Pro Val Phe Lys Gln Leu
305                 310                 315                 320

Ser Met Glu Lys Phe Leu Ser Leu Thr Glu Glu Asp Leu Asn Lys Phe
                325                 330                 335

Glu Ser Leu Thr Met Gly Ala Lys Lys Lys Leu Lys Thr Gln Leu Glu
            340                 345                 350

Leu Glu Lys Glu Lys Ser Glu Arg Arg Cys Leu Asn Pro Ser Ala Pro
        355                 360                 365

Pro Leu Val Thr Ser Ser Gly Val Ala Arg Val Pro Pro Thr Ser His
    370                 375                 380

Val Gly Pro Val Gln Ser Gly Arg Gly Ser His Ala Ala Glu Leu Arg
385                 390                 395                 400

Val Glu Val Glu Gln Pro His His Gln Leu Pro Arg Glu Gly Ser Ser
                405                 410                 415

Ser Glu Tyr Ser Ser Ser Ser Ser Pro Met Gly Val Gln Ala Arg
            420                 425                 430

Glu Glu Ser Ser Asp Ser Ala Glu Glu Asn Asp Arg Arg Val Glu Ile
        435                 440                 445

His Leu Glu Ser Ser Asp Lys Glu Lys Pro Val Met Leu Leu Asn His
    450                 455                 460

Phe Thr Ser Ser Ser Ala Arg Pro Thr Ala Gln Val Leu Pro Val Gln
465                 470                 475                 480

Asn Glu Ala Ser Ser Asn Pro Ser Gly His His Pro Leu Pro Pro Gln
                485                 490                 495

Met Leu Ser Ala Ala Ser His Ile Thr Pro Ile Arg Met Leu Asn Ser
            500                 505                 510

Val His Lys Pro Glu Arg Gly Ser Ala Asp Met Lys Leu Leu Ser Ser
        515                 520                 525

Ser Val His Ser Leu Leu Ser Leu Glu Glu Arg Asn Lys Gly Ser Gly
    530                 535                 540

Pro Arg Ser Ser Met Lys Val Asp Lys Ser Phe Gly Ser Ala Met Met
545                 550                 555                 560

Asp Val Leu Pro Ala Ser Ala Pro His Gln Pro Val Gln Val Leu Ser
                565                 570                 575

Gly Leu Ser Glu Ser Ser Ser Met Ser Pro Thr Val Ser Phe Gly Pro
            580                 585                 590

Arg Thr Lys Val Val His Ala Ser Thr Leu Asp Arg Val Leu Lys Thr
        595                 600                 605

Ala Gln Gln Pro Ala Leu Val Val Glu Thr Ser Thr Ala Ala Thr Gly
    610                 615                 620

Thr Pro Ser Thr Val Leu His Ala Ala Arg Pro Pro Ile Lys Leu Leu
625                 630                 635                 640

Leu Ser Ser Ser Val Pro Ala Asp Ser Ala Ile Ser Gly Gln Thr Ser
                645                 650                 655

Cys Pro Asn Asn Val Gln Ile Ser Val Pro Pro Ala Ile Ile Asn Pro
            660                 665                 670

Arg Thr Ala Leu Tyr Thr Ala Asn Thr Lys Val Ala Phe Ser Ala Met
        675                 680                 685

Ser Ser Met Pro Val Gly Pro Leu Gln Gly Gly Phe Cys Ala Asn Ser
    690                 695                 700

Asn Thr Ala Ser Pro Ser Ser His Pro Ser Thr Ser Phe Ala Asn Met

```
705                 710                 715                 720
Ala Thr Leu Pro Ser Cys Pro Ala Pro Ser Ser Ser Pro Ala Leu Ser
                725                 730                 735

Ser Val Pro Glu Ser Ser Phe Tyr Ser Ser Ser Gly Gly Gly Gly Ser
            740                 745                 750

Thr Gly Asn Ile Pro Ala Ser Asn Pro Asn His His His His His
            755                 760                 765

His Gln Gln Pro Pro Ala Pro Pro Gln Pro Ala Pro Pro Pro Gly
    770                 775                 780

Cys Ile Val Cys Thr Ser Cys Gly Cys Ser Gly Ser Cys Gly Ser Ser
785                 790                 795                 800

Gly Leu Thr Val Ser Tyr Ala Asn Tyr Phe Gln His Pro Phe Ser Gly
                805                 810                 815

Pro Ser Val Phe Thr Phe Pro Phe Leu Pro Phe Ser Pro Met Cys Ser
                820                 825                 830

Ser Gly Tyr Val Ser Ala Gln Gln Tyr Gly Gly Gly Ser Thr Phe Pro
            835                 840                 845

Val Val His Ala Pro Tyr Ser Ser Ser Gly Thr Pro Asp Pro Val Leu
    850                 855                 860

Ser Gly Gln Ser Thr Phe Ala Val Pro Pro Met Gln Asn Phe Met Ala
865                 870                 875                 880

Gly Thr Ala Gly Val Tyr Gln Thr Gln Gly Leu Val Gly Ser Ser Asn
                885                 890                 895

Gly Ser Ser His Lys Lys Ser Gly Asn Leu Ser Cys Tyr Asn Cys Gly
                900                 905                 910

Ala Thr Gly His Arg Ala Gln Asp Cys Lys Gln Pro Ser Met Asp Phe
            915                 920                 925

Asn Arg Pro Gly Thr Phe Arg Leu Lys Tyr Ala Pro Pro Ala Glu Ser
    930                 935                 940

Leu Asp Ser Thr Asp
945

<210> SEQ ID NO 3
<211> LENGTH: 3113
<212> TYPE: DNA
<213> ORGANISM: Homo sapiens

<400> SEQUENCE: 3
aggccaacaa cccggccgac ctgggcagcc tcaccaacct gacggacgag gtggtgcgca     60
gcaagctgct ggtgtcgctg cgctgctgg gctcggagca gcgcgaggcg gcgggcgtgc    120
tctaccgcac gctcacgcac atcgactcca tcatccacaa ctacgggctg cagcttaacg    180
agggccgcac gggcgatgag ttcctgctgc tgttcaccat ggcctccaac cacccggcct    240
tcagcttcca ccagaagcag gtgctgcgcc aggagctcac gcagatccag agcagcctga    300
acggcggcgg gggccacggc ggcaagggcg cgccgggcc gggcggcgcg ctgcccactt    360
gcccagcctg ccacaagatc actccaagaa ctgaggcccc tgtcagcagt gtcagtaata    420
gtttggagaa tgcccctgcac acatcagcac attccacgga ggagtcgctg cccaagaggc    480
ccttaggaaa acacagcaaa gtgagtgttg aaaagataga cctgaaggga ttatcacaca    540
caaaaaatga cagaaatgtt gaatgttcct tgaggtctt gtggtctgat tcttcaataa    600
catcagtaac caaatcttcc tctgaagtga cggaatttat ttcaaagcta tgtcagctct    660
atcctgaaga gaacttggag aaactcattc cttgcttagc tggtccggac gcattttatg    720
```

```
tggagcgaaa ccacgtggat ctggactcag gcctgaggta cctggcctca ttaccttctc    780
acgtgttgaa aaatgaccat gtcaggaggt ttctcagcac ttcctctccc ccacagcagc    840
ttcagagtcc aagtcctggc aatccctccc tttctaaagt aggtaccgtg atgggcgtgt    900
ctggaaggcc tgtgtgtgga gtggctggta tcccgtcctc gcagagcgga gcccagcacc    960
acgggcagca cccggccggc tccgccgccc ccttgcctca ctgctcccat gcgggcagcg   1020
cgggctcagc cctggcctac cggacccaga tggacacatc acctgccatc tcatgccttt   1080
ccagtctgca gacccctcag acccaggagc agaatgggat tctagactgg cttaggaaac   1140
tgcgtttgca caagtattac cccgtcttta agcagctctc catggagaag ttttgagcc    1200 ttactgaaga agatctgaat aaatttgagt ctcttaccat gggggcaaag aagaagctca   1260
agacccagct ggagctggaa aaggagaagt cagagagacg gtgcctgaac ccctcggccc   1320
cgccgctggt caccagcagt ggtgtggctc gagtgccccc caccagccac gtcgggcccg   1380
tgcagtcggg gcggggcagc catgcagcag agctgcgggt ggaagtggag cagccccatc   1440
accagctgcc ccgggaaggc agttcctcgg agtactccag ctcctcctcc agccccatgg   1500
gggtacaggc ccgggaagag agctccgaca gcgctgagga gaatgacaga cgtgtggaga   1560
ttcacttgga gagctctgac aaggagaagc cggtgatgct gctgaatcac ttcacttcca   1620
gttccgccag acccacggcc caggttctcc ctgtgcagaa tgaggccagc tccaatccat   1680
caggccacca cccctgccc cgcagatgc tgagcgcagc ctcacacatc acacccatcc    1740
gcatgctgaa ttccgtgcac aagccggaaa gagggagcgc ggacatgaag ctcctctcgt   1800
cttctgtgca ctcactttg tctctagaag aaaggaataa aggatctgga ccaagaagca    1860
gcatgaaagt ggacaagagc tttggcagcg ccatgatgga cgtgctgccc gcgtccgcac   1920
cccaccagcc tgtgcaggtc ctctctgggc tttcggagag cagctccatg tcacccacag   1980
tctcctttgg tccccggacc aaagtcgtgc atgcatccac gctggacagg gtgctgaaga   2040
cagcacagca accggccctg gtcgtggaga ccagcacggc cgccacgggg acgcccagca   2100
cagtcctcca cgccgcccgt ccgcccatca aactgctgct gtcgtcatct gttcctgctg   2160
attctgccat ttctgggcaa acttcctgtc ctaataatgt gcaaataagt gtgccccctg   2220
caataataaa ccccggact gctctgtaca cagccaacac caaagttgcc ttttctgcaa    2280
tgagcagtat gccagtgggc ccctgcagg gtggcttctg tgcaaacagc aacactgcct    2340
ctcccagcag ccaccctcc acgtcctttg ccaacatggc cacgttgccc agctgcccag    2400
cccccagctc cagcccggcg ctgtcctccg tccctgaaag cagtttctat agcagcagtg   2460
gcggtggcgg ctccacagga aacattcctg cctcgaatcc gaaccaccac caccaccacc   2520
accatcagca gccccggca ccccgcagcc ccgcccacc ccgccaggc tgcattgtgt      2580 gcacgtcctg tggctgcagc ggcagctgcg gctcgagtgg cctgactgtc agctacgcca   2640
actacttcca gcaccgttc tccggtccgt ccgtgttcac cttcccttc ttgcccttca     2700 gtcccatgtg cagcagcggc tacgtcagcg cccagcagta cggcggcggc tccaccttcc   2760
ccgtcgtgca cgcccttac agcagcagcg ggaccccaga ccctgtcctg agtgggcagt    2820
ccacgtttgc cgtgccaccc atgcagaact tcatggcagg acagcagggg gtgtaccaga   2880
cccaaggact ggtgggcagt agcaatggtt ccagtcacaa aaagagcggg aacctatctt   2940
gttacaactg cggggccact ggtcaccgcg cccaggactg caaacagccg tccatggact   3000
tcaaccggcc aggtaagcgc gcgccatggc cgcgcccacc aggctcccgc aggaccagtg   3060
cacacaaatg cttggttttt atgaagagta aacttctttc tttgtaaagc aaa          3113
```

<210> SEQ ID NO 4
<211> LENGTH: 961
<212> TYPE: PRT
<213> ORGANISM: Homo sapiens

<400> SEQUENCE: 4

Met Ala Ser Asn His Pro Ala Phe Ser Phe His Gln Lys Gln Val Leu
1               5                   10                  15

Arg Gln Glu Leu Thr Gln Ile Gln Ser Ser Leu Asn Gly Gly Gly Gly
            20                  25                  30

His Gly Gly Lys Gly Ala Pro Gly Pro Gly Gly Ala Leu Pro Thr Cys
        35                  40                  45

Pro Ala Cys His Lys Ile Thr Pro Arg Thr Glu Ala Pro Val Ser Ser
    50                  55                  60

Val Ser Asn Ser Leu Glu Asn Ala Leu His Thr Ser Ala His Ser Thr
65                  70                  75                  80

Glu Glu Ser Leu Pro Lys Arg Pro Leu Gly Lys His Ser Lys Val Ser
                85                  90                  95

Val Glu Lys Ile Asp Leu Lys Gly Leu Ser His Thr Lys Asn Asp Arg
            100                 105                 110

Asn Val Glu Cys Ser Phe Glu Val Leu Trp Ser Asp Ser Ser Ile Thr
        115                 120                 125

Ser Val Thr Lys Ser Ser Ser Glu Val Thr Glu Phe Ile Ser Lys Leu
    130                 135                 140

Cys Gln Leu Tyr Pro Glu Glu Asn Leu Glu Lys Leu Ile Pro Cys Leu
145                 150                 155                 160

Ala Gly Pro Asp Ala Phe Tyr Val Glu Arg Asn His Val Asp Leu Asp
                165                 170                 175

Ser Gly Leu Arg Tyr Leu Ala Ser Leu Pro Ser His Val Leu Lys Asn
            180                 185                 190

Asp His Val Arg Arg Phe Leu Ser Thr Ser Ser Pro Gln Gln Leu
        195                 200                 205

Gln Ser Pro Ser Pro Gly Asn Pro Ser Leu Ser Lys Val Gly Thr Val
    210                 215                 220

Met Gly Val Ser Gly Arg Pro Val Cys Gly Val Ala Gly Ile Pro Ser
225                 230                 235                 240

Ser Gln Ser Gly Ala Gln His His Gly Gln His Pro Ala Gly Ser Ala
                245                 250                 255

Ala Pro Leu Pro His Cys Ser His Ala Gly Ser Ala Gly Ser Ala Leu
            260                 265                 270

Ala Tyr Arg Thr Gln Met Asp Thr Ser Pro Ala Ile Leu Met Pro Ser
        275                 280                 285

Ser Leu Gln Thr Pro Gln Thr Gln Glu Gln Asn Gly Ile Leu Asp Trp
    290                 295                 300

Leu Arg Lys Leu Arg Leu His Lys Tyr Tyr Pro Val Phe Lys Gln Leu
305                 310                 315                 320

Ser Met Glu Lys Phe Leu Ser Leu Thr Glu Glu Asp Leu Asn Lys Phe
                325                 330                 335

Glu Ser Leu Thr Met Gly Ala Lys Lys Lys Leu Lys Thr Gln Leu Glu
            340                 345                 350

Leu Glu Lys Glu Lys Ser Glu Arg Arg Cys Leu Asn Pro Ser Ala Pro
        355                 360                 365

Pro Leu Val Thr Ser Ser Gly Val Ala Arg Val Pro Pro Thr Ser His

```
              370                 375                 380
Val Gly Pro Val Gln Ser Gly Arg Gly Ser His Ala Ala Glu Leu Arg
385                 390                 395                 400

Val Glu Val Glu Gln Pro His His Gln Leu Pro Arg Glu Gly Ser Ser
                405                 410                 415

Ser Glu Tyr Ser Ser Ser Ser Ser Pro Met Gly Val Gln Ala Arg
            420                 425                 430

Glu Glu Ser Ser Asp Ser Ala Glu Glu Asn Asp Arg Arg Val Glu Ile
                435                 440                 445

His Leu Glu Ser Ser Asp Lys Glu Lys Pro Val Met Leu Leu Asn His
            450                 455                 460

Phe Thr Ser Ser Ser Ala Arg Pro Thr Ala Gln Val Leu Pro Val Gln
465                 470                 475                 480

Asn Glu Ala Ser Ser Asn Pro Ser Gly His His Pro Leu Pro Pro Gln
                485                 490                 495

Met Leu Ser Ala Ala Ser His Ile Thr Pro Ile Arg Met Leu Asn Ser
            500                 505                 510

Val His Lys Pro Glu Arg Gly Ser Ala Asp Met Lys Leu Leu Ser Ser
            515                 520                 525

Ser Val His Ser Leu Leu Ser Leu Glu Glu Arg Asn Lys Gly Ser Gly
            530                 535                 540

Pro Arg Ser Ser Met Lys Val Asp Lys Ser Phe Gly Ser Ala Met Met
545                 550                 555                 560

Asp Val Leu Pro Ala Ser Ala Pro His Gln Pro Val Gln Val Leu Ser
                565                 570                 575

Gly Leu Ser Glu Ser Ser Ser Met Ser Pro Thr Val Ser Phe Gly Pro
            580                 585                 590

Arg Thr Lys Val Val His Ala Ser Thr Leu Asp Arg Val Leu Lys Thr
            595                 600                 605

Ala Gln Gln Pro Ala Leu Val Val Glu Thr Ser Thr Ala Ala Thr Gly
            610                 615                 620

Thr Pro Ser Thr Val Leu His Ala Ala Arg Pro Pro Ile Lys Leu Leu
625                 630                 635                 640

Leu Ser Ser Ser Val Pro Ala Asp Ser Ala Ile Ser Gly Gln Thr Ser
                645                 650                 655

Cys Pro Asn Asn Val Gln Ile Ser Val Pro Pro Ala Ile Ile Asn Pro
                660                 665                 670

Arg Thr Ala Leu Tyr Thr Ala Asn Thr Lys Val Ala Phe Ser Ala Met
            675                 680                 685

Ser Ser Met Pro Val Gly Pro Leu Gln Gly Gly Phe Cys Ala Asn Ser
            690                 695                 700

Asn Thr Ala Ser Pro Ser Ser His Pro Ser Thr Ser Phe Ala Asn Met
705                 710                 715                 720

Ala Thr Leu Pro Ser Cys Pro Ala Pro Ser Ser Pro Ala Leu Ser
                725                 730                 735

Ser Val Pro Glu Ser Ser Phe Tyr Ser Ser Ser Gly Gly Gly Ser
            740                 745                 750

Thr Gly Asn Ile Pro Ala Ser Asn Pro Asn His His His His His
            755                 760                 765

His Gln Gln Pro Pro Ala Pro Gln Pro Ala Pro Pro Pro Gly
            770                 775                 780

Cys Ile Val Cys Thr Ser Cys Gly Cys Ser Gly Ser Cys Gly Ser Ser
785                 790                 795                 800
```

Gly Leu Thr Val Ser Tyr Ala Asn Tyr Phe Gln His Pro Phe Ser Gly
            805                 810                 815

Pro Ser Val Phe Thr Phe Pro Phe Leu Pro Phe Ser Pro Met Cys Ser
            820                 825                 830

Ser Gly Tyr Val Ser Ala Gln Gln Tyr Gly Gly Ser Thr Phe Pro
            835                 840                 845

Val Val His Ala Pro Tyr Ser Ser Ser Gly Thr Pro Asp Pro Val Leu
850                     855                 860

Ser Gly Gln Ser Thr Phe Ala Val Pro Pro Met Gln Asn Phe Met Ala
865                 870                 875                 880

Gly Thr Ala Gly Val Tyr Gln Thr Gln Gly Leu Val Gly Ser Ser Asn
            885                 890                 895

Gly Ser Ser His Lys Lys Ser Gly Asn Leu Ser Cys Tyr Asn Cys Gly
            900                 905                 910

Ala Thr Gly His Arg Ala Gln Asp Cys Lys Gln Pro Ser Met Asp Phe
            915                 920                 925

Asn Arg Pro Gly Lys Arg Ala Pro Trp Pro Arg Pro Pro Gly Ser Arg
        930                 935                 940

Arg Thr Ser Ala His Lys Cys Leu Val Phe Met Lys Ser Lys Leu Leu
945                 950                 955                 960

Ser

<210> SEQ ID NO 5
<211> LENGTH: 85800
<212> TYPE: DNA
<213> ORGANISM: Homo sapiens

<400> SEQUENCE: 5

```
aggccaacaa cccggccgac ctgggcagcc tcaccaacct gacggacgag gtggtgcgca      60
gcaagctgct ggtgtcgctg gcgctgctgg gctcggagca gcgcgaggcg gcgggcgtgc     120
tctaccgcac gctcacgcac atcgactcca tcatccacaa ctacgggctg cagcttaacg     180
agggccgcac gggcgatgag ttcctgctgc tgttcaccat ggcctccaac cacccggcct     240
tcagcttcca ccagaagcag gtgctgcgcc aggagctcac gcagatccag agcagcctga     300
acggcggcgg gggccacggc ggcaagggcg cgccccgggcc gggcggcgcg ctgcccactt     360
gcccagcctg ccacaaggtg cgtgcccgcc ccgagctctg ccctgtaccc caagtctgca     420
tccccaactc tgcactccaa gcctccagcc tgcaccgcga cccccgacc cacgcctcca     480
gcctgcactg agagctccca cccaggtctc caacctgcac cacgagcccc cagcccgtat     540
cccaagcccc atcctaagcc tctatgtcgc accccaaatg tgtgccccac ctctccaagc     600
ctccaccgta catcccaagc ctccgccgta catcccaagc ctccgccgta catcccaagc     660
ccccatccta agcccgcact cctcacccta gtctgcact ttaagcccca agaccgcacc     720
gcggccctga gccacacccc tcagtcccct ctgcgtgccc caaagcctcc acacctccgc     780
ctcgcgcccc ttgggcagga gcggctgcag gggccctggg tccgaggatc cgcgggagcg     840
gtgcgggaga cgtccgcggt cagagctcac agtcccaggt gccctccttt cacttagccg     900
gctgcaaacg cgataaggcc tttgtcccct taatggggcc cttgggtgac agataacaca     960
cattgcggcg ccttggtttc cccaaatctg gtatttatta ccagaaaagg aaggagccgt    1020
ggccacgcca gaagccgccg gtgaggtgaa cattgcaagg cgctgggct tcccgtctg     1080
agccgctccc tccacacagg tggaggccct gcttggggcc tgtgtcgctg ggggcctggg    1140
```

```
cgcgggacat ggctgtccgt gtgagctcat ttatggacac gtgcatgctg tatgatgtac    1200
gcgtgtgtcg catgtgggca tgtatatgtg cacacgtgtg tatgaatgtg cacatgcttg    1260
tgaacgttgt gtgtgatcgt ttttaagagc cgggctacct gtaacagaca gaaaaagact    1320
cccagagcct taaatgcccg tgaaacctat ttattggcga cccttagaaa caaaacccag    1380
gctgactttg agtgggaggg caccgatgcc ttaaggaatg ttaggttagg ttaaagatct    1440
ccggtctcca aattgaaccg gaagggcgtc ctggccatcc acttagcgat gtgaactttt    1500
gtctaagtgt ttcagaactg aaaacgcaaa gtgtctgggg ctccagctat tttgaacagc    1560
cccctgcaat ccagtgccaa aattttgctg ccggaagaga ttactttgac ctggtgtgat    1620
gtgtatttag attacaaact gattatttt tggaagggaa taggttgcag tcggaccaa      1680 gtcttgctca gtgtctcttt gcagtgtctt taagctcttt gaagttaaaa ctttgataag    1740
actttgcttt tatgagtggc tgagaacacc gtctggtttg ctaggttttt tatgtgtgtg    1800
tttttaaagc tgtctttcaa tcgtagattg tggcttttct tttttaatgt cttcctgtaa    1860
gaagtggttg tagtacatac atcggttttt ttaaattgat ttttgtgtgt gtgacattta    1920
cctccaagac tatagttttc tttttaagtt cggctcccac cctgtatttc aggctgtgtg    1980
ctgtgcagag ggtcctagga aatgtagttg tttatagtaa tccatgtaag ccttgacatg    2040
ccagcaaatt gtcacctatt catggaatct cagtcattta tggtcagttt catgtgctgt    2100
tactcctttg tgtagattcc acccactaat aatttctatg gctgttgcta cagtaacgtc    2160
atctctttaa ggggattctt aatgtgtgag cacgggtgcc tcactttatg cagacagtgg    2220
tgattattat tttgattggg cagtgagcta aatctagaac aaaaatgtct tttataggag    2280
agcctttctg tgaagcagaa atcccctttga tgagatgaag gggctaatct attcctctct    2340
gctcacccct gcacctcccc cgctacaccc cagtcccaag gccatgggcg ctgaatttac    2400
cagccgtgca accttggcca ggatccttct gcccctcagt gttgtccctg ttgcagtgga    2460
ggggatgtaa cctacctcac aggcttgtgt tgaggattac ataggtaaca tacatgagct    2520
tccagcagag gtgcagtaaa tgctgctttc cctctatgg cctctccggc ttttaacatt     2580
cctttttata gaggtttgct aacttaaagc aaggcatgtt ttatagattg aattatttac    2640
atcttggcta tgagcgttta tgtgttctaa attggttttt gagtagttac ttggagctga    2700
caattttttt gtttcatctt tggaaaactg gaagattctg tgacccttaa tgagaggatt    2760
attataagga gtaaccttgg gctgtcattt ccgtatttca aaacaaccgt ggtttctagt    2820
tttccctaca tccctagtgt cactgctaag ctaatttcag ccccattcat ttaactttcg    2880
tttctgttgc tgcttcaaag ctaaggctga cgttgatgaa ccctttattg cttggagcat    2940
gcaactcaga tgaaatctag catttaagta ttttgctttc ttagtttcta aatctaacgt    3000
ttggtgtatt cctgaaaaag cagccccgtt aaagctgtct gcattctttt gtaagctgtt    3060 gtatttatt ttgaactctt tgagcttaga ctttgtat ttttctttta gagatacaaa        3120
tgtcaatggc ttttttaaatt ctttatccaa tttgaatttt tatttcttgg cctggcaagg    3180
tggcttacgc ctgtagtccc ggaagtttgg gaggtcaagg tgggcagatc gcttgagccc    3240
aggagttcaa caccagcctg gcaacacag caaaaccctg tctctacaaa aaatacaaaa      3300
attagccagg agtggtggca cacttgta gtccctgcta cttgggaggc cgaggtggga       3360
tgattacctg atcccaggag gtagaggctg taggtgaggt atgatcatgc cactgcattc    3420
cagcctgggt gacagagtga gactgtgtct caaaaaattt tttttaaatt tattttaact    3480
gtattttccg aaatagtcat tatttgcaat tccttgtcca aatcctgtgt ttttatttaa    3540
```

-continued

| | | | | |
|---|---|---|---|---|
| aaattcttat | tattctgagg | acttctagag | gtgtaaaagt | gggggagta caaagtagac | 3600 |
| ataccctgtat | tttactttca | gaaagaaaaa | tacttccagt | agccacactg atggtaggct | 3660 |
| gaattagttg | tactctgcct | agtggccggt | aatgctgctg | cttgctgctc ctgcagtcgc | 3720 |
| ctgttccagg | gtgccaactg | tgggggatag | ttggcttaga | ctttccaatg cctatttttac | 3780 |
| gtaaataaaa | gaccatagtt | ttggaaatag | ttaaaataaa | tcctttgcgg cttttttcttt | 3840 |
| gtgtcagtga | taattaatat | gctgtggtat | gtgcacatgc | ttattcttgt ttaaaaaata | 3900 |
| acagctttat | tgaaagagaa | ttcatatact | atatatactt | cacccttta cagtgaagtc | 3960 |
| agtggttttt | agtatagtca | tatagctgtg | caagcacgac | cactgccact gaacgtttcc | 4020 |
| atctccccaa | aaagaaaccc | agtgcctatt | aggagtcgct | ccccattccc cctcccccca | 4080 |
| acccttgacc | accccttttt | gtctctatgg | gtgtcttttt | tggacgttgc atataagggg | 4140 |
| accacacacc | gtgtggccct | tgtgactggg | cttccttcac | tcggtgtcgt gatgtcaggg | 4200 |
| cccgtccatg | ctgtgggtgt | gtcagcactt | cctcctcttt | cgctgccgag tggcgttccc | 4260 |
| ctgtgtgaag | aggccgagct | gtgctcacgc | attcttcagc | gggtggacct tggagttgct | 4320 |
| tcacatgctt | gcttttgtag | acttttgtct | tcatggttaa | taggctcttt gtcttcaccc | 4380 |
| ccgtgcactg | tgcctaacac | ttagcgcatc | ctctgtggac | cgctggcgca cgtgtcggtg | 4440 |
| cggggctgtc | ctgagggctc | ctgttccacc | tggtggattg | ctaggtgccg tgtgcagagc | 4500 |
| tgtgtaggtg | tggcctcagc | cagcctgggg | agctgcagct | ggaggtggca gggaactctg | 4560 |
| tgctgtcagt | acagagcctc | cgggctggtg | catttggtca | gcgacaggta tgggggagca | 4620 |
| gggcctggtg | ggcaggggcg | gggccccgcc | tgagctgcag | ctgtgagggc cctgccgttt | 4680 |
| gtgtttcagc | atcctcaggg | tatggataat | gaactgcttc | atgggctga tttttttaag | 4740 |
| ggggtactaa | aaaaaataac | gttttaaag | ttttggtgc | aggagtgtgg tggggtggtg | 4800 |
| gtcttctttta | ggggtaggtt | ctgtggaaca | gttctggaac | tctctgtggc ttgcattgtg | 4860 |
| agtgcctgag | gataagcact | gtggaaactt | cagatagaca | caaataccgt gaataaacct | 4920 |
| gctgaaaatg | tctgtccaaa | gatcagcaac | agcttttgct | tcgttgcttt tcgtaagctg | 4980 |
| ttgaaaatca | ttgcagttca | gaggtgaaac | atgggatagt | tcatcctctg ttatcaggc | 5040 |
| aaagtataag | tggtttctttt | tggtttctcc | tttagcccta | aactctgggc ctattgcagc | 5100 |
| caagagtcat | ctagcattcc | ataagaacgg | actctctctg | gagcagctgt tgtcactgat | 5160 |
| ggttaaagga | atagctgtga | cctaaaagca | ctgttttgtc | tccatctta acacttgttc | 5220 |
| tcctgggcag | ctgggaaccg | cctggtctat | gaacttgtct | gtgaactaag tcttctggct | 5280 |
| gtctttgtat | acattgcttt | ttttgttgtt | gttgttacat | tacaggagat acaggagata | 5340 |
| atattctaac | acatagtgga | tcttttttta | tttttatttt | tatttttttgg ccagctgcta | 5400 |
| caggtctaaa | acactgtcct | gtttcatagt | aaagtacagt | acatgatacg ggaattgagg | 5460 |
| catacagtca | tgtgctgctt | aaggacacag | atacgttctg | agaaaagcgt cctcagctga | 5520 |
| tcttgttgtg | tgagcaccgc | agagtgcact | tgcacagacc | tgggtggcag aacccgctac | 5580 |
| acctctgggc | cacattgtag | agcctgttgc | tcctcggctg | taaacctgta cagcgtgtta | 5640 |
| ctgtactgaa | taccataggc | agttgtaacc | cagtggtatt | tgtgtatcta aacacagaat | 5700 |
| aggtacagta | aaaatgcatt | attagaatct | tagaggatcc | ctggtccgtg tggtctgtca | 5760 |
| gtggtggaag | catccttatg | cagtgcgtga | ccgtgctggg | atgcagttct gattgctttc | 5820 |
| ttggtggtag | tatttctgtt | gatgccatga | tggagctgca | gtagcactgc catctactgt | 5880 |

-continued

```
gtaatggctt ggattatgtg gtactttaat tactgtcctt tgccctcaca ttaaatgaag    5940
gccatttact ttgacatgag ctagttcaca tttgcctcat taggtgaaca cacatttgag    6000
ttttgctgtt ttctactgtg ttctggagca cagttgtaga aactggaaat tctgtgtcat    6060
atttgggtat gatgagtaat acgatggtat catttgttca agtgcgaaga taactggaga    6120
taggcatctg cgttagtctt gtcactgcag gtgaagcgta ctgtttactt aggctttagt    6180
ttacccattt tctctttagt cctgtaaact tcatctacct tttgaattaa catgcttttc    6240
caacaaatct acatgagtct taaaacttca gagtccagct agtagaatag aatagtaaga    6300
ggtactcgcg ctggggcatc tttgtttgtt gaattgatga cgaagaaatt tttgttatgc    6360
taggaaaaat ttctgcttta gtattctccc ccgcccccca ccttagaggg attagatttt    6420
agaaaaagat tcttcttctt tttttttttt tttttggaaa actgcccgtt ggaacagtag    6480
ttatcttgtt agtttaagta agaagtgtag ctgcaagtta cctaattagg gtacattatt    6540
gaagggcttt tggttttgga ctttagtctt aacatacgca gtttagaaat tagttttagc    6600
aaggtaattt ttttctccag tctctgtaga tgttttatt gtagagagac ctgacacatt    6660
gtagaaacat ttcctgtcaa aggtaaaaag agatcatcca gaactaacaa aataggttaa    6720
ttcttagcag tttctgtttt gttctgggtt aaaagacctg aagctactta aagtgagaag    6780
acagaagcaa gacagagtat ctttcaaata attgctcttc tagcagccgt gtgtcatgtc    6840
tgatcagggc atgattaagc aggacaggtc ttcacatgcc ggccacaaag ccctggaccc    6900
agccgttcac ccttagagag gggcactgtg gaccccgccc gccattcact acgcagcttg    6960
ccagtggggc gggtgctttg caggctcaca gaaaaatcat tcgcccttga aatgtcttat    7020
ctgggcctgg acacctcctt agtttctctt gtgtttcctt tctgtgtaag gctggtccct    7080
caccgccggt ttggtcacac ccctctgttt cctcagggtc acttgtaggt cagcgtttga    7140
actttgtgat ttctatctcc ctccttcaat ccaatctttg acctctagta tttgcccacc    7200
tgacccataa acagagaacc ataatggttc tctgatttgt gttttcaaca aaaccccacc    7260
tttaacacca ctcacctcta ccagccaaca aaaccccggc tttaacaccg ctcgtctcta    7320
ccagcccctc ttctcttagt cgcttcacca ctgaggcctc cctgagcagc tagcagaaaa    7380
ggccttccat cccgctggct ggcgctggta cccgcgaata ggttggtgtg tgtctttcca    7440
gacatgtttg tgcacatata tgttcacatg ttctttcaag acaccatata cacgcttaga    7500
tacacgtagg atcttacata catgctgttc ttcatgctgt aacacagcca tgcttcgtga    7560
agtcactcct gctgtctcta gttcctcacc ttcagttatt cctcagcgtc ctgtgacctg    7620
ccttttgcct cgaacctctt tgacaaaaac aattttttcg gaagagtatt cagcaatctc    7680
ttcagtgaag aaaggtttta aatcggtaat gtaaccagag gtaggaaatg gaaaagtgcc    7740
agaggctgct gcatggaaag tcccttctcc cacagatggc acggaagggc acccaggacg    7800
ttttaagggt caggcaaggt tctcctttcc ctgggtgttg ataacttttta tttcacgtgt    7860 aaaaaacatg tttcttaccc tcttcccagc catccagttc ccctctttgc agatagcaca    7920
cttcctcgta gaaccttcca gagaaaccat atgtatttac aagtagatac ctgatgtccc    7980
actgcacaca caggtgcctc ctggtcttct cttggcagtc tttccagatg aggcttctct    8040
gtcagtccat aaagagcttg ttcagtggca caaatgtgtt atttaatcag gccctataga    8100
taacattttg ttccatcgta ttattacaaa ccagtgcact gtcatttaca tattatatac    8160
atatcaccta catgttacag acagcagatg ggacctttca cattcaggta agtctacctg    8220
tggagtagaa atctggaagt ggagttgggt caaatggtct gtgcttttgt aattacttta    8280
```

```
cctgttgccg agatctgctt ttagaattcc cacagccaca tacaaggcct gtttccctaa    8340
cctttaacga gcccagcgag ttagcacttg ctggttgcgg ccatacagtt aggtggagac    8400
ttgccctggt gtggtgtggt tttatcttag gagttgataa aggttgaata ttgtttcaag    8460
taaacgattt cattgatatt tggtgagttg tttgtctcct ttgctcatct ctgttgagtt    8520
gttggtcttt tcttttttta attttttactt tatttgagac agagtctcac tctgtcaccc    8580
aggctggagt gcactggtgt gatctcggtt cactgcaacc tttgcctccc gggttcaagc    8640
aattcttctg cctcagccac caagtagct gggattacag gcacgtgcca ccaagcctgg     8700
ctaattttt tttttttttt tttttttttt tttttttttt tggtatttt agtagagatg     8760
gggtttcacc atgttgacca ggctggtctc aagctcctga cttcaagaga tccacccacc    8820
tcggcctccc aaagtgctgg gattccaggt gtgagccact gcgcctggct gggttcttag    8880
tttttagaaa ctccgtaagt ttcaaggcat tgtctttagt aggaattgca tgtatttgtt    8940
ttctgggttt ttaatcttgt cttctgactt tgccatgcag ttgttttctt ttctttttt     9000
ttaaatgcta tatttatcag tccttttttgg tatggcttct gggttttgtg tcataatgca   9060
taatgtataa tgcgtttctc atcatacata ttatacatat gcatgtattg tgcatacata    9120
atacacatga cgccccgtac attctgaaga cagtcccctg cagtgtcgcc tggtatggaa    9180
cttgtgtcat tctcttttta tatcaaacgg atccatctgg aattgatttg gtataaggta    9240
caaagttagt tttatatttt ccagatgaca gcccatttgt cccagtgcca tctgttaaat    9300
agtctctgct ctccctccca gatctgagct gtctctcgtt tactcccaca tctatttggg    9360
ttcacttctg gaccctgcgt tctgcttcat ggatgtctcc atccatatga cctcatgttg    9420
gccaggttca ttggatactc ttggttttgt ttcttacctc tcgttcgttt ttgtgggttt    9480
cctacacaga ggaatcccca ggaagggttt ttttgggga ttttgtttgg gataaatatg     9540
gctgtgaggc gcctgccccg gatggtggct tctgcagcct gggtgtgccg gccggctgg    9600
gatctcgctg ccttcgccag ttctggcact gctggttttc ctcttctctg gacatttgtt    9660
ttcagttttt cctctgctttt cctgcactttt tgatgatgtt attcctcaga cttctctcct   9720
ttttcttctt tgttttttgct ttataattcg tgaccttttc agctgtggtt ttgccagtca   9780
cactgatgag tccaaaaaac ctaaaggctc aaccagacct ccagctccca gtgaaggttc    9840
ccagtagctc agtgtggcaa aggcaggttt ctgtcttcca acctgccatg gttcccatgt    9900
ttcccccaaa gtttgcgtct tagaaactta atcccagtg cggcagtgtt gggacatggg     9960
taggtcggga gggctctgcc actgccatta caatgaggta atatccttgt caccggagag   10020
tggttttgt gaaggccggt gtggggctcc tcttgctggc ttgctctctg gctctctcgc    10080
cctttcccct tctgccttcc accatgggat gtcctagcag gaaggcccta agcagataca   10140
ggctgttgct gttggacttt gcagcctcca gaactgtaag aaatacattt cttttcttta   10200
taaattacct actctgtggt attctgttac aggaacacaa aacagaccaa gacaccaacc   10260
ctgacctgct ctgtccttcc cttctaatcc cttccagcca gaggcccagg cctgtcatag   10320
agatgccctt ttttatcccc tccagctggt ttatgaccaa gtcctaaata tctttagatt   10380
tgtctccagt gacaccgtta cagccccggt tcagtgttcc ctcagggtct cccttcttt    10440
ccccctgtac tttcctttct tcctctcctt cctttcccct ccgcttacc cttcccccc     10500
cccaccccc ccccccccg tttctctccc tgccacactt gccatggtgc tcacatacat     10560
ggcacacttc tctggacgca ggcttagatt tgaggcagta tgccagggaa gcaggatgga   10620
```

```
gattagaata gtcttcagga aaccagcatg gccccagcct agcctaactc cactttgctt    10680
ctgattagaa atctgtgtta gaatgcaagt cagttgatgt cattgtttaa agtctgcaag    10740
aaacaacttc atagctgctc cattttattt tctaattaaa tagttcagaa gcattggtac    10800
cttaactctt tttagaaata acactgatgt gcccaactct gaccttgacc taggtctagc    10860
ctcattaaca ttccagtctc ctggcctggg tctgcccgct gtaacccttt ttggtctccc    10920
tggcctgggt ctgcctccat aaccccctct ggtgtcactg gcccctcttt agcctctgac    10980
atcagttccc ttgtgtcatt ggaatggtcc tcgtcaaatg catgctgcag gagcttcatt    11040
tctggcttac gggtcttggc atgatgtgcc atggcctttg tgatctgtcc cctgcctgtc    11100
cgtacacacc tctctctgta ggcgcagttc ctcctactca ctgtgctttc tctctcctgt    11160
gcccttggag aggctgttct cttagactgg acaccggtta cctgtgatac ccctatacgc    11220
attattggtt catagatacc agtcattttg ttgttgcatc cttatcctag accttatgtg    11280
ctgtgttctg tttctgccca agactttgac tttggcagag actgacttttt taaatcacta   11340
gagcctagca gttcctacca cctactaggg gctcacctgc ggagcatccg ttaaacccag    11400
gggcaggagg tgttgggtgg atgaaaagcc gccgtagtac aagtgctttt tcccttttggc   11460
ttttttttt cagtggccac agtagtcact cctgtaacca actcatactt tttatctttt    11520
taatttttgc ctttatccaa tgactacctc tcatatatta tgtagctgga gattctagtg    11580
aagtttaact tgaattttaa catctgtatt ctactttctc attttttattt atttattttt   11640
tttgagacag tgtctcgctc tgtcgcccag gctggagtgc agtggcgcaa tctcggctca    11700
ctgcaagctc cgcctcccgg gttcacgcca ttctcctgcc tcagcctcct gagtagctgg    11760
aactacaagc acccaccacc atgccaggct aattttttgt attttttagta gagacggagt   11820
ttcaccgtgt tagccaggat ggtctccatc tcctgacctt gtgatccgcc tgcctcagcc    11880
tcccaaagcg ctgggattac aggtgtgagc cactgcgcct ggccctactt tcttatttttt   11940
aactttatat ttttcaaaag ctggcatgca aggccaggtg cactggctca cacctgtaac    12000
cccagcactt tgggagacca aggcaggtgg atcacttgag gccaggagtt caagaccagc    12060
ctggcaacat ggcgaaaccc catctctatt taaaaaaaaa aagaaaaaga agaagaaaaa    12120
actggcatac aaaagctttc attgggaaga actctctaac acgagagttg ggctttaggt    12180
tacctgggtt gcactcatac aaggttgtga atgcgtcagc tgagagctcg gaagaagccg    12240
cgtggcatca tgatgctttg gtggccttgt ctcctgtgga gcctgtggag gcatgtatgt    12300
ggatgagttc atttccatgg agtaacattt ttagttctgc aagtaagttt gtctggatta    12360
tatttcttta atgcttttaa aactttaaat catggtaagc ctcgatgttt tagtttgcta    12420
cataatgtca ataaattgaa aaaccgttac tcattctaat taaggtttca tttgtatttc    12480
ttttatactt tcaacagtga catcagatta actctttaga agggagcatt atggcatcat    12540
ttgtctaatt atttgggaca tttgcataaa agcatcaata gaattaccag aaagaaatta    12600
tatccttagg tttcttttttt ttttttttg agacgtagtc ttgcgttgtc acccaggctg    12660
gagtgcaatg gtgcgatctc agctcactgc aaacctctgt ctcccgggtt caagcgactc    12720
tcctgcctca gcctcctgag taactgggat tacaggcacc cgccaccaca cccggctaat    12780
ttttgtattt ttagtagaga cagggtttca ctatgttggt caggttgtct tgaactcctg    12840
acctcaggtg atctgcccgc ctcagcctcc cacggtgctg ggattccagg tgtgagccac    12900
cacgcccagc ctatccttag gtttcttaat gactctaatt aaaacatgta tataaggaa    12960
ctagtgctag aaggattata gtctagactt gaaaaaagat taaactgttt gaaataggaa    13020
```

```
gagatttagt gtatggggaa gaggaacaac cctcacccct actctgtttt gggcatttta   13080
ataaaattta gaagcttgag cataatgcta acaacctagt tatagtaaaa ttagtaaaat   13140
tggccgggtg cggtggctca cgcctgtaat cctagcactt tgggaggccg aggcgggcgg   13200
atcacaaggt caggaatttg agtccagcct gaccaatatg gtaaaacccc atctctacta   13260
aaaatacaaa aattagccgg gcgtggtggc gggcgcctgt tatcccagct actcgggagg   13320
ctgaggcagg agaattgttt gaacctggga ggcagaggtt gcagtgagcc aagatgcgc    13380
cactgcactc cagcctgggc aacagtgaga ctccgtctca aaaaaaaaaa aaattagtaa   13440
aattaatgag atactttgaa agcacagagt attgaggttg tgtgggaagc actgtgtggt   13500
gtgtaaactc tacccggaca caaatagata ctcacagaac ttgcacacca cctctgggag   13560
attctcctga ctccaggttc ctggtagagt atctttcata cgtgagaact caggccattt   13620
tccagtcggt tccaaccttc tctgcacccc gactcccagg ccttttttct attgttttcc   13680
accactgatc agtttcgcct attctaaaac ttcatttaag cagaatcatg gaattcttgc   13740
tggcttatta tctgttggct tccttcgttg cgtgatttta gtggctggtc tagggatgac   13800
actgtagatt ctgaactttc gacactgcat tgtgccacac gtcgtgcagt gtgtcatttc   13860
tcaaagcact tatatgtgtg ggttgttttt taaataggtg gaaggctttt aaaccagcat   13920
accattaata gtgtattgag gaagttaatt tatcaatgtt atttttcctt ttacaattgc   13980
taataaagat atgaggtgag gagcagcagg ctacagggag gagcgatgcg tgggggcgta   14040
tcagtggttc taggtgcatg caatgatggg cagcggactc gggagcgatg tgtggaggcg   14100
tgtgtgttcc ccaggtgtgt gcggtgaggg gcagcaggtt caggggatg cggtgggggc    14160
gtgtcggtgt tccccaggtg tgtgcggtga ggggcagcag actcgggagc gatgcgtgga   14220
ggcgtgtgag tgttccccag gtgtgtgcgg tgaggggcag caggctcagg gggatgcggt   14280
gggggcgtgg cggtgttccc caggtgcagg aggctgctct gagggtgtcg catgtatttc   14340
atttaatcct cataacagct ccatgagtca agttctattt ttgtccccat tttagcaata   14400
agaaaacaga cacagagggg ttaagtataa ataatttgac aaagacgaca ttagtgagtg   14460
gctatttta ttatgtgaag ttaaaattgt ttgtgtgttg acttcatcat ttaaagtgag    14520
aggaagaacc tgaggaatat gaaatgagat gagggagaga gccccagact ctgcggctgg   14580
tagaagtagg gagtgtgacc tcatccccgg cttctgccag ctctgctgat gcccggggct   14640
gccccatgtg cgcggccggc cctgggcggg atccatggtc ttggtgacaa agctcctctc   14700
cctgccttcg ccccagcggc tcgttttat tcattcagca cagagtgtgt aactgatagt    14760
cctcagtacc gcagtctgat attttgttgg ggttccttt tttcttttca tttaaaggta    14820
aaacctacat ttagtgaaat gcacatattt taagtgtgtc atctggtgtt ttcaccactt   14880
cantttttt ttggttttgt tttgttttt ttttttttt ttttgagac tgagtctctc       14940
tctgtcaggc tagagtacaa tgtagcgatc ttggctcact gcaacctctg cctcctgggt   15000
tcaagcaatt ctcccgcctc agcctcctga gtagctggga ttacaggcac gcaccaccat   15060
gcccggctaa ttttttgtatt tttattagag acaaggtttc accatgttgg tcaggctggt   15120
ctcaaactcc ttaccttgtg atctgccctc ctcagccttc caaagtgctg ggattacagg   15180
cacgagccac cgcgcccggc caccacttca gttttgacag aagcagtaag ccttgatgcg   15240
ggtttgtgcg gtatgaccgt cagcccgagg aattccctcc cgccattttc caccttctcc   15300
cacccccac ccccaggcct taaaaactct ttctccctct gttctgtttc tttccacca     15360
```

```
ttgattagtt ttgccatttc taaaacttca tttaagcaga ttcatggaat tccattttat    15420
ctgttggctt cctttgttgc atgattttag tggctggtct agagatgaca ctgtagatac    15480
tgaactttac acagtctgct tggagttaat accgtacccc gccttgtgca gtgtaagaag    15540
ctggtcactg tcttgcaacc aggtgccttc ccggtccttg ctgtggcaag tgtacatgtt    15600
acatctgtgc tgtagacatc acaacatata tagtattgtt gtttgcttca gtatgaatgt    15660
acctttaaaa aaattacgag gaaaatattg tcttttatat atactcacat atttacccttt   15720 tttcccccaa cccctaagtg gaaccaggtc tatttaccat tttggtgctt ttcattcctt    15780
accgatccag tttgttacca tatccttttca gtctggcaaa ctcactttag tattttcggg   15840
agtgtaggtg tgctggcaag aaaggctctt agttttcttt tatcagaaca tgttttgctt    15900
tcacccgtgc tattgaagta tgtttgcact ggacgtgagg tcctttgttg gcagcttttct   15960 tctactggga ctttgagaga agtcgagacc ctgtctctcc tccagggctc tgctgttggc    16020
tgctcccctg tgctcacaag ttgttttttct ccagctggct ttaagatgga ctgtctttgg   16080
tatttgagca gcctgactgt gatgtgtcca agtgtttatt gaatttatct tatttggtgt    16140
cctgaactta ctagatctgt aaatttatgc cttctgccag ctgtgggaaa ttttcagcca    16200
taatttctcc aaaatgtttt tctgcctcaa tctctctctc cttatgggac tccagctcta    16260
ggtatgttaa actgtgtgat attgtccctg aagctttgtt tgattgtttt cctttcagat    16320
ctttttctct ctctgttctt tgggttggat actttttatt gatccatctt cagattcact    16380
gagtcttctg ttacctccag tctgctgtta aagctcgtcc acaggatttt tcttcgttta    16440
gaaatagcat ttttttagttc tggaatttcc tttttttttt tttttttttt tttaagacag    16500
agtcttgctc tgccacccag gctggagtac agtggcacac tctcggctca ctgcaacctc    16560
cgactcctgg gttcaagcga ttctcctgtt caacctcccc aagtagctgg gattacaggc    16620
gcccaccacc acactcaggt aattttttta ttttttttgta gagacagggt tttgccatgt    16680
tggccaggct agtctcgaac ttctgacctc aggtgatccg cctgccttgg cctccctaag    16740
tgctgagatt acaggcgtga gccactgcac ctggccctgg aatttccatt ttttaagaaa    16800
tgttctcttt ctctcttgag acccgtttgg cttgtccagc ctaagtccct ttgccttttct   16860 gttcctgagc cccgttgtaa gggctactga gtcctgcctg tgctggcagc atgggtgtgt    16920
cctgtgcctg gtctccagag ctaactcttt cctctttgta caggttatat ttttgtttct    16980
ttccatgtct agtaattgtg gattgcttct tggattttgt gagtgatctg ttgtagaaac    17040
tctggacttc gttctatcct cctgaagatt gatgatgctt tgttttagca ggcagtcagt    17100
ttggctggac tcaaactcca gatactcttc ctgtgttatc agcagctaat atctctgctc    17160
agttgctgta gtgtgacctt gctgtcctgg acctgccccg tgcctgcctg ttgcagggct    17220
cacacagagt tgatgtgcag agcgtgctgt cccctcccag ggtgctctcc cttccagggt    17280
ttctcctgtc gctttccagc tgcgatcatc taccagaatt cccctctctg gttttttcagg   17340 tgagactgtg gggctctctg tgagctttag ctgccccct tctctgagga ggaccaggtt     17400
ctgccccagg acaagaaacc cgtgcagtgc tcagctcgct ctgggcacag gctccctcca    17460
gtttctgctt gtcttggtcc tgttcagttt gttttttttat gctttgtcca gagtttatag   17520
ttatctgcaa gaggattggt ccaacgtctc agccattact gaaggtagaa ccacctgttt    17580
tatatactcc aggggttgca gaaataaata cgaaccatgt gttctaggaa gaattcactc    17640
tccctgagga agggaggctg tgaagggggg ttttatacta actggaacat gtgctgttaa    17700
aaggatgagg tgctgtgcgg agagaaggct agcatggccc agtgccttga agttcatggg    17760
```

```
tccatttgga ggatgtcagt ggaatggttg tctacatgct ctagcccctg gtggcggtca   17820
gccacgggaa ggagagtcag gcgtgtggtg aacttgccag agaagcaggc ctgggctagg   17880
cttcacctgt aggtgtgaag ttcagttggg cagataccag gtgcctaggg gatgagggtc   17940
tggtcatagc tgcagtggga ggtaaatctg aaacttttg gcctaaatgt cttctgtgat    18000
caatccaggt gagccctttc tggtctgatc ttttgttgca tggctgacag taagagatgg   18060
ggaccctggc tctgaagcag cgatgccttg ttcataatag ggtgtcccaa gaagactcct   18120
ggaatagagt ttgtggtgcc tgcagaaaca aagcctgcta ccgattttta ctgacacttt   18180
ctggaccttg gatgcactct tgttttgaac caggggtttc tcgctcctgg cctcttcaag   18240
tcctgttctt tcccatccta gatgcctaag tgttctgaaa ccgaacctat actgtggctg   18300
gtatccccaa agcactgtaa agcagccact gaacgtgct cactgctttg aatggtccat    18360
ctcagggagc tgaatattat agtgggaacc aaaatggtca tgataacgca gtttagttat   18420
tgtgattaga catttagcca gcttctctaa gaaaacccca gtatttaagc atattcctgg   18480
ccaaatattc acaataacaa tattgtgtgt attatgtact taacgtcaaa agtcctgaag   18540
atgggccggg cacggtggct cacgcctgta atcccagcac tttggaggc caaggcaggt     18600 ggatcaccta aggtcaggag tttgagacca gcctggccaa catggtggaa ccctgtctct    18660
ggtaataata caaaaattag ctgggtgtgg tggcgcctgc ctgttatccc agctactcag    18720
gaggctgaga caggagaatc gcttgaaccc aggaggcgga ggttgcagtg agctgagatc    18780
gtaccgttgc actccagcct ggggaaaaag agcgaaactc catctccaaa aaaaaaaaa    18840 agtcctgtag ataaagataa cctcagggaa tgtctcatct gccatcctct tggatgtggc   18900
atcagtggag ttagattgca tctatgcctg caatggagag ggtgctggct gcagcctctg   18960
cccctgaagc tgttgcagct cactgttcct aacattacga gtgtcacatc atttaaattt   19020
tttcttacac tgggtgcagt ggttcatgcc tgtaatccca ctcaccactt tgggaggct    19080 gagttgggag gatctcttaa ggccagtagt gcaagaccag cctgggcaac ataggagac    19140 ccccatctgt acaaaaaata aaacaatta gccgggcgct gtggtacacg cctgtagtcg    19200
cagctgctca ggaggctgag gtgggagatg gcactgagct gtggttgtgc cactgcactc   19260
cagcctgggc aacagagcga gcccctatct caaagataaa aataaaaag tgcattttc     19320 ttgagggga aggaaccatc atggtggccg tattgctta ctttctgatg gtgtcgtctt     19380
cagagattgt tgagattggg ttgttggttc ccacgtggcc atgtcctgtc agtgttgctt   19440
ctgtgtgttc cctcgctgtc acctgttgct cctaagtgct gactttgtac cttttcgag    19500 cagcctctga ttggttttctc cccgacccgg cccgcgccac agcggtgctg ctggtggtct   19560
gctctgtggg gccgtgttga gagagaagct ctgaggaga ggctttgcat gcgtgcctcg    19620
gtgcacggtg ccagcctgga tccctgtggc tgtggaatgg gcgcttgctg tttgccaggc   19680
tccatcctga gagccatgct tggtggactg gctacttcaa tccttgcacc aaccctcgga   19740
agtcaatatg gtggctgtcc ccactttaca gatggggaca caggcttgga aatgccacat   19800
cacttgtgtc gcacgactag tgatgggggc ggccctcccg agggtctgac tgtagggccg   19860
gcatttggca tcactacagg aggttgacac tttcactatt atgtttactc ctcctacttc   19920
agttccaccc ctaccccag cccagttta ttgacacttg cacttgtctg tgcaagcatt     19980
ttctctcctg ttgcataaag ttgtttttttt tagtggaggg tagtagttgc tcagaagcac   20040
tggaagacag cagtggtcag agcccggtca gcagtgaagg tcagcgccat tgccggcctc   20100
```

```
cgaccctagt ggtgagtagg tcgctgctgg acaggagggc aaggaggggc taggaaggca    20160
gaaatgagtt gttgctcatg agtacaagca agatgctggt gttctctctg aagtcaatac    20220
atccgttaag atgcccttg aaccctgttt tatgggatta caggactagg aagtatgtct     20280
ttagcctccc tagggctctc gactttagac tccctctgtt tctacaggca gtgtctggaa    20340
cagggattct gggtgtgttg gaggctgact gtagggaagc cctaccccag aggtcccatg    20400
tggttggccc ctggtgggat gtcttggcac ctggaggcct ggaagccccc gcgggtgggc    20460
agttggggcc ggtgttccta gaggaggccg tgctgccctg tggctatttg tgaaagagat    20520
ttgcatctgg tcactctggg agctggtcta gttaagtact gggttccctt tgctgagatt    20580
ttaagcagta atctttttc tctctttctc tttttgatga gtagagctct aggttaagaa     20640
atattaaaag gaatgttttt acatggaaaa tgttttttg gttagcgttg gctttcactt     20700
ggtctaagtc agcaaatagc tttcactctt aaactgtctg tcttcttgtt ctggttttta    20760
gagacacgta atgactattt tagcaaaatg cttacaaatc tattttgttt ttatgttta     20820 tgttttac gttaacttaa aagtatttaa cagacgttac tccttcctgt atagaggtag      20880
gttaattgga aaacaaattg aaaacactat ttttcatag tcatgtttac tgtattttgt     20940 ttgtggggt agacactttg aagttcatgt taaccctga tgtgcccggc cctcgagata      21000
tgtgtggaag gaaagtgtgg ttatggtttt agaagcttgc ttttctata ctttcatat      21060 cattcacatc ttgtagggag gtatttatat ttagacttaa tatctgtaac ttttttaaat    21120
tctagaagta gtgattgttc ctcacagaaa aattggaaaa cagaaaaata aaataaaaat    21180
tacccagaga taaatgctag taatatttcg gtgtacctt gtcttttctc agtgcctgtt     21240
tgcacacaac tgatgtacgt tctgcccatt ttcacattat ctgtgagcat cctgcatgcc    21300
ttttaagact gcataatatt cagtcatctg gacatacaca tttagcgacc tatttcaata    21360
gtaatctgtt gctgggatgt ttatgttgtt tgttttctt tttgctcaag ctgagataaa     21420
tctccttaca cacaaacctt tgactacatc gctgattgac tgtatcctaa cagcagactc    21480
ctcccagtgg gattagtggg tgaaaagcta cagatgggaa aaaagctcat cacatcctgc    21540
ctccttgctg tccagacagt ggccccaggt tacactcagc tgaggacgag gccaccccct    21600
gcagctttat gagcatttga ctcctgagaa cattttaact gtagtccaag taattaaata    21660
attattcaag ctgtcatgtg cttgttttca ttatttattt atttatttat ttatttgagt    21720
tggggtgtcg tgctgtctcc caggttggag tgcggtgatg caatcatagc tcattgcagc    21780
ctcaacttcc caggttcaag cgatccccc acctcagcct cctgagcagc taggtacagg     21840
cacacaccac cacactcggg taatttctaa attgtggtag agatgtagtc tcactatgtt    21900
gcccaggctg gtcttgaact cctgacctca ggagttccac ctgtctaagc ctcccaaagt    21960
gctgggatta caggtgtgaa ccactgctcc tggccccagg ctggttttga actactgggc    22020
tcaagcgatc ctcctgcctc agccccccaa agtgctggga ttgcaggcgt gagccactgt    22080
gcctggcaag tgcactggtt ttagaacaga cgatcacatg tcgtggtaaa gtctctactt    22140
gagaagatag gccctggccc ccagtgcagg gaacacggag ctggggtggc tgtgggtggc    22200
tctgtcctca tccccagtgc ttctgggggt gtgctgccca caggggtgca gcagatgctg    22260
tagacacagg gagccctgcc ttccgggagg cccagttgcc ggtgcccctc ctggatcctc    22320
ccagagctcc gagtctctgt gacagcactg aagcaattta attgtcctcc agccacaccg    22380
caagcaccac aataataaca gcaactaaca ttttgaatgc taacattttt ccagttcaca    22440
gtactagaaa tgcattttac tgaattctca caaaagcctt aggtaggtgc cattatttcc    22500
```

```
atcccatagt ggacgaaaca ggggctgccc tgtgtggacc cagcactggc cgccgagacg    22560
gctcctgacc gctgtgctcc gctcgcctcc ttggatttaa tgtgcacaaa tcacagacct    22620
ctgtagttac aggacctaaa gtctgcactt gattctgctc cctactggcc agatgacctt    22680
ggggaaggca tttaggaact gacattcagt ttttcttgtt tttaacatgg agataatttg    22740
atctgtgtac gtcacgtact gcagggatca gatggatgat ctcatatggc tgcataatgg    22800
atacttggga agaactgtac aaaaggtggt tatagccggg tgcattgtct catgcctgtg    22860
gtcccagcta ctcgggaggc tgaggcagga ggatgacttg agcctggcaa tttgagacca    22920
gcctgggcaa catagaccat gtctccaaaa aaacagacaa aaatgctagt acttttgtt    22980 cttttattct ccatggtctc tcacaatgtg tcttgacatc gtaggcattc cattggcacc    23040
tggcttttta aactgaccgt attcttttta aagatgtcta gacctggctt tctcagcctg    23100
cgtcgtttgc cagctcccag gtattccaca tgcagacgca gtactcaata ttagggaaaa    23160
taaactgtat cagggagggc ctctcagcct tggcactcct gaggcctgcg ggcaggtact    23220
tccttgctct ggagctgtcc tgggctctgc aggatgttta acagcatcgc tggtctccgt    23280
tggctgcatg ccacgagaat ccccacccca gttcacagaa aatgttttca gctgtggcca    23340
gatgtcccct ggggacaaaa tttcccccag ttgagaacca ctaggttagg gaataataag    23400
actttataag ttaagttagg aaaaacatct aacagtgtgc taaaaaacgg gggaaggggt    23460
ttgaacctga ggcagtagat gataaggaac tgtttgtagg ttaagcctgg catggtggca    23520
tgcgcctcct gtagtcccag cttctctgga ggctgaagtg gaggaccact ttttttttt    23580 ttgactatgt aattaagggt atcatttatt gtaatataag aacatattct aaaacagctg    23640
aatgaacatg cacaacacaa tgtgatgaca catactctcc tgaatttatg taattttcc    23700 ttaagatatc tcttaatgag caatattatt tttaaaatgt taaataaaat ccttaccatt    23760
ggccagtggg atactgaata ccactattta aggaagaaac ctgaaatggt tacgtacaga    23820
tgtcaccatc tgtacgtcta cccttcctac tttcaaaagg ccacttaaac ttcttcatat    23880
aaaaaaacac atgaatcttt agagaacaca tacaaataaa tgaagattta catctaataa    23940
tctatcttaa atgtaccatt cttaagagac agaatcttac cttgaaatag ccattagaaa    24000
aaaccgttgg gccaggcgcg gtggctcacg cttgtaatcc cagtactttg ggagccaggc    24060
gcagtggctc atgtctgtaa tcccagcact ttggggcca agtgcagtgg ctcacgcctg    24120
taatcccagc actttgggag gctgaggcgg gcggaccacg acgtcaggat attgaaacta    24180
tcctggctaa cacggtgaaa ccccgtctct actaaaaata caaaaaatta gccgggcgtg    24240
gtggtgcgcg cctgtagtcc cagctacttg agaagctgag gcaggagaat ggtgtgaacc    24300
cgggaggcgg agcttgcagt gagccaagat cgcaccactg cactccagcc tgggcgacag    24360
agcgagactc catctcaaaa gaaaagaaa ccgttcgacc agggaaattc agagtcccca    24420
aggaagtcaa gttgtcatct ccagatcctt gacacctatt ccaattttca gaaccaacgg    24480
gaattggtgg gatgacatta aaaataggct tctgatccta ctgttgagaa agggatgctg    24540
tattcatgtc atagtggtac atctgtcctc cagaggtact cacaccgtga acagaaatgg    24600
cagacatttt attaccaatc atatttgctc caggagagct tgcctgacag taaactgtgc    24660
ccagtttctc ttgcttaatt accccagggg tgcagagttg gatgaaatct ttttctgttt    24720
tcgcttgggg cagtgttaca ttattgaggc ttgataaaaa ccagatctcc attatcctta    24780
attttgggtt tagtgtccgg taaaacgaga ggcttgcagt cctcattcga gtttcctttt    24840
```

-continued

```
aaaaggaaga atagtcttct cccgccagag gagaaagcag acagttttca tctatcaaca    24900
ggtctgatct ggtggaggac cacttttgag gccaggagtt agaggtcaga tggggcaaca    24960
tagcgggacc ctgtctcttt agtaaaaaaa aaaaaaaaaa caattttttt ttttcatgaa    25020
aaacacgtga cctccaaagt gactgtgagg cttttccagg gcttgttttt atgtggcatg    25080
ctgatgtgaa tactgttcag gtccgtattt gtaaagaaac aaggtgagga gggcagtggc    25140
aggctgcccc tctggtgggc acggttagat gtgactgtcc cagtaggggc tcctagccat    25200
ggagagtgga agccatcaca acttcacttt ctccagcctc taactgggaa ttgagcattc    25260
cctgccttta tggaagcagg caggaatcca cagtcatacg aacagtacct gtgacttggt    25320
cacagatgca gtcacagata ctttgattgc acagtcgtag aaagcgtctt caagtctcct    25380
tcatgctcag cgctcctgtg aagtgagctg agacccacag actctgttcg aggagcccat    25440
ttgtcttcta atacttagat gacggttttc aatataattg gctttgtttg cagtcctgtg    25500
tattttatgc atttaaaata tgtttcttag aagggctcag taggtgtcat cgaactgcca    25560
gagaggtcgc tggcacaaag aaaaggttaa accctgctc taaaagctca ctgccgtttt    25620
tctgagcagt tttcaaatgc ccaccagtgg ggtgcagcga gtcttctgca gaccgaggct    25680
gccgtcagtg ttgggggggct gtgcttccat ctgactgcgt cagcacgtcc cacttggatg    25740
tctttggaag agctttcagg aaatagattt ttagaaatta attctcttct aaaagttatg    25800
gtcaggtccg tgaacattaa agtgggttgt aagcacagag ctgtaaagta gcctgtgtgg    25860
tgctgggttt ttttctgtca ggcggcatga actaaggaca aaccttttt taaaaaaaag    25920 cgtaaatacc tgaggcgggg ggtagttagc gggggtcaca acctgcagcc agcgtcagct    25980
cttctgcagg cgtagctcct caccttgcc tggaagggcc tttgattccc tctggtctaa    26040
ttgcgcagtg cggggattcc cttttccatc ccatctaaag ggacgttgcg agaccgggc    26100 tcggtggctc acgcctgtaa tcccagctaa ggcgggagga tggcttgagc ccaggagttt    26160
gagatcagct gggtaacat ggtgagaccc tggctctgtt tattttttt taataaaaaa    26220 ataagaggag gctgttgagc ctttgactgt tttgatcatg gtgaagattt accttgaaat    26280
attcatgcag cagcattatc atgtgggagc tggttagaaa tgcaagattc tcaggcccac    26340
cccggacctc atgaatcaaa cctgcgtttc agccagatcc ggaggcattt tgcacattaa    26400
agtttggaag cagaggcctc ctctctttaa actgtaacag taagaagggt gattgcataa    26460
gagccagagg cgggctgccc aagtccaggt gcccctagat gtgtggccac tgtggaacct    26520
cagtcagctt tcctggaaga gccccagggg cgggtgtgcc ccgtgactac cagtagcttg    26580
cttcagagtc atatttcatt cctgggttag cgctttgtag atgtggtgga acaatctgat    26640
tgtctgttac ataatgtaga ttgcagaagt ttttgtttga aatagaagtg ctttccgttt    26700
gattctgaat ttcattaaaa tttggtgata tcatgatgta ttttacagat ccttattaac    26760
ggcctgcttc atgccaggcc cagttcgaag tgcaaaggaa cagcagtgaa caaagcaaac    26820
cagaaacaca gctgccttgc tgagcatcga gaagtcttgc taagaaggac gtttgagtat    26880
agatgggaag gcacagggc gcttccaggc agagggaca gccagggcga aggccccagg    26940
cagatgtgac tgctgtgccc agggcagcag tgcatggagt gaagagctgg gggaggactg    27000
gatgccaggt tgcagggcc aggcagaggg ttttttgtggg ttgtgggaag aggctggctg    27060
tggagaggaa gagagcagct tatcgttgcc ttcctagcag tagcagaagg cagccttttgg    27120 agccggtcag tcttccctct cgtgcacatc aggccagatg acgagtcctg cgggtgagcc    27180
tgagtcagag agcacttgag tggaacatag gtcacgtgga gcaaactaac ttcaccaaaa    27240
```

```
ataaccccaa aacagcattt ctgggaaaca caagtgaaga cagcttctca tgtaaacaaa    27300
ggaacaaagt tacgataaag gcttggttgg aaaaagtgaa catgtggaaa actaagaaga    27360
aattccttgg gaaatatac ggaggaaaac aggtctttct tttccagcag ttgccattct     27420
aaagagtttt ccttcctgtc ttgatgtcag atgcagtgtg tgttttgcta gggtggctca    27480
cgggctttcc ccttccagtt gtggttgtgg cagacggacc tacagccttt agctcttcct    27540
gtctgcgtgg ggaaaagact tcctgttttc tctgggtctc ctctttgtcc ttgccgggat    27600
tggaccggat gatgggtgca gtataaaacc tggacttggg gtcgtggttg gttcttagcc    27660
tagctgcaaa ttagaatcac cagagaagct tcaggcacaa acaaaagaa gccccgtttc     27720 cagaaactct gattttggtg gggagtgtgg gatgtggttt tctcagggcc ttggtgttcc    27780
agtgtgctgt cgaggccgag aagcactaat cagtactgct ctccttctct ccaaggctgt    27840
gttttcccct gctcagccct cctctcccct tcctccccta gcaggctgag agttgggagg    27900 ctggcttttcc tttgtgtctc tttggagtgt tttagggtgg gcaggcggtg tgtgtgtgcg   27960
agaacgcact gatcacacgt gtttcttttt ggggcaggaa ggtttgccac taccagcaaa    28020 gttgaactg ctgatgctgg ttgtcaaggc agctcactct cagctgtgcg tgctggtgtg     28080
cacctgtggt cccagttact caggaggctc aggtggaagg atcacttgag cccaggaggt    28140
cgaggctgcg gtgagttatg attgtgccac tgcattccag cctgagtgac agaagagact    28200
ctgtttgttt ttttttctcc tgagacggag tcttgctctg tcacccggga tggagtgcaa    28260
tatggtgtaa tctcagctca ctgcaacctc cacctcccgc gttgaagcga tccccctgcc    28320
tcagcctccc gagtagctgg gattacaggt gcccgccacc acacctggca gttttgta     28380 tttttagtag agacgaggtt tcattcacca tgttggccag gctggtctcg aactcctgac    28440
ctcaggtgat ctgtccgcct cggcctccca gagtgctggg attacagacg tgagccaccg    28500
tgcccagctg agactccgtc tcttaaaaaa gagaaaaggc agctcacttt ctcttcttag    28560
aaccaggact tagaatatgt accaaagtag ctaagagaat gtggaggttc atgcatcagg    28620
ccaaatcgaa tgggctctgc tgtggttata tttcttttgt tttcttgaga cagggtctcg    28680
ctatcgccca ggctggagtg cactgatatg atcataccct actgcagctt caaactcctg    28740
ggctcaagcg atgctcccac cttagcctcc caagtagttg ggactgcagg cacaggccac    28800
gacacccagc taattttgt gttttgtag agatgggggg ctcaatatgt tgcctaggct      28860
gaccttgaac tcgtggcctc aagtgatcct cctgctttgg cctcccaaag tgctggagtt    28920
acaggtgtga atcactgcac ctagctgtgt ttctttttc tttttttctt tttctttgag    28980
acagagtttc actctcgttg cccaggctgg agtgcaatgg cgcaatctcg gctccctaca    29040
acctccaact ccgggttca agcgattctc ctgcttcagc ctcccagta gctgagatta     29100 gaggcgtgcg ccaccatgcc tggctaattt cgtattttta gtagagacgg gtttcaccat    29160
gttggtcagc tggtctcaa actcctgacc tcaggtgatc tgcctgcctc ggcctcccaa    29220
agtgctggga ttactggcgt gagccactaa gcctggcctc ggccgtgttt gttttttttc    29280
tttttctttt tttcttttt ttttttttgt gagatagagt ctctgtcgcc caggctggag     29340
tgctggggcg cgatctcggc tcactgcaag ctccaccttc cgggttcaca ccattctcct    29400
gcctcagcct cccgagtagc tgggactaca gcacccgcc accatgcctg gctaattttt    29460 tgtatttta gtagacggg gtttcaccg tgttagccag gatggtcttg atctcccgac      29520
cttgtgatcc acctgcctcg gcctcccaaa gtgctgggat tacaggcgtg agccactgca    29580
```

```
cccggccttg gctgtgtttc ttgtacagtt aatgtgttaa cctcctgagt tgtcttgcaa    29640
agtaatatgt actgtttgga actaaaaatc tccttgtgta agatttgtat cgtacttgta    29700
tcggttctat tatcttgttt agtgggaaag gagttcattt ctgggttctc taaccataga    29760
ataatgaaag agactttgtt aaatcggaag gaaatcaccc aatttaaatt acaaatataa    29820
gaaattcaaa aaattttatt ttcttgataa catgttatta agttatccaa agaattgact    29880
ttctggagga gttgctgcat ggctaggact tttttttttt tttttacttt tttagaaatt    29940
taaatagaga cagggtctcg ctgttaccca ggccagtaac aaactcatag tttcaagcag    30000
tcctcctgcc tcagcctccc aaagtgctgg gattatagcc atgagctgct gcgcccggcc    30060
ttattttctc gagttacata aacttcccaa ttatgtagcc ctgtgacaag ttgcttttct    30120
tggaaggcat ctgttgagcc gcgtgggatc tgttagtccc tctccctgca tgaacagccc    30180
aggagggctt cttgctgggg ggcaggggca ttgacagagc tgggatcaga ggatctcgct    30240
atggacttgg gtgtggcccc tgtggcttgc tgtctgtgga atacagcagg tgctggtcct    30300
gccggagtgg cagcagtctc caccctttcc tcccaactcc agcttccgcc tccactttca    30360
tcctgtctga ggtcgaggcc acgcctacct ggccagccct ctgcagagcg agtgctggga    30420
tctgtgcttg tgagtgaact tagggatgt tttggtcaac tgccacctac cgtccaggta    30480
tgagatgaaa gaacaagtgg aggctggaga ggtcaggcca ttttccaggc tgcttgtgcc    30540
atgtactttc ccatactgtg aatgcagcat tgcttatcag ctcttttgat gaactttaaa    30600
atcttacgcc tctcatatcc tccgaaattt tgaaatacat tgagactgta aagaagttac    30660
agcattggcc attttattc ttctaaatcc tataagttat aaatgtgttt tggctgtgaa    30720
attttaaaat actgatgggg agggaatgaa ggttattgct accccctcc tctcgcccct    30780 ctgggccct tccggcttat tccacattca caccatcact gaacccagga agcaggaggg    30840
gtgggacgag cctggctagc ccgtggcttg tttctgcgct tgttgtgtgt tgggagcact    30900
ggtggtcagg agggcctccc ccacccacag cttgggggcg gccgtcacct gcaggtacac    30960
tgtctgtgct tagcaggtct ctgtcgatgg ggactgaggg tgtgccccgc tttccctgtc    31020
acagacactc ctgcagtggg cacaccccat caggtcattt tctcacgtgt gagtacttgg    31080
tatggtgaat tcctagaaat ggaattggga tgtaatttta ggatatgctt tttcaaactg    31140
taccccaaat agaccgagtt gtattctgtt ctttgctgtt gttttaaag cattttatga    31200 tttaagattt atagaaggag aatgttaagt cctgctgtgt aattcgtttt atagggagct    31260
atttgatttg aagaaatatg aaaataaaag tttgcctcaa ataaaaatat ataattcatg    31320
ccaccttggc taacatagtt cctttttttt ttcttggaga tagagcctta ctctgttgcc    31380
caggctggag tgtagtgtca ccatcttggc tcactgcagc ccctgcctcc tgggttcaag    31440
tgatcctccc acgtcagcct cccgagtagc tgggactata ggcacttgcc atcacgcctg    31500
gctaattttt gtattttaa tagagatggg gtttcaccat gttggccagg ctggtcttga    31560
actcctgggc tcaagagatc cacctgcgtc agcctcctaa agtgctggga taacaggcgt    31620
gagccaccgt gcccggcctc tttggctacc atagtttctg tgcacccgat gaaccccagc    31680
cacaagacgt aagcgcccgt gtttgactca agttatctga gctcttttgc actttcagtg    31740
gagagtagta ggtgaaattt tcatctttct tggggaaggc ttattattat aataatacat    31800
gttttgtaga aaaatggaaa ccaaggtaat tatgaaagac ttaattaaca aataaaattg    31860
tcccctatta actccgtggg agaaaataag atgattctgt ttctgttccc tcagatcact    31920
ccaagaactg aggcccctgt cagcagtgtc agtaatagtt tggagaatgc cctgcacaca    31980
```

```
tcagcacatt ccacggagga gtcgctgccc aagaggccct taggaaaaca cagcaaaggt   32040
gagtgcacgc acgggtttca ggaggacgtc tgacggacgg aggatgggca caccccagat   32100
ccccgtgagg gcattgttaa atgctttcag atctttcata aatgccaatc ttatgtgtat   32160
ttttctaaat tctataagca atacatgaat atgctttggc tgtaaaaatc tcaattattg   32220 atgttttta aggagaagtc cagacgtggt ttctcacacc tgtaatccca gcactttggg    32280
agactgaggt gggcggatca cctgaggttg ggagtttgag accagcctga ccaacatgaa   32340
gaaaccccat ctctactaaa aatacaaaat tagctgggcg tggtggcggg catctgtaat   32400
cccagctact cgggaggctg aggcaggaga atcgcttgaa cccaggaggc ggaggtcgtg   32460
gtaagccaag atcacgccat tgcactccag cctgggcaac aagagcaaaa ctccgtctga   32520
aaaaaaaaaa aaaattagcc aggcctggtg gtgcacgctt gtaatcccag ctacttgaga   32580
ggctgaggca ggagaattgc ttgaacccag gaggtggagg ttgcagtgag ccgagatcgt   32640
gccactgccc tccagtctgg gtgacagagt gagattacat ctcaaaaaaa aaaaaagggt   32700
gggaggaata agtttacac cctcctcccc accccacatg gaaatcatcc ttaaccacta    32760
gagcggtgtt gtcctgaagc gctctctgtg gtgacggagt gttttccacc tgcactgagt   32820
tggttgtcag cagccacacg tgccttccgc gcacttgaaa catggctaat gtgactggct   32880
acctgagtct ttattttct ttaacgtaca cgtggacagc tcagcgtggg tagtgaggcg    32940
cggcctgagc ccctgtggct ctgcacgcca gcctctgccg tgttatgatc agctgcaaag   33000
ttggtaacca tgccatagta gtggaggctt tggggagggg agagtaaggt ggtttgtagg   33060
actagatgga ccagataatg catacccggt aaaataaatg cttgtgtggt ttgcagaatc   33120
gtcagtagtg gggagacaga gaccagggtg gcgctttcca gtggggtcac tggtcctgag   33180
cccccatggc atagaggtac cgaggccggc tgtgtccgca tctgctggcc tctattctcc   33240
ctgtgttatt tacaaagatg tttgtctcct agcaggtgcg ccacgtgagg cccagagccg   33300
cactcgctca ccctgtgcgc tctcccccaa ccgccccgca ccgtccccgt ccctggcacg   33360
gcgcttcgtg ccttccacag gcttcataac tgctttgttt ctaaagtccc gttctgacaa   33420
cgccatcgag agccacctgt ctctgattta gatcctaact caggaaggac ccatttcccc   33480
agcagctgca gcctctgttg atgtaatgag cacggtatgg tatggagaca gtaactcctt   33540
actgcagccc tgcgagggct cctgtcccca cttgaccctc gtagcaaccc cctgaggtcg   33600
caacagtctt tgtcttatcc actgctcttg ggagggtctg tggctcttgg ttgagcgtct   33660
tcaccgcacc ctcatcctgg tgatgccgcg atgctccaac cccagagcgg acacttggcg   33720
tcggaattgc agggagtccc tccgctgtag aaagggctcc tcctcttcct tcccccatgc   33780
catcccagga gaaaggcctg ccgtggagtg ccgcttcctt tgtccccaga cagtccagcc   33840
taggaacctg tgccctgcac accctgtgaa tcttaaggga tggacccttc agtgcttttt   33900
cttcaggatg taattattga catccccatt cttttttttt ttttctgta taatttcaaa    33960 gtagcgagta tctgtcattg tctcgtctgc atgctttggt gcccagagag acagagggtg   34020
agctgactct catgtgagct gtggcaaagc ctgcgtaggc tggcgggtcg gctctgaggc   34080
cacgagtggt cattctcaaa ccccacagtg cttaaaatac cgcagcgagc agacgctctt   34140
aattacctgc agcattctcc attcattagt catagagggt cgcggtttct gttgtccgga   34200
aattggcaag tgagttaact tggttttctt agtcactttt catgtgaatc cttttaatat   34260
tctgttgggt gcaggttatt gcccttcaga aagtctaaag tcacagtaag ttgtatagtt   34320
```

```
ttattactat aaagttttct ctctgtcttt tctgtatcct acttctgttt tggttttct    34380
ctgcttcttc agaagtctta cagtgataca gtttaattta tagagtggtc agacatttaa   34440
aaaatttctt agtatgtaaa aggttaggga agcttttata tacttgaaca acagtccaag   34500
cacatgacta acttcatgaa cagatactga cttacatcat cttcataaca gccctttgag   34560
ggctgattat acctatttaa ttctaactga tcccatgtgg tgattttac cccatttac     34620
agatgggaga actgagtcac agataagaaa ttttcctgag gtcagctggg attcaaagcc   34680
agagctaatg ctcttaaccc tgtggctggc tgaagaaaat agcagaggaa aagaaaggtg   34740
ggactgtact gaaagtggaa acacaccgt tgtgtgggca gtgcctatga gtacacatta    34800
accagtgaaa tcattccttt ttttcctgac ctatttattg tgaacatttt ccagttcagg   34860
agtagagatt gtagcctagt aaaccccgta cccagtgcct ggctgcagct ccaggtcact   34920
gtgtgtggct tctgagcccc ctgcccctcg tgggtgtggc tgagaactgc ggtgcactct   34980
ccagcgctcc agtccctgtg ttgatgattt actgaaactt agggaagctg ttgtagtgta   35040
caagctgaga tggaaactgc ttttactaat actctcaaca aagtaagttc tgtaactttg   35100
gactttgagg aattataatt ttttaaagtt ttctttttgt gagacagtga aggaggtata   35160
ctttcattaa acttgtttat ataccagtag ttttcaatct ttttggtctt aggacccctt   35220
tgcactctta aaaattagag attccaaaga atccatgttt atgtgggtca catctatagg   35280
tatttaccat attatcgatt aaaactgagt ttttaaaaat tattttaaat gaatgttttc   35340
cattgtgtgc ccctggggtt tgtgtttgcc atgcagcgtt gttacagctg aagagagcta   35400
aagaccaaac tccaaaacaa aatctatccc aaccaattag aacatgaatt ctaagaagac   35460
aagaattcac ctaaaatcta aatttttttt ttttttttt tttttttttt ttggagacag   35520
agtcttgctc tgtcgcccag gctggagtgc agtggcgcaa tcacagctca ctgcaacctc   35580
cgcctcccgg gttcacgcca ttctcttgcc tcagcctccg gagtagctgc tgggctaca    35640
ggtgccggcc accacgcccg gctatttttt tatattttta gtagagacgt ggtttcaccg   35700
tgttagccag gatagtctcg atctcctgac ctcgtgatcc gcccgcctcg gcttcccaaa   35760
gtgctgggat tacaggcgtg agccactgcg cccagcccta aaatctaaat tctaaaatgc   35820
ccacagtctg tggcctttcc tgggttgtgc tgggattcca gtgtgtagcc gaaatcgaga   35880
agccttgata gtttcaattt ccttatgggt tctttatcta acatttaatt atgaggactt   35940
tgaaacacac ggtaaagttg aaaaagtttc acagtgagta cccttcacct agattagaca   36000
gttccatttt accgcataga tgcttttcaa cttacagtgg gggctgcaag ttgaaaatac   36060
cacaagttgc aatgcagtga atacaccaca cctgctacac atcatggctt agcctagcct   36120
accttaaatg tgctcagaac gcttgcatta gcctgcaggt gggcaaaatt atctaacaca   36180
cagcccactt catagtgaag ttttgactca tgtaatctat tgagtctgta ctgaaagtgg   36240
aaaacagaat ggttgtatgg gcgctcgaag cagttcctc tgaatgcatg ttgcttttgc    36300
actgttgtaa agtcgaaaaa tcgtcaactc cagccatctt cagtcaggga ccatctgtac   36360
ttactatttt taagctggtt gcctgtagca ttcctcagcc acggattctg atttgaaccc   36420
cagggcacag agaatcattt gagtgatggt tttctcaatt tccctgaaga aaatgtgatt   36480
agagacacag gaggagtcaa gttcttcatc gtagaagagc ttctgtagga cgctaggact   36540
ttgcgccctc tatgagcccc ccatttaaga gaagcaacag gaatgcacta cacatcttta   36600
ccttttcagg ctctactctg agttaatgtt gagccactcc atgtgacaca gaagcctctt   36660
gtcactgtgt tgttcattgg ggtgccgagg ccagctcatg gtatctcctg agagccagtc   36720
```

```
gttcactttc cagtattttt ttttgcgggg gcggggtttc actcttgttg    36780
cccaggctgg aacacaatgg cacgatctcg gttcaccaca acctccacct cctgggtca    36840 agtgattctc ctgcctcagc ctccctagca gctgggatta caggcatgtg ccaccacgcc    36900
tgcctaattt tgtatttta gtagagatgg ggtttctcca tgttggtcag gctggtcttg    36960
aattcccgac ctcaggtgat ctgcccgcct cggcctccca cagtgctggg attacagatg    37020
tgagccacgg cgctcggcct ccaggatttt ttaaagcccg ctgatgttgc attggtggct    37080
gatggtggca tgtcgtcagc cgtggcagag catttatgct tgtggatcg gcagatgaca    37140 cagatcaggg gccgccccgt cctcaccagt tgtcagccgt ttaccaggca tcatcagtgc    37200
agctctgccc tgtcctgtat gtgtacttgt cacatgggtc cagctacgtg tgctctgcac    37260
catgtaaaac agggctagga ttttgcatc tattctaaga aggaaaagg aaaagatga    37320 tagtctttta tattatccat actatttact attcccactg ctcttcattt tatcctgaaa    37380
attggaattt ccatctggtc tcatttcccg tcagcctgaa gaacttcctt tcacatttct    37440
ttcactgcag ttctgctgac agtggatttt agttttcatt tatctgaaaa tatctttgtt    37500
ttgccttcat tctggctaat tatggaattc ttcattgaga gttttttgtt taactttaac    37560
aatgtcattt tgctatattc tggctcttgt ttttctaaag aaaagtcctc tagcattttc    37620
gtcgctgtat gccgtgggcc atttttctct ggctgcgttg aggatgttgt ctttggttg    37680 gaatggtttg tctgtgatgt gccttggtgt aattttcttt tatttcattt cttgtttact    37740
gaactgcttg tttcagctta tgttttgcac tacaacagaa acttttcagc cagtattgaa    37800 gtattcttc ttcctcattc tcctcctctt ctccatctga gactccagtt ctcatgtatg    37860 agaaacctt ggtcttgtcc cacagatctg aggtgaagct cagttcattt ttcaaattct    37920
tctctctctc tccctcagat gggacatttt ctttttatct gtcttcaagc tcttgtaccc    37980
ttctgtcatt ttcagtctgc tggtacacca agctaatgga cgttttcata ccagatattg    38040 tattttagt ttcagaattt gtgtatggtt ctttttata atttctcttt ttctgctgag    38100
attctgtcca ttcatgtatt gtggggcattt ttgttttac atctttgaat gtcattataa    38160
tagctgcttt caaatcctgg tctgccagtt ccagcattgg ggtcacttag ggctggtgtc    38220
cattcatcgc gttttctctt gagtattcct cacatttccc tatttttatg aatgtctaat    38280
tctagattgt gccattgtgt gtgattatag agtttccagc ttttctcatg ttctgaagag    38340
tgttgtttct ctcttgcaac agggaatatt gtctggacaa ggtcgaggct tctgctggtg    38400
ggggcaggca gcagatggag gtgccttagt ccttagaccg caccagctgt gcgaagtcgg    38460
ccctccaccg tggctggggc agccaggtgt gtggcgggca cgtgcagagc ctgggctttg    38520
tctgggacgc tctccttggt gagcagctgc gctcatccca gccctatccc ctcttcccag    38580
ggctgggcac tgacggggga actgacaggg cccgccctcg ggtgaaaagc acaaacccgc    38640
accctcccat gttctgcggc cttcctccag gttctgcctg ctcccactac tctccagtga    38700
cttcagaggg gtgttttgtt ctgtaaatac attttttcc ccagaatcgt tctttgttat    38760
ttgtggaagg gttggtcctg taggagctgt tgccatgact gtggcccagc gggcccaggt    38820
catgccacct gccccctagtc gggctctgcg tgagcgctgc tcgctcccaa gcatggcttt    38880 gtccccagg agcaccccct tccttccagc aggtggcttt gctggaggtt gtcacaggtc    38940
agcgttccat cttccagctt gttcagaagc caatctgccc ctctatttcg cctcccctcc    39000
caggctgtgt ccactcctct gtcaagggag acgggtgctt ggcgtccccc tctgtattca    39060
```

```
gccttctctc ctttctcagg gcccccaagg tatctccact tgggcgtggg cacatgtgtg   39120
cacttgggcc acctgagccc tcctccctgt cacgtcacag ccacgctgct ggaaggcatg   39180
gggcttcgct gtttctttca gctgcaccac tcaccccagc ctcagcacct gcacctccct   39240
gaaactgctg tcacgagggg ggtcaccagg ggctcctcag ctgacaagca gggtaggtgc   39300
tttcagagct cactaccttt tcttggcatt tgtgactgcc ctgccccaaa ctccatcctc   39360
ccttggctgc ttctgttttt tttaaattgt gaaatgtcat ccctgtgcag ctggtgggct   39420
gcattaaatc ggtttcctga gaacacactt gcctggcttt cccttgcct ctctgtttcc   39480 tttgaaattc cctcttcttg tgtccctcaa aggctggtgg tcccgatagc gctcttctgt   39540
accctacttt acgctttgcc tgagccgtct tacccaagcc tgttctgcag ccactatccc   39600
tctcttggtg gctttcagct ctgagttcag ctgagaccct tacagactcc aagtcctcgt   39660
cagccactga taacgtgaat atttccaccc atgcagccag tgggtatgca gtcgcccacc   39720
cagcatggag ctgccagctc ctgcctgccc tcaacatggt tcccacattg gtgattgatc   39780
ccagcattcg agtgcttaga gcgaaacctg taagtccaag gtagctcctc tcccacatgt   39840
ggctttggcc ctgcaaggct atcattgttt cttccccctc atctaggcct ccatcttatc   39900
tgtcactttg tgggtccctc tgtctctggc cttgcccctc ttcagtctgt caagcaggga   39960
ccagtccagt acacactgcg tcactgcacg cccctgctta cggcttgtcc gtggtggctc   40020
aagaacgctg cagtcagccc acacttgccc agccccgtgc cgtgcaggga gagccgggat   40080
tccttttgct caggcgagga catgcggctt tgaggggtga ataactgcc caggctcgtg    40140 agctagaaag tatcacattt caaaccaaga catctgaatg cagcagacct gcaggatttc   40200
tttccgtgtt cactgtggtg tcaccagcca gggagctgct gcctctgtgt gaccttcttc   40260
cttccctgta tcagctcctg acgctcccct tccgctccaa tgacaacagc actgtcctgc   40320
tcctgggccc tgactgtagc atccctctgc ccagaatagg ccctgcccctt gaagcctagc   40380 acagcatcac ttctttgaac cttttcattt ttatatcact tatggctggc gctgcgctta   40440
gaacgtacta atgccgagca gaatgtttac cttaatatgt aaataagtga ctttcctaag   40500
gcccctaaat tcaaatgcca catcactaat cattacaaat ggaaatttgt ctgggcatgg   40560
tggctcacgc ctgtaatccc agcactttgg gaggctgagt tgggtggatc acctgaggtc   40620
aggagtttga ccagtctg atcaacatgg tgaaaccccg cttctacttg aaatacaaag    40680
attagctggg tgtggtagcc acgtgcctgt aatatcaggt gcttgggatg ctaaggcagg   40740
agagttgctt gaacccggga ggcgaaggtt gcagtgagct gggatcatgc cattgcattc   40800
cagcctgggc aacaagagaa aaactctatc tcaaaaaaaa aaaaaggct gggcgccatg    40860 tctcacgcct gtaatcccag cactttggga ggccgaggcg ggcggatcac ctgaggtcag   40920
gagtttgaga ccagcctggc taatgtggtg aaagcccatt tctactaaaa atacaaaaaa   40980
ttagccgggc atggtggcac gcacctgtaa tcccacctac tcgggaggct aaggcaggag   41040
aatcgcttga acccaggagg cagaggttgt tgtgaggcaa gatcgtgcca ttacgctcca   41100
gcttgggcaa caagagcgaa actccatctc aaaaaaaaga aaaggaaaag gtgttcactt   41160
cctgtttttg ctactttaaa aatattatca gaccatgcgc agtggctcac gcttgtaatc   41220
ccagcacttt gggaggccaa ggcaggcaga tcacttgagc tcaggagttc cacaccagcc   41280
tgggcaacat ggtgaaaatc cgtctctaca aaaaagatg gcacatgcct ataatcccag   41340
ctactcactc aggaggctga ggcaggagaa ctgcttgaac ctggcaggtg gaggttgcaa   41400
tgagccgaga tcatgccatt acactccagt ctgggcaaca ggagtgaaag cctctctcaa   41460
```

```
aaaaaaaaaa aaaaaaagaa tctattatca gctttatgtt ttcccaatta ctcactactt   41520
ttgtttctct ttgtgaagaa ctaacaaatg aaattaatgc aatgtagcta gataataaaa   41580
aaccaaagaa aaataaatta tatcatgttc ttaagtataa cattgcatgt cctaaaaaga   41640
tgtagggaag aaggagcagc ttaatcagtg tgatggtgaa tgttcaaatt ctaataacag   41700
ctacaagagg taatgcttct agaaattatc ccattaacat agacaagcaa atgaaagtga   41760
gaaagtcagt tgatatttta ggaaaattat tatttaactg caagtcttaa gaacacagtt   41820
ttccaatttt taaatgaaaa ctggcttttg gtaataacat tttaaagcag gaagtatcta   41880
cggtgtgatc gtggtacagc tcttagttca agtgtgaaga catttggttg tcttgtatat   41940
gacctagaag aagggcgtc tgctggaaaa caatgctgtt ctttttctct ttgtttttg    42000 agacagggtc ttactctgtt gcccaggctg cagtgcagtg cctcaatttt tcagttcagt   42060
gcagcctcga cctctggggc ttaagcaatc ctcctgcctc agcctcccca gtaactgaga   42120
ccacaggcac acaccaccac acccaggtaa ttttcatatt ttttgtagag acagggtttt   42180
gccatgttgg ccaggctggt cttgaactcc tgggctcaag ccatccaccc acctcggcct   42240
cccaaagtgc tgggatcaca gcgtgagcc cccatgccca gcttatcctg ggtcattttt    42300
taaactctcc cctctaccat aaataatatt ccctttactg tgatttttta agcataattt   42360
tgtaaattgt tgaagtggtt tctcattgtt gggaatgtag attaaaccac ttaataaaga   42420
taccttgaaa gcaaattaaa gaaagacatt tggcggaaaa ctactggttt tcttctgtag   42480
gtctctgttg acctaaagag aaagggattg gggtttgctc tcttggtggc gttgctgaat   42540 tggtcgggt ctgtcgctgc gcctctgcac ctgtgtgatt tgctgagtgc tcctctctcc    42600
tccctcgtga tcatggatgg agggcctagg agcccaggaa ccatggtgcc cttcccctg    42660 tgctgtgccc ctcacccttt cttccctgca tctatccctt tctacttctc ttcagagttt   42720
tagagatagg aacattaaag tgtgcccaat tgttttttatg aggttttgtt ctagagaaag  42780
gatgtaagga agcttgtaaa gacagaccac aacaggtttta agagatgcct ggggtgtgtt  42840
ggtcagctac agctgtgtaa cagccaacca gcagagctca ggagcaccca agatgagcgc   42900
cttcctcacg gatgtgtggg ttggctggtg tcagctgggc catgctccgt gactgttcag   42960
gccgtagtgg ctggggtggc tctgactcag gcgtccctca tcctccttga actggggacc   43020
aagggcacat gggagccatg aggattcgta aggccgagct tgggccggca cacggtcgct   43080
tctgcctctt tctgatgtcc gcagtgagtc ttatggccac agctccaaat tcaaggatag   43140
gaaagtctac actaccgtaa gccagctgca gcatgggttt cagtgtgacg aggggtaaag  43200
aactgtggca gagaattcag actactgcaa agtacacaga caagtcagag aacagaggct   43260 gatcttttg ataagcatcc tacttaggga aactccaatt aacattttgt gggaggctga    43320
ggggatattg catttgtcag atgaaagctg ggtgccatga aaaagaaaa catgaagacc    43380 aagagagagt tgttgggatg taaaagtgac caccagagca aaacattcag tagtgttcga   43440
ggattgccga atgtggagat acaaggtaga aggtgagtgg cgcaaatggg cagccaagct   43500
cagcctctga aatgcagggt ggctggaaga gaagatgaaa ggaaggagca tgttcagtac   43560
gcacgggaag aaaacggcct cgtgagtctt cacacgaaag gcagactga gtgctgagaa    43620 aggtgagttg aaaacaccca tgtcgagacg cattgttgtt tttttgata agggatcaag    43680 aaatgatctt acacgttttc aaaggagaac aacaaaacag atttcacctg tgaagaaacc   43740
agaatcaggc taacattgga cttgccattt gcaacagtgg atgccagagg actgtggcaa   43800
```

```
gccaagtttt gaatgaaagt tatttcatt cagaataaca aaatgtttca gattttggag    43860
cattttggat tttggatttt cagattagga atacagccta tataaggaaa tggaagacgt    43920
taatgattgt gaagattatc ttcctatgga agaatggtat gcattccaag cagtagatta    43980
cacatatatt aatgcaatta ggttttttc taccagcaga aaaagaaag gcagttaact     44040 ccagagcact catacctgct tgtacacaca gattgtccag ggatgtcatg attcaagtcg    44100
ccagtcatca gggaaatgca catcaaagcc acaggagag atcatttcta ttcaccgagg    44160
taatggaagt cagaaggaca gaatagcaaa tgttaggatc agaagcagct ggagctttca    44220
tccgcagctg atgggaggat taaatggtac aaccattaag aaaacaattt ggcatttctt    44280
atgaagtgat aaatgtatct tatattcctg cagttctcgt cctagggaat ttatcccaaa    44340
gaaatgaaag cgtacatcca acagcact tggagatgaa ggcttatagc agcttatgca    44400
taatagcccc aaactggaaa caacccagat gtccatgagt aggagaatgg ataaacaagc    44460
tgtggtatat ttatacaatg gaagagaact cagtcatttt caaagctaat acatgtaacc    44520
acatcggaat ctcaaaaata caatgttgaa tgaaagcagg gcccgtgtat ggtcctgttt    44580
atatgacgtt caagactttt tagagaattg aaaagcactg cgtcttgatt caaggattag    44640
tgatcacatg ggcatataaa tgtacccaaa ctcattgaat tgtacacttc agatctctgc    44700
attttgctct atgtaaattt cgcctcaaat taaaaaaaaa acacctgacc ccttgccgt    44760 ttcacacagg ccctttgcag tctggcaggt gtccaggctg cctgcttagt tccccctggc    44820
ccaaaatatg tgtgggtgga ggggtgaggt ctgtttcttc cgccatcttt aagaatatgt    44880
atgtgtctta taaggctctg ccccaaaaga gctttgccgg agtgtctttt cctagtctat    44940
tggcagaatt ctgtcttcct gttgagtctt agatgacgtt atatgtattt tgaatgtgaa    45000
aattctcatg tggtatttgt gttactaaat tgtcttctca tatagaatgt tggttgctg     45060 gccgggcacg gtggctcata cctgtaatcc cagcacttct tgaggccaag gcaggtggat    45120
cacctgaggt caggagttca agaccagcgt ggccaacatg gtgaaaccc cgtctctact     45180 aaaaatacaa aaaactagc caggcatggt ggtgtgtgcc tgtaatccca gcgactcggg    45240
aggctgagac aagagaattg cttgggaggt ggaggttgca gtgagccaag atcgcgtcac    45300
tgcactccag cctgggtggc agagcgaaac tctatctcaa aaaaaaaga aagtcagttt    45360 gctgacctca gctataaacc aaggaaagca aagccacttt ttcatcatct catttgctca    45420
aaaggtagag tttgttgtca gcatttccac tgacactctg attcaggagc tggcaaacgt    45480
tttctgtaaa gggccaggta attcatgttt ttgtgtttgt gggtcatgtg tagtctctgt    45540
ctcataattt tttttttt ttgagatgga gtctccctct gtcgcccagg ctggagtgcg    45600
gtggcgcaat ctcagctcac tgtaacctct gccttccagg ttcgagtgat tctctcacct    45660
cagcctcctg aatagctgag attacaggtg cgtgctacca ctcccagcta atttttgtat    45720
ttttagtaga cgagggttt tgccatgttg gccaggctgg tctcaaattt ctgacctcaa    45780
gtgatccacc caccttggtc tcccaaagtg ctgggattac aggcgtgagc caccgcaccc    45840
tgccaatttt ttttttaagt cttttttttt ttttttga gacggagttt tgctcttgtt    45900
gcccaggttg gagtgcaatg gcgcgatctt ggctcactac aacctctgcc tcccgggttt    45960
aagtgattct tctgccttag cctcccaaat agctgggact acaggcatgt gccaccgtgc    46020
ctggccaaaa ttgtttaaag tttaagaaaa atactgtcga tgtttggagt aaggagtacc    46080
taaaaatatt ttttaaatca attgggaaga tgataggacc tagaaaaata ggttgatttc    46140
caaacagcat gcgtaattag atggaatctt ctttaattaa aaaattagtt ttccctcaac    46200
```

```
aatcattatt taatttgctt tattttaaaa tttggcatca aaagagacac tacaaccctg   46260
ttctggaaaa atgtttgtga tatgctgtgg ttttgccctg gtcttcagtt cttggccaga   46320
tggtcagcat gtgtgtttct caggtcggcg cgtcatcaca tagtcgtagc ggctgagccc   46380
acacgccgtg gcttgaggga ctatctggta ataaaatatc aaaggaaact tcaaaggaac   46440
atctgatcac atggtggcct gttaaaacct ataccaagta attcctgaag atttggaaga   46500
atggattatg atccttcaca gtaaaaacaa aatacaggaa gataacacag caatcataat   46560
taacagaaag aaagaaattc aacctctcca atgaaaaaaa taagcactga cagacaatgc   46620 cttcttctg atggtacaca ctgagggaat agatctgcgt cttttaaaaat ggttcatttt    46680 aggccaggtg cagtggctca cgcctgtaat cgcagcactt tgggaggctg aggtgggtgg   46740
atcatgaggt caagagatcg agaccatcct ggtcaacatg gtgaaacccc gtttctacta   46800
aaaatacaaa aattagctgg gcgtggtaga gcacacctgt agtcccagct gcttcggagg   46860
ctgaggcagg agaattgctt gaacctggga ggcagaggtt gcagtgagct gatatcacac   46920
cgctgcactc cagcctggtg acacagcaag actctgtctc aaaaaaaaaa aaaaagttta   46980
ttttgaaaaa caaaatcaca aatttataga aaagttgtca ctacaatata aagaactttc   47040
ctgaaacatt gggagtgaat tgtggatctg atcccccaac atccccaaat cgtgatcatg   47100
tgttttctgc aaacaataag tactgccatc aagatcagga agttggcatt gagatgtcac   47160
caccctctaa ttctcaggct tactcccatt ccggccattg tcccagtaat gccttttata   47220
cccagaggat caagttcgga atcccagggt gcatttggcc tcctttgtat ccttcagtag   47280
ctgctcctcc atcttccctt gtctttcatg acccggatac tttagaagat tatgaaccac   47340
tgattctgcc aaccatccca caatctgggt tgtttgata cttctcctga ctagattcag    47400
gctgtacatc tttgccagga acatgctacg ctgctctcac tgtgtcctgt cgggtggtac   47460
aagctctcaa tttgttccgt tactgatgac agtcactata ttaattttca tgctatctgc   47520
caggattctc ctgtgtaaaa attactttct aactagataa atagtctgtt tcttatcaga   47580
ctttcagctt aatcatttat ttaagtttgt atgggattat tgtttcctgt tttattcagt   47640
gagttataat ccattaatgt cgttactctg atgttgaagc tgtaccagat ttggctggtg   47700
ggagcccctg aaaactgatg ttttgtgtct ttttaatatg tcctgtcatt ctatgagcaa   47760
ttccttgctt tctgacataa caagatgttc aacactcagc tttctttccc ctagccctga   47820
aatcaacaat ttccaacggc ctaggttcat ttagtgggaa atgggtttta gaagccaaaa   47880
tctgatgctg tgtgtgccct gctgatggag tgtggctgct ctaggccttc tcagtgacag   47940
tctagctcca cagggccgtt tctgtgtttt tccttttctt tctttctttt ttttttttt    48000 tttttttctg tgatagagtc tcactctgtc acccaggctg cagtgcagtg gcacagtctt   48060
ggctcactgt aatctccgcc tcccaggttc aagtgattct catgcctcag cctcctgagg   48120
agctgggact acaggcatgg ccatcacac ctagttaatt tttgtatttt tagtagagat     48180
tgggtttccc cattttggcc aggctggtct tgaactcctg gtctcaagtg atctgcctgc   48240
ctcagcctcc caaagtgctg ggattatagg catgagctgc agctcctggc ttttttggtt   48300 tttgttttg agatagtatc tcactctgtc acccaggcta gagtgcagtg gtgtgatccc    48360
tgctcattgc atccttgaac tcctgggctc aagggatccc ccagccttgg cctcccgagt   48420
agctggggct acaggtgtgt accaccacac ccagctaatt ttttaaattt ttagtagaaa   48480
tggggtctcg ccatgttgcc caggctagtc tctaacttct cagctcaggc agttcttctg   48540
```

```
ccttggcctc ccaaagtgct gggattacag gtgtgagccc ccatgcctgg ccactgtcag    48600
catcttttaa atttactgat cccaactcag ctgacttacc tggtagcaaa taaaaggctc    48660
acttgacaat tcctgcattg ataaaaagct gcccacttaa aaaaaatagg tttcttggaa    48720
gcagcagtgt tttctcattg aatcttttgt agagccatca gtgacccag tctgcctgga     48780 gcccacttac cagtgccggt ggaaggtgga aacccgacca ccatccaggc ctctgccctt    48840
ccggtcacag ttgtcttagg aattctatcc gcaggcatcg aaagctgctt gggaccgcgt    48900
taatgatttt tgttttcaac catcaaacct attttgaaca actcaaaagc ggaatagact    48960
gcttttatat tacccagata tttcacattt ctcttgcttt tctttccttc ctgatggtcc    49020
aagtttgctt cccgttcatt ttccttctgt tcaaagaact ttagcagttc tttcagagca    49080
ggcccgctga caaacagtcc tctcagtttt ccttcatctg agggtgtctt atttcacctt    49140
gactggatgt agagttacag ttggtagtta tttgccttta gtactttaaa atatgattct    49200
actttcttct ggccttcatg gtttctgatg cgaaagtccc agtcatttga atggttttct    49260
cctatgaggt aatgtattgt ttttgattgc tttcaagatt ttttgtctt tagttttag     49320 cattgtgctt atgacgtgtg tgggtgttga tttctttggg cttatcttgt ttggataagc    49380
tcattgagct tcttatgcat aggcttatgt ctctcacaca atttgggact ttttcagcca    49440
ttgtcccacc gctaaagttt taattttttt ttctgtaaat tttcatttgg ttctttacac    49500
ctggatttgt gcaggctttc tgtctgtctg tgcatctcag gagtgtttgc ccctccctgt    49560
tggggcattg tgccagtagc tgcttctgtg tctttggtag ttctagcatc tgtgccatct    49620
cagtgttggg atctgttgat tttcttgaat agtatgatac gagactctga ctcatcttta    49680
atcctacaga gaatgttgat gcttttggtt tggtgcagtt gacctggttg ggttctgaca    49740
gcaagtactg tgcagcctttc tgtggggtgt ggctgtggtg ccagctccat tttccgagct   49800
gtggcggtgc tgtttggcct cgtcctttgg gggcattgct tgccgtccag cctcagactc    49860
tgctggaggt gtgttcggca gttcagattc ttccatgtgc agcccccggg tgaacgcacc    49920
cacaacgcca cggggttgct tccctgaaat cttccctctc tgctatcctt ctgtacttcc    49980
agttcccagg ggctccccttt tttggtcctc cagccagaaa gctggggctt tagccctctc    50040
tgctgtgcac ttcagtgacc atccccatct tcatgggaag acagagagaa gaaaaggcag    50100
tgaggaggtg tcaccccacc tggaatcgca gcccccacat cagagaggag cgtctccctt    50160 ccagggggctt tcgttgctgc tccgtcttac ctggaaccag agtcccccaa cactacgttt    50220
tcatagatca tctttagttc agtttccctg aaacacaggt tggcccccaaa aaagtaagag   50280 gaaagctgta acaactttat aagagtgcct ttttaatgcg ctagaatatg tggctatta    50340 ttgatgaatt attttaatc tcagagttgt cgattgtacc tttaagaaaa acatattttc    50400
ctacaataaa gccctaatt ttatttgcta aaatcagagt tctagttcag attttgtttt     50460
gtgttcttac tctggaggca caaatggagt aacaccagta tgtttatgtt ggagaggagt    50520
tttgtgttgc ctttcaaact tgaatccaat agaactacag acttaaacaa taaatatgaa    50580
tgggagataa ggaaaatcaa agacaaaaaa aagaaatgg acttaataaa agattttgt     50640 acataaatac ttcttctgac cccaagacaa aaccggaaaa gatgaagcat attaagataa    50700
tgtaggtgac tctattagta atcagcttga gtatttatat gaaggtgtat gggaggccgg    50760
gcatggtggc tcacgcctgt aatcccagca ctttgggagg ccgaggcggg cggatcacga    50820
ggtcgggaga tcgagaccat cctggctaac acggtgaaac ccagtgtcta ctaaaaatac    50880
aaaaaattag ctgggcgtgg tggcgggcgc ctgtagtccc agctacttgg gaggctgagg    50940
```

```
cgtgaacccg ggaggcggag cttgcagtga gccgagatgg cgccgctgca ctccagcctg   51000
ggtgacagag cgaaactcta tctccaaaaa aaaaaaaaaa actttatggg aacagtcgca   51060
tatgtataat agcagataga agactgatgt tagagagtat ttctatgctt tcatctgaaa   51120
atgaagggca gggctgggcg tgaaggtgca ggcctgtaag cccagtactt tgggaggcca   51180
aggcaggcag atcacttgag tccaggagtt ccagagcaag cagcctgggt gacatggcga   51240
aaccccgtgt ctacaaaaaa aaaatacaaa atcggctgg gcatggtgat gcatgcctgt   51300
agagccagct actcaggagg ctgaggtggg tggatcactt ggacccagga ggtcgaggct   51360
gcagtgagcc aagatcacac cactgcactt cagcctgggc gacagagtga gaccctgtca   51420 aaagaaaat gaagggtatt ttgttgtgag gaatcagttt atgcatagtc tgggatgtgg   51480 ccagtgaccct ctggatactt ccctgtttgg tgccttcctg aaacatgtta caaattctgt   51540
tttataaaat gcctgatctc tctgtctaaa actttagaat cagctgggca cggtggctca   51600
tgcctgtaat cccagcactt tgggaggcca aggtgggtgg atcacttgag gttaggagtt   51660
cgagaccagc ctgaccaata tgtcgaaacc ctgtctctac aaaaatgca aaaattagcc   51720 aggcgtggtg gtgtgcgcct gtaatcccag ctactcagga ggctgaggca caagaatcgc   51780
ttgaactcag gagatggagg ttgcagtgag ctgagattgc accactgcac tccagactgg   51840
gcgacagagc aaaactctta tcttaaaaaa aaaaaaaatt gtaaacataa agcatactg   51900 tcgcatgcat ttcagtcagt gaattcaaag tgcatgttag gccgggcaca gcggctttca   51960
cctgtagtct tggctgcgta gaaagctgag gcaggaggat tgctggagcc ctggagttcg   52020
agcgcagcct gggtaacata ggcaggcccc atctctaaaa taaataaact tttaaaaatg   52080
cttgttagca gcataaaatt gtgtgggaaa atgtttggtt cgttttaatt aaaggatgta   52140
gagagctgct ggtagacagc aaaatactta acaactattg tgctgattgt cctgtggttt   52200
gatttaccaa cctagtcatt gtagaattag atatataaga tacagaattg atgtggttac   52260
ctgtattttg actttgtaac attttaatca tcctctaaga tcttgtttgt ttaaaatgta   52320
tgtggttttt taatgtaact tgtaagatgt gtttatttc tatggatatc tcatagttat   52380
acctacatct tttgggttgg aggtgtatgt gatattttga tatatgtata taatgtgtaa   52440
tgatcaaatc agagtgaggt gtctatctca agatttaatc ttttattttt ttaatttata   52500
ggaatatcat aggttttga ttcagctttg ctttactttg gaaatcgcac ttggtcatta   52560
aggcagaatg ccaagggga gactgcttag caaagtgagg agtaagaact tgtggccagg   52620
cacagtggct cacgcctgta atcccagcac tttgggaggc cgaggcgggt gaatcacaag   52680
gtcaggagat tgaggccagc ctggtcaaca tagtgcaacc cccatctcta ctaaaaatac   52740
aaaaattagc tgggcatggt ggtgcgtgcc tgtagtccca gctgctcagg aggctgaggc   52800
aggagaatca cttgaacctc ggaggcagag gttgcagtga actgagatca tgccactcca   52860
gcctggcgac agagcaagac tccctctaaa aaagaaaaa aaaaaaga acttgtatga   52920 gggtcgtcct cccaggcctt ttggaatcct ataaagaaga ttccataatc catacgcagg   52980
gcacttcaga aaggaaactt ggtaatgttc gtggcttgtc ttagcttgtg taaatagcaa   53040
tatagtggta aatttagctc ctaggattct gagtcccta taatccagaa atacatctta   53100
actaaataat acggtctgct cattagtaac aaaggtgagg caggacactt cacctctgga   53160
gccataggct ccatggagat aaatcagttg catttcaggg actccactgt agggccctct   53220
gctgttcctc tgtagcggga ggaagaccgg ggcagtgccg acggtgggcc cgggcctcct   53280
```

```
gtgaatgccc caagcaggag gaagaccggg ggcagtgctg accgtgggcc caggcctcgt    53340
gtgaatgccc cagcagggcc ctttatttct tggggatttt atatctttat acttattagg    53400
accatttcct gttttattc atatttgatt acaaactatt ggcccttta agctactatc      53460 cccattaaac aaatgaggaa gcagacacaa aactgacctt agttactcaa tgaatattcg    53520
aactcaggtc ttgggaggca tcattccgtc tccttcccgt gtgtcattaa ctgtgagttg    53580
ctactggctg gaagactttc tctgtatcta aaaaagtaaa cacattgccc acaaaactaa    53640
catgctgctt tttattggtc atagttttat tgaaagagcc ctttaagact tggctgcaga    53700
gtttcataat atcattcttg tacatgcata gaaaggaaaa tatccaaata aatgaggtga    53760
ggtgctcctg cagttgacac acagagtcca gcccccgtgc acgccgtcca gccggctggg    53820
tcggggcgtg cattcctcct gtgcagtggg ctctgtgtgc cacgcagtgc tgcggtacca    53880
cagcattgga gcgcgtgccc ggttgctgtt ttggagtttc tcctaagcta ctgtacccgc    53940
tttgtgggtg ggttgctggg ttttcctca ttttctccat aggtggcagg ctgtcacaac     54000
catgttattc ctgccacatg gccagcagca ggtgtgagat ggtcctggca tctgattgta    54060
gaggcactga agtgtaaaag gaaaaaatca gaagctgtac accttggcat cgaaacaccg    54120
tggtgtggtg cagttggacc aaagggaggc ctgactttgg acatcaccat tcttattcca    54180
gcttccctcc ctttttcagt tgctacgtta gagtactggt ttctaaatgt aggtgttgat    54240
tcaattataa aatgatagtc gatgtgaata tacattttat cgaaggctgt gtgatctaac    54300
ttgtaagact tgaggaaaat gcctgttgtg tacctggaat gagaaaagaa gaaaggtttg    54360
aacagacaaa catttcaaag ggaaaagtat atcatccttc gtgttcttac ttcaggaggg    54420
cgcaggcctg gcccagcctc gggtcccttt gccccagccg tgtttgtccc cacacaggcc    54480
tgcctgggtg cggtgctgac cagcctcagt gctccagcag agcctcctca tggccttggc    54540
tgccacgcgc tgtggccgaa tcgccatttt tacgcacgtg aatgctttcc tcacggaggc    54600
tttctggcca gcgcggatcc tgtctttgtg gtccctctgg ctctgctctc tcaggtgatg    54660
gggtgatgtt tgcccctgaa ttttttttt tttttttttt tttttttga gatggaattt      54720 cactcttgtt gcccaggctg gagtgcaatg gcgcaaatct cagctcactg ccacctctgc    54780 ctcctgggt caagtgattc tcctgcctca gcctcccaag taactgtgat tacaggcatg     54840
agccaccacg cccggctaat tttgtatttt tactagagac ggagtttctc catgttggtc    54900
aggctggtct ctaactcctg acctcaggtg atccacctgc ctcagcctcc caaagtgctg    54960
ggattacagg tgtgagctcc cggccgcccc tgaatttatc taggcatttg cttacgctcc    55020
acagaaggca gtggggctga ccagggaggg aggggaaggc ggccacactg ggggcagact    55080
ggaagtgggg tgtaatgagt gtctgcgtgc agataggtat tcgctttgag atggcaaaac    55140
cacattacag aaatgtgggg aaaagctact cttcacttcg ccaccgtaca cagctgttcc    55200
catcactttc gatcgtttag ttttagtgtt ttcatttcca tttaaacaa aactgtcatc      55260 atgttatgca tagaatttgt aattttccag ttaatatccg aggcttttt cttttttct       55320 tttaagttct ggggtacgtg tgcaggatgt gcaggttgtt acataggtaa atgtgtgcca    55380
tgatgtgttc ctgcacccat cagcccatca cttaggcgta agcccggcat gtgtgagcta    55440
tttatcctgc tgctctatca gcctttttc ttgttgtggt ttttcgaatc acagcgtcta     55500
atggctgcag agttgagagc gtgctgaaat cttcctgac cttgactcag gctggtcacc      55560 cagccccgc actagcccgg cccctcactc cttgtgcctg gtcttccctc tctcccaggc     55620
tcctcttctc agccttcaga gcccgcggag cacatgggt ccagggcagg agtagaggga     55680
```

```
gcctcgctgc gtcgctcctg ggcccggagg tgccctggcg gggggccgcc actgcccagg     55740
ctagccattc tgcagaggga tgcgccaaca tttggagcct agaattggaa atgcctcttt     55800
tatttgaaaa cagctgaata acattcatct gcttttccc attttcctgt ccagatatga      55860
aatatgactg agtcacttcc tactctcagt ccagatgggg tttttttcct tttacttttt    55920
tcataaaccc taatattatt cagtcctggg acatgaggta cacatggtgt ttgtggccag     55980
ggagaatgct gactacatgt ttctgtattc attgacacta tatgttgttt aaaaaagtaa     56040
aatacatgga ttagagtgat gtcattgtgg gaagttttag aagtactgct ttagaaaaac     56100
ataaaagcta tgtatttgct gacagtctga ctgaggaagt caggcaggaa cagcgtgtag     56160
ttccactaag tgaacatcag cagggctgtg tagcctctaa atgtgctgtg ctctttgttt     56220
tgccagaaag gaaataaaca tttgtatttt ttatagtaat tccttcctgt gaggtgctat     56280
tttaagctta aagaactcta aagcgagtgg actcccgcat ccgtgagatg cacgaggttc     56340
cctggaggag caggtggtgc cgctgggagc gcagcgcccg ctgcctcgtg ctccacgacc     56400
ctcacagcac ctgcagggtg acctgggacg tggccgggtg tttgcagcac acgctgggga     56460
gcgagcgagg atggttggtt cagcgcaggg ttggctggct cattctgcag atacaggag      56520 tcagtgtcgt tggctccagg agcagggtgg tgtctggcac agctcctcag ccatggtatc     56580
acggggtggc cacagaggac atgcagatga ggggcatgtg gaggcccaca gagctgctca     56640
cggacgggcg ggtgttggtt tagacagcgc tgtctgggag cacaccgccc agcgtggcag     56700
ccactagcct cccatggctg cagaaccctc agcgtggttc ttcaggacaa ctggggttg      56760 aacgtttaat tttattcctt cttaattaac ttaacttgcc acgggtgatt tgggcagtgc     56820
aggcttagaa ccatccccag agcgtgtgca cagagcaggt ccttgctcta ggagaggttc     56880
gtgtatgtta ggagaagaag ttgccaaaaa atgtggggaa tcgtttaaaa aattataatg     56940
tactgtagga cttgtcagag tccttaatat cctaatgtac attgacagtt tacaaggagt     57000
ttctgagatt tttttttccc aaaaaacgtc tttttttttt tttttttttt ttttgaggc     57060 gaagtctcac tttgttgccc aggctggagt gcaatggcgc gatatcggct cactgcaacc     57120
tccgcctccc aggttcaagc aattctcctg cctcagcctc ccgagtagct gggattacag     57180
gtgtccgcca ctacacccag ctaatttttt gtcttttcag tagagacagg gattcaccat     57240
gttggccagg ctgctctcga actcctgacc ttgtgatttg cctgcctcgg ccccccaaag     57300
tgctgggata ccaggcgtga gccactgctc ccaaccaccc caaaaaactt tttggccata     57360
cggttttttg aggtggccgt gaccttgtgt gagcactggc gcccgtggag agggctctgg     57420
agaacggtgg tgcaggagac caggcggtct ttgggtgcct gcaggaagtg tcacattcac     57480
agttctgaga agttgtgttg agtatttcac gttggacaaa gttagattct acaaattagc     57540
agacatcccc gtcgcacgcg gccaggtggc ctccagaccc agcgaaggct ggtggaggaa     57600
ggagggagaa tgctcccgta gcctctttcc cagttatgtg taaagctcgg cgtgggctc     57660 ctggcgcctg ggaagtgtgg aagctggcag agccgggtgt gttgggcagt gagaaacttc     57720
agcgctggat cagcggggca ggcctgcctt gatgaggctg agtcagaaac tacagcatgt     57780
tcgatacgcg gctgttttat tttgagcaga tatttgggc catttaaaaa tagtgcttaa     57840
aacctaattg tatcatctta ttttgatga gaaaaacacg caccagtgta cgtggaaaac      57900
gggatgagta ggctgatgcc ttccgggctc cctggtgagg ccgctcatcc ctctggctgt     57960
ccatcccgtg cagcttcatt cactgcagcc cggctctgct cccagacggt gctatcttcc     58020
```

```
tgactccccc aggactgttg ttctggtctc ctcatccttg ccctcgcaga gaaggatgag   58080
aatgaattct cctgaaaaga aaggccaggc acggtggctt tcgcctgtaa atccagcacg   58140 tgggaggct  gaggcgggcg gatcacctga ggtcaggagt ttgagaccaa cttggccaac   58200
atggcaaaac cccatctctt ctaaaagtac aaaaatcagc caggcacggt ggtgcatgcg   58260
cctgtaatcc cagctactgg ggaggccgag gcacgagaat cgcttgaacc caggaggcag   58320
aggttgcagt gagccgccga gacagagtga gactccgtct caaaaaaaaa agaaaaaaga   58380
agaaaataca tagaagagac cccccaggtg actgtgttct tggggaaata ttgtcttaaa   58440
cagtcacagt tgaaaatgct gagcattacc ttttcagaag ttgggacaga ttcgtaacgg   58500
ttttgagggt gaacccggga ggctgcacag attctcagtt gtagctactg ctgggctctc   58560
actgggtcca taaacgtgtg tctgtactcc agtgccgttc ctgcccttcc attgccaggt   58620
gtggctttgc tttcctcct  ttctgttgtg aatctgccct gcattggtgc tgccgcccgc   58680
cttcctctct gggctctggt tctaggtgag atgccaccaa agtgacagga cagccttggg   58740
tgctgagaac ctggttttga aaactgctga atatcaaatg ctaaataatc atgtatatac   58800
ttcaagctct tatttcattt ttgtttttg  tttactttt  acagtgagtg ttgaaaagat   58860
agacctgaag ggattatcac acacaaaaaa tgacagaaat gttgaatgtt cctttgaggt   58920
aagatgctaa gttttttcc  cctctctcct ggaaggctag gaagaaaaca cttaccctgg   58980
agatgctttt ccttcctagc taaggctgtg ccttgtgcaa agccccgtgc cagtgctgta   59040
taggaagctg gccctgagct cggggtgggc tgtctccagg gtgggggttg ttggctgggg   59100
ggcctctgca ggcgggaagg gtgggggctc ggcagggcc  tggggttgtc agttcaggtg   59160
tgaatggtgc atacctcagg gggctaaata gcagaactgg atgaggcagc ctgcggagca   59220
gcgcacacag aacccggggc cgtggtgcct ctggagactg atgatgaaag ctccttggtc   59280
tgggcaggga acgctcctta aactgacacg ttcagatgct gggagctggt cactgaagtt   59340
gggtaccaca agaatcagg  agagaggagc agtattgtgt ttcccggtga cccacggtga   59400
ccagggtcga gatggccaga agcccatttc cctctcacag cagggcgtgc aggaggccac   59460
cccgttccct ggacgctgta ccccatcaga acctgagggt gcccttaggg gtacaggccc   59520
cctctggcta ctctgtgcca tccctaggat gtggccctct gctcccggcc caaggtgcta   59580
gccagggcac cagtcctcac gcgttcatcc tgggcagcag gaggaagaaa ggcaggcttg   59640
aaatctttct cttaaggaac attcctgaaa gcagcctcta gacacttcac ttatattttg   59700
ttggccagat ttaatttctt ggtcccacct agatgcctaa aaggctggga aatgtgtccc   59760
ggctgatggt gccgagctcc cagtcagggc tctgtcagga accctgacag ggggacattc   59820
tccttggacc acatgtgcat cgagtgctga ctgctcttga aggtcggttc ccagcgtcat   59880
tggagagtgc tctccagaca gaactcctgt gagcatctgg catgactcat ctgtgcagct   59940
tactaatttt ttgaagagtg tagctacaca aaaatacttc aaatcctttt tccactaaag   60000
ggacaagtct ccacttggtt tgggagactg tgttgtgaca agcagttgtt acgctgtgcg   60060
tttttcattt gaaaatgtaa ggaaaatcct cagctgctga ggtttggagg ttgctggtgc   60120
ctgtgatggt agtgccggag tctcggccgcc acggagttt  ctgggtctca tgtcgtgcag   60180
cccaggcgga gcccagggaa agaccacagg ggccctctga gtgccctgga acccagcagc   60240
ggtcccagtg atcctaggta tttgctgaca ttttgcagtg gtcgcgtgtg acaccttcct   60300
tcattccttg cattgcggtg tcaggcctct tcagatactg gtggggactg tgcacttaag   60360
aaggtgctgt gcacggagct gtcttcgcat atggtcatag cacagtgggc tttgatttgc   60420
```

```
tcccaatcct tagtccagtt agtccagtta tttgtggtga ggaaatcagg agtcaggtcc  60480
acacagtgta aggtgtgaga acttcataca acctgaccgg ccatagcttt gctttacttt  60540
tctcttttct tttcttttt tttttttttt tttcagacag agccttgctc tgtcgcccag  60600
gctggagtgc agtgacgcga tctcggctca ctgtaagctc cgcctccgg gttcacacca  60660 ttttcctgcc tcagcctcct gagtagctgg gactacaggt gcccgccacc atgcccagct  60720
aattttttgt attttagta gagacggggt ttcaccatgt tagccaggat ggtctcaatg  60780
tcctgacctc ctgatccacc cgcctcggcc tcccaaagtg ctgggattac aggcgtgagc  60840
cactgtacct ggccttttct tttcttttcc tttcctttct catttctttt ctttttctt  60900 tctttttttt gacactgtct tgctctgtca ccaggctgga gtgcagtagc atgatcttgg  60960
ttcactacag cctcgatctc ctgggcttaa gcagtcccct caccttagcc tcctagtagc  61020
tgggaccaca ggcacatgcc accatacccca gctaattttt tgtacttttg tggagatagg  61080
gtttcaccgt gttgttcagg ctggtctcaa actcccctgc tcaagcgatc tgcccgcctc  61140
agcctcccaa agtgctggga ttacaggcat gagtgcacct ggccagattt tctatttta  61200 gaaatcaagt tgattctgaa agttagcggg gcacagtggc tcacacctgt aatcccagca  61260
ctttgggagg ccaaggtggg tggatcactt ggggtcagga gttcaagacc agcctagcca  61320
acatggtgaa accctgactc tactaaaaat acaaaaatta gccgggcgcg gtggcgggca  61380
cccgtagtcc cagctactcg ggaggctgag gccggggaat cgcttgaacc tgggaggcag  61440
aggttgcagt gagccgagat tgtaccactg cactccagcc tgggcaacag agcgagactg  61500
catctcaaaa aaaaaaaaa agaaagaaat caagttaaag tgatatggaa agaacttgag  61560
taattaattt tgaaagaag aaacgaattg gaagacttgc acaacctgat ttcaagcctt  61620
ctcgaacagc aggatcacaa cgctgtgagg tagcaaaagg gaaggcagca cagatgagtg  61680
ggacagaaga ggctccagac agactcacac gcacaggccg ggtatgaagg agtgccacaa  61740
agaaaggatg cgcttttcag cagacaccct ggaacagacg tccgtatgca ggagaagcaa  61800
gccttgactc ccgccgctgc ccttacacca aattaactca gaagtgatcg gagacctaaa  61860
tgtaaaccca aaacaaaaac tactgggagg aaacacactt tgtgatttta aactaggtga  61920
agatttctga gatacggtgc tgaaaacatc cataaaagac aacatcgatg aattagaata  61980
tattaagatt tgaaactttc tctttgagag atgctatgaa gagaatgaaa aggcaaagat  62040
taggagaaaa tatttgcaag tcatgtagct gatgaaggat ttatatgttc aaaatgtata  62100
aagaattctc aaaactttt tttaagagat ggggtctccg gctgggcgcg gtggctcacg  62160
cctgtaatgc cagcactttg ggagcccaag gcggacggat cacctgaggt caggagtttg  62220
agaccagcct agccaagatg gcaaaccct ctctctagta aaatagaaa attagccag  62280 gcgtggtagc tggtacctgt aatcctagct gcttgggagg ctgaggcagg agaattgctt  62340
gaagccagga ggcggaggtt gcagtgagcc aagatcatgc cactgcactc cagcttgggc  62400
aacaaaagca aaactgcctg ggaaaaaaaa agagatagtg tctccttctg tcacccagac  62460
tggtcttgaa ctcttgcctc aagggatcct cctgtcctgg ccgcctaggt tgctggcatg  62520
agccgccatg cccaacaagt tgctgcttct tactaagttt tgagagttct gccaggtgta  62580
gtggcacatg cctgcagttc cagctactcg ggaggctgag gcaggaatat cccttgaggc  62640
caggagttca agactagcct gggcaacagt gagaccctgt ctccacaaag aaaaaaaaag  62700
atgatttgcc aaggaagata catgggtggc acataaacac atgtgaaaag atagtcacca  62760
```

```
tcctcatcat taggaaaatg ctaagtcaac cacagtgaaa gggcactgca cacctcttga   62820
aatactggaa tgaaaaacgc cggccccacc cacctcaggc tgcggtgtgg gggagctaga   62880
atcacattca ctgatggtgg gaatgtgaaa tggtgcagct atttcggaaa acagtctggc   62940
agtttcttaa aaagtatgac ccgtaagttc cagcctaggt atttaccctg ggggaattaa   63000
gcacatgttc ataaaagatt catgcatgag tgtttatagc agctttgttt gtaacgttcc   63060
aagactgtca acaacgaaga cacccgttca caggcgcgtg gacaggccaa ccctggtgtt   63120
atgtccacgc agtggaatac caccccggc agtaatgctg aggggtctca gaatggacaa    63180
ctgagatact cagccatatg cacgaatctc gtgttgtgtg aaagaaacta gacgactcct   63240
tccaaaaagt ttatactcag tgagtccgtt tatgagtcta gttatataaa attctagaaa   63300
atgcagactc atctgtagca acagaaagca gtcagtggtt tcctggggag gggctggagg   63360
acacctcagg ggtgatgctc cctgccatgg tggggcatgg ctcacaggtg ccctcagatc   63420
agaacagcag atggacccct ttaaatacgt gcagttcatc gtcagttata attcattaca   63480
actccttttg ttaaaaaaaa atacttgaag attcaaattt tccttttgtc catagaacct   63540
tgactaatga aaatcaaatt gtcctttaag taagttgtcc tttgtaagtg gaaataaata   63600
gcaattatac tgtgaccaga gcaataagcc agcattcgta ggaatgcctg ctgtgctttg   63660
ctgaggtgga acagtctgtt gccgacagta tggcaagatt caaagaaacg ttttttttcta  63720 aaaactttca cttattcagg gagaaataag taacttctcc ctgccccact gattttctca   63780
gcctgtttct cgttttaatt tttatgtatc gttgttttcc aggatacaaa aggttactgt   63840
tttataggaa gatataagta actggattaa gatgacttca agcttttttt ctatggagtt   63900
ggttttgatt ttgctgaaat tataatcgct agttcctcgt tgctgaggaa atcaaaccaa   63960
tatgcaggaa tcaaatgatg gaaccttttt gatataaagt cagcatgtag gcagctgagg   64020
caggagcatc acctggaggc caggagactg tgactagcct gggcaacaca gtgagacctg   64080
tctcttaaaa aaaaaaaaaa aaaaaatcat agaggccagg tgcagtggct catgcctgta   64140
aatcccagca ctgtgggagg ctgaggcaga cggatcgctt gagccagcct gggtgacatg   64200
gtgaaacccc atcactgcaa aaagtgcaaa agtacaaaa agtagttggt cattgtggca    64260
ctcacctata ttcccagcta ctgaggaggc tgaggtggga ggatcacttg agcctgggag   64320
gtcaaggctg cagtgagcca agatcatgcc actgcactcc aacttgggcg acagtgagag   64380
accttgtctc aaaaagaaa aaaatgata aaacaatact aataaacaac tcttattaaa      64440
ccatccttta aagtcaccca gacgttattt tagtgttatc ttttctttca aagtttattt   64500
tttcacttgg gtggctgaag cacaaggatc gcttaaaccc gggaggcgga ggttggttgc   64560
agtgagctga gatcgcgcca ctgcactcca gcctgggcag cagagcaaaa ctctgtctca   64620 aaagaaaaa aaagttcata ccccaagcaa cactgactgc tccgagtacg ctgtcagtca    64680
ctgttagcaa agaaggagtc ctggcaagtg aggcttccct gagtctctgt ttttatcacg   64740
tgtacacctg cacagcagag ggcccagtga ttcctcaggc attgccagag cagcaggcac   64800
taggtagacc ctgccctcca aggttggggg acctgtggtg atgagtgtgg ctgcagaagg   64860
tgacccgtgg cagagctgag tggagattct gggtgtcttc atgtctcacc cagtatccaa   64920
cactgtttcc actggagctg ttttgtgttt gtttgctgat tgacaaggac ttagaaagct   64980
gctccttccc ccacatcttc ccctgttggc tggagctcct ctggcgtgca cgcgagcccg   65040
cgtcccgtcg ggttttgct ctgctctgtg gacggctgcc tcgtcttcct gcctttagtt    65100
gagcgtttca ttcctactgg cctggttttc atttcagaga actcttgggc tctgacagtt   65160
```

```
gtttttcat agcatcctgt tctcggatat gccttcttct cttagcttag taagaatatt   65220
gatgaaaatt tttagttttt cttagagtcc acgctttccc ttggctgctg tgttctcctt   65280
gctggctttg cctgtctctg tgctgggcct tggctctcct caggggtctc caaaggtctg   65340
ggggatcctg ggctgcctgt ccccttaggg gtgtggctga gccctgcccc cagaggtgcc   65400
tggctgagcc ttttcttgtg cagaatgagg ccgcatggct ccagtggctc tggagggga   65460
ggctgtgtgg aaaaacactg atgttcagag ccagtccaca gtgagccgga ggaactagac   65520
cctgcgtgtg aggacatcct gagcatgcac gggctgtgtg cacattgggc tttggggtgt   65580
gatgaagatg cattacaatt cgtccagata aggctaagta gcttttcagg gacgtgatag   65640
aagatgctgt gccagaatct aattggcaac acttttcttt ggtgaaatgt aaagtaatgg   65700
ggtagctggt tgtggatgct tgtgagtatg gttggacacg tgtccccata gtacgggtca   65760
ggcaggtatg acaagaggat gctcttcccg cccccatgcc cctctaacgg ccggttcccc   65820
ttctggctct ctggggcaag tcggcaggtg aggtagaggg cttggctggg tctggatcgt   65880
ggctgctgca gcttagccat cagccagcat cacctgcaga gcgagcgaca tgggctggtc   65940
tccgcctgac tgtgcggtct ctgttttccag tgctcacttt ctgatagcct tagggaggaa   66000
tgtgagctgc acctgcaagt cagagaaaaa tgtatccgaa cacaaagtag aagagtcctg   66060
tgtaattaaa gtgcataact gttggaaaag cagattgtct gtttcaacat aagatgatct   66120
gtccatacca tgtttaatcg ctgggtggt ggatttcaca tcttccctgg gttagggcgc   66180
agtaggaaag atacagccta gaggcaggtg tgagagctgt gcagaggaga cgttttctat   66240
gacacgcttt accttgaaag agacacgctg tcagcagcgc gggggacagc catcttcacg   66300
gcaggggttt gtgtctgttg gtggtggtgt tcttggagtt ctgtgtgggg agcagcttag   66360
gaacctctcc ccaagatttt tggtgttgag agatttttaat atttaaggca gagaaggagc   66420
tcaaacattt tcttttcttt tcttttcttt ctttctttct ttttttttt tgatagagtt   66480
tcgctcttgt tgcccaggct ggagtgcaat ggcgcgatct cggctcactg cagcctcccc   66540
ctcccgggtt caagcagttc tcccacctca gtctcccaag tagctaggat tacaggcgcc   66600
tgccaccatg cccggccaat tttgtatttt tagtagagac ggggtttctc cacgttggtc   66660
aggctggtct tgaactcctg acctcaggtg atccgcccac ctcagcctcc caaagtgctg   66720
ggattacagg tgtgagccac tgcgcccggc ctcaagcatt tcattttag gtgtggaaga   66780
ttctgggtgg caaggtgcac gccttgcagc cgttagttcc agggacgctg ctgcttgcct   66840
tgatgaattc tggtaggcac tggggttctg gtgaagaaga ggtggccctt tcctcgactg   66900
gcctgtgtat tatgagggcg tgatgaaaca gacccaggag tgacgctacg tgatgtgacg   66960
agactggcct cagtttcagc aggcaggagg gtggacacct cggggactag actgcaggcc   67020
catggatgtg ggtgtgggtg tgggtgaggg agcagaggtg gtttgggtgc ctgtgagctc   67080
tctttgctct aaatcagtgt taatacacgc ttttcttttg cataatgtat ttggtcattt   67140
tatttgccga cttgaaatcc cccagcttct tgtggacttg agtgcaattt gcatttggtg   67200
cttgtccctt cctgacctgg cctcctccct gtcatttcag gccatcccct ctgtccatct   67260
caatcctgta gctaacttct tatttgcctt tcagaagtca acccaagctc ttctccatgc   67320
agaaactccc tctaatgtgc aaaaagtacg ctctccttcc ccctcagtca gctttgttta   67380
gcacctcatg tgacgagcat tgtgatagcc agggagagc tgagcaaaaa gacaccgccc   67440
cttccccct ggagcttagc gtgcatgtgg ggagatggac ctccgtggag ccatgcagtg   67500
```

-continued

```
acaccgcccg ctgctgcatg ctgggaagga aagctgatgc tcacaagggc tgggcacacc   67560
agacgttgca gaatctcctc cagaaagccc ttttcactgc tcttccccag cagtgatcac   67620
tgctgcccta gtgatcactg ccctgtcctg ttgctatcaa tggactcaca ctgtccccac   67680
agctctgcag tgtcctgaga gcagggcctg ggctcactgt gtgcccacag cacctgggcg   67740
ggcgcaccac gggcccttac cggtggtcga agggctgctc tctgggaatg tgtcgctctt   67800
gcatctgagg cacataggct cacttaagaa gaggaggtcc cctgaggaag ttgaacaggg   67860
cacacacaag caattgtcag ggattttcta gaacttacag gaggcagctg tagacccac    67920 tctggagtaa tttggtgata tctgaataat tgcataaaac aagttagact ttagagggcc   67980
tggagctatg tgactcttct ttctgtaaca agtcaaggga tgcttaggtg cttcccacag   68040
caggtgcacg gcccactggg ctcagctgcc gactgaacgt gtgccccagt cgtaccagga   68100
cacgtgctgg gaaccaagta tgtggtgtct gtttctaagg tttgtttgtt tgtttgtttt   68160
taaggtcttg tggtctgatt cttcaataac atcagtaacc aaatcttcct ctgaagtgac   68220
ggaatttatt tcaaaggtaa ggtaatcaag ggctcttata aaaattaaaa gaatcacatt   68280
ccccagtggc tgatgatacc acggagtaat ttcagaggcc actcccttca gctagcgagt   68340
gagcgtgcgc agggcggggc ctcctgccca gccacagtgg agtcccaggc ccgctgctga   68400
catgagcgtt gctgcgagca caggtccgtg accccgcgga tgcctccttc acttgttgag   68460
actgagatga ggctgagaga tgcgccgggc atgagcgact gatgaggaca tttggtttct   68520
tttgttactt ttcagtcccc caggtttcct tggcaaaggc tgggggagag aggcatgctc   68580
aggtggctga gtgggtagag acttcaccta gttctacctt tatctgtttt tatttattta   68640 tttatttat tattatttt ttaagagact ggatcttgct ctcgcccagg ctgggttgtg    68700
gtggtaccat catcacagct cactgcagcc ttgacctcct ggtgctcaag tggtcctccc   68760
acgtttatct ttacaaatat ctggttcagc agataccatt gaacagaaag ttccactact   68820
aaataaatgc ctctttgcct ccgtgtgcat gtgtacacac agttgtaact gcacacgtgt   68880
ttagggccca ctggcctgtg ctgtagcgtg aacgactgtc tcagccaaag tgatgcctct   68940
caggcagtca gctttgtgaa tgggataaca tatgtaaatg tctccaaaga gagccttact   69000
tttcattata aagccaaggc ctcatcctgc aggagaacat ggagtgagga cgatgtctga   69060
ttacacttat cttttggcc tcttgggcat tgaagaacac gacagtgcca cgccttcgag    69120
ggtaacacac accccccccc gggaatctgc ttttccctct gtagtgttta aaatactaaa   69180
tctcctcgcc tctgtgtgta gtttcccctt ttgttaaaca cagcttccct ggactccact   69240
cctgccggct ggaacttcga cctctcattg gcttttgtc tcagtgtttt gttttgtttt    69300
tttttttctt gagatggagt ctcactctgt tgtccagact ggagtgcagt ggtatgatct   69360
tggctcactg caacctccac ctcccggctt caagcaattc tcctgcctta gtctcccaag   69420
ttgctgggat cacaggtgca caccaccacg cccagctctc tctctttttt ttttttttaa   69480
tttttagtag agacagtttc accatgttgg ccaggctgct cttgaactcc tgacctcagg   69540
tgatctgtcc tcctcggcct cccagagtac tggtgttaca ggtgtgagcc actgcacctg   69600
gcctaatttt ggaaaattct tatccatttt ctccctcaag catttcttctg ccgcatcctc   69660 ccctctcctg gactctggcg gcacgagcct cagacccctg gtgctgccgc cccacggctc   69720
tcccatgctt gtgcatttct ctgtgtgtac gtctgggtgg ttcctgtgcc cgttccaca    69780 ccagccgatc ccctcagttc tgcccaggct gctgtgagc ctgtccatgt actcaagtcc    69840
tcatttctgc tgccaggggt ttcttttgtg ttttgcccc taggttttcc atttgacgtg    69900
```

```
ttcatgaagt ttccatctct ctgctgaaac gtgttcatga agttcccgc ttgtttgtgc      69960 atattgtcgt tttcactagg tcctttagta catccatcat agctgtttaa agtccctgtc     70020
actaggtccc acatctgagt tatttctgaa tctggttcta atgattgctt tatctcttga     70080
caatagtttt ttccccttt attccttttt tttttggtat gtcttgcaaa tgttgactga      70140
atgtcagaca tgtttagatg accgtggagc cggaggagag cgagatttat gcctggaaag     70200
ggtcaacacc tcttctgcca gggcccttag tggggtcctg gaggccatct gggcaggatg     70260
aagctggcac tgggctctct tgctgcctct gttaccctca gggcctctcc agtgaaggca     70320
gctgctgcct gagtctggag ggtcttctcc gccgttttgc ttcactccca gctttcagcc     70380
gtccctgcag gcctgtggca cacagcaggg cactctctac cctctcggcc ccttttcggg     70440
ggtagaccgc tgctgcttgt ttgcgacctg gtgctgggct tgtgggggca agggccttca     70500
ctcttgcagc ccagcctgat cctgggcagg cctgtgtgcc tgggcttcgg ggtggcactt     70560
cctcagtgcc ttgccctccc cggcaggagc tgacctcctc cagcaccaga gcgcttttgc     70620 tttttcccctt cttccaggag cagcgggtct tcttgtgact ggtggcagag aagggaagt    70680 attgtccctg ccccactcct aaaaaccggg cctttggttt gggctctggg gccaggagca    70740 attttgtcc ctcctgcaac gtcttaaggg cttttcctca gatccagaga gtggtcccgg     70800
gaattgcact aggcctggtg cccggtcccc aggtgccacc gatggggctc tctctggctc     70860
ctcctgcgga aaggaacttg gaaagaaggg cccacttgcc ccgcctgggg ctccggcatt     70920
tctgttggcc acgtcagcct gtggcagtgt gtccatcgga acctgtctct ccagacctgc     70980
tggtgtggca gccaccaggg ccttgtgccc tggcttgtca tgggagcagg tcccgtttga     71040
aattaagttg acttagtggc ccagcaactc tcagatgggc tcaaggaaca ttgtgattgt     71100
gcagattgtc aagcttttcc ggatgtaact gtgagagcga tgttcttttg tgactttcta     71160
caccctaagt ggatgtgggc cccagaatag ctctgacggg aggtgtaaat catatcagac     71220
cagcaggcgg caccatggag cacctgcccc aggttttcct gcagtagcag aattctgctg     71280
gtgttggatg ggtctggaca cacctcctct accttgtcct ctcttccagc tatgtcagct     71340
ctatcctgaa gagaacttgg agaaactcat tccttgctta gctggtccgg acgcatttta     71400
tgtggagcga aaccacgtgg atctggactc aggcctgagg tgaggccctt accaggcacc     71460
cggcgcgtcc acagctggca aggacaggct ggtcctgtgg tcaatgctgt ggtcctccaa     71520
ggagctctgg gaggatgcgc ggtcacctgg acctgggtct ctacttggcc tctagggatt     71580
tccattagtt ctggaggatt cgggagcccc cagtaagctg agagtggttc tgagtgtgtg     71640
aggaagggaa ttccagggtg ggtcccacca cgtcttgggc tttggcagtc ctgtgaaata     71700
atcctgggct gctgtttcca tcctgtagtc caaggttgag actattccca gataaaattg     71760
gcgtctctta aacagtttct ctggaccctc gatcgtgtct tggctcacgt ggcacacgaa     71820
gtaacatggc cgaccagttc cgtaaatgtg ctgctgccgg ggccctgggg accagtgtcc     71880
aagcaccttt ctggctggtg ggtggcactg atctcatgtc acagggcatg actgctgtcg     71940
tcaaccttgg tggccatgaa tacagcattg agaggaaggg cttgaagaag cagtggcagt     72000
cgggcaagaa ctcagttgaa ttaaagcagg aagaatatga ggctctggca cttctggctt     72060
ttttcctcta atacacattt ctcttgatta aaagttaaat ttttttcttt caattcgtca     72120
gcaggaatgc catttaatg ttgataagac cacttgtttg ccttttaggt acctggcctc      72180
attaccttct cacgtgttga aaaatgacca tgtcaggagg tttctcagca cttcctctcc     72240
```

```
cccacagcag cttcagagtc caagtgagtt tgtaaaatat ggttaaatat aaattaaaaa    72300
aaaaaaaaac agctgggcgc agtggctcat gcttgtaatc ccagcacttt gggaggctga    72360
ggcgggcgga tcacctgagg ttgggagttc aagaccagcc tgaccaacat ggaaaaaccc    72420
tgtctctact aaaaatacaa aattaggctg gcgcagtgg ctcacgccta taatcccaat    72480
actttgggag gctgaggcgg gtggatcacg aggtcaggag ttcaagacca gcccggccaa    72540
tatggtgaaa ccccgtgtct actaaaaata caaaaaatt agccaggcgt ggtgatgcat    72600
gcctgcagtc cccgctactt gggaggctga ggcagaagaa tcacttgaac ccgggaggcg    72660
gtggttgcag tgagccgaga ttgcaccact gcactccagc atggttgaca gagcaagtct    72720
ccatctccaa aataaaataa aaatacaaaa ttagccgggc gtggtggcag gctcctgtaa    72780
tcccagctac tcagtaggct gaggcaggag aatcacttga acccgggagg cggtggttgc    72840
agtgagccga gattgcccca ctgcactcca gcatggttga cagagcaaga ctccatctcc    72900
aaaataaaat aaaaatataa aattagccgg gcgtggtggc agtcgcctgt agtcccagct    72960
actcgggagg ctgaggcagg agaatcactt gaacccggga ggcagaggtt gcagtgagcc    73020
gagatcgcac cattgctctc cagcctgggc aacaagagca aaacaccgtc tcaaaaaata    73080 ataaataaa acaaatattt tcattgtctg taaattttta tggtatttat ttttaaattt    73140
ataggtcctg gcaatccctc cctttctaaa gtaggtaccg tgatgggcgt gtctggaagg    73200
tgagaaatct tctatgtaac cagcacagtt cagataagca ttttacaatg tttactttga    73260
gttctgtgta aagttgttcc aagaattaag tcatgctcaa gttgagtctt ggatgatatt    73320
gagaagaatt gagtagagat gattgaattt acgatttcca aaaaagagt tctctaagcc    73380 actggaatca gaattcccag ggactcctcc ccagtgcaag gtcctgggcc ccatcataga    73440
cgtagaaagt cagaatttcc gagaatctgg ctgtgagaaa cctgctccca gaagcatagg    73500
gtcgtgctcc tgaggagcgt cctctgtccg cacgggccct gggtagctgc agtcgtatgc    73560
cggcaacaca gaggctccca tctttgctga cagtgaggtg ggctgtcaca gatcagtgca    73620 cacgcaccc catagggagt ctcgtggaga tgttgtctgg gcgcgaggtt tcgaggcgta    73680
gactggcatc ctcctggtgt cggggtaggg taagcgccca gtcagcaggt gtgactttgc    73740
agttaaggag caaggccaga gtggagtgcc ggtcacacct tccagccttc tgcgttttac    73800
ttttctagaa aaattgtatt tgaacattaa agatttaata gtctattttg atgtatgatt    73860
tatcagtgtc attctgtgac ttagaagtaa cagaaatacc tatcggagta gcatgttttt    73920
aaaaaataca agtaacagaa acttggcagc taaagcagaa gtctggtggg acagagacg    73980 tacacataca taatacacat acgtacacac aagtagacgc atactccgaa gcacgggcag    74040
aggcatgtgt gtgtatatgc acagccgcct gtatgcacac gtgtgcacag acatgcatta    74100
cagaaatctt agctgcagaa aggtggttgg ggagggaggg cagtcatagc acagcagtgt    74160
tggcagttca gggtggcctg tgacaacagg gccggccaag aggcagaggc tggcacagaa    74220
aggcctggaa gtgaggtctg tggtggagtc tgtggttgtg gaagccacag tctctctgtg    74280
tccctcctgc ccctgtccca caggcctgtg tgtggagtgg ctggtatccc gtcctcgcag    74340
agcggagccc agcaccacgg gcagcacccg gccggctccg ccgcccctt gcctcactgc    74400 tcccatgcgg gcagcgcggg ctcagccctg gcctaccgga cccagatgga cacatcacct    74460
gccatcctca tgccttccag tctgcagacc cctcagaccc aggagcagaa tgggattcta    74520
gactggctta ggaaactgcg tttgcacaag tattaccccg tctttaagca gctctccatg    74580
gagaaggtat gtcggttttc tggctggccg tacagaattg ctagattgtt tactcaagac    74640
```

```
ctccctgggg gcattgagtt tccaaaccaa cacaaggtgg atgaagtacg gaggccgagg    74700
cgcagcgcct gttcttaagg gagacggtgg gctttgcgga ggccgcctgc agctgcagcc    74760
agccacaaac aggacatgtt gtaaacaaac agcttgtcta ggggcttcaa gaccttcaca    74820
aactagatgc tctgcgtgac gggagggaca gtccgtcccc agagccctgc tgtggacaga    74880
aatcctgagc tctggcacgg tgcccctttt agacatttct cggcgtagct ggcgcagaca    74940
ctgcggcggg ccagatctag aggaatgggt gcattttaca tcttccaagc agtcgtacct    75000
agagaattct tatgaggaac attttttcac tgttaaaaaa attcagaaat ttcttaagtc    75060
ttgatgtcag tgataaaact agattaaacc catacaaggt atttgagctc tggactccct    75120
ctgctgggca aaccggcttg gtggctttta tctatgtaaa aatttcattt ctcgaaaaat    75180
ctacaattga acctagaaat caagctttta ctacatagtt aaatccaaat tgtaagtata    75240
tttgtaatac cctttgttta ggatttgtga atgttttttt cttttttga gatggagagt    75300 cttgcactgc cacctgggct ggagtgcaat ggtatggtct cggctccctg caacctctgc    75360
ctcccgggtt caagcgattc tcctgcctca gcctcctgaa tagctgggat tacaggtgcc    75420
caccagcata cctggctaat attttgtatt tttagtagaa tcagggtttc cctatgttgg    75480
ccaggctagt ctcgaactcc tgactcatga tctgcccacc tcggtctccc aaagtgctgg    75540
gattacaggc atgagccacc gcgcctggcc aaggatttgt gaatcttaaa aagcagagat    75600
tttactaacc ttgttcataa ttagttttaa atgttttatt cttacgtttg cattgagatg    75660
gcctaaatca caaatcatgt taggaaataa catgaaaatt agaggctggt gtgtttgcgt    75720
agcaccagcc tacacaatgg agtagccaca caaccattca gcgtggatgg catctgcttt    75780
tctgcatcac ttgctacctg acaaagttgc tgtcatccct ggccaggtgc ggtggctcac    75840
gcctgtaatc ccagcacttt gggaggccga ggcaggtgga tcatctgagg tcaggagttg    75900
aagaccagcc tggccaagat ggtgaaaccc cgtctctact aaaaatacaa aaattagctg    75960
ggcatggtgg tgggtgcctg taatcccagc tactcgggag gctgaggcag agaattactt    76020
gaacccggga ggtggaggtt gcagtgagcc gagatcgcac cactgcactc cagcctaggt    76080
gacagagtga aactccgtct caaaaaacaa aaaacaaac aaacaaaaac aaaataagag    76140
cgagattttt gtctcaaaaa aaggaagaaa aagacgacca tcccgcagag ggtgatgagt    76200
tctgaaggga tggcactgtg atgggccgt cctggggagg gtgggggtgg cacgctatca    76260
taacttgcat ctccacggtg attcaaactg tgacttatgc aagacgtttt ctttagtcac    76320
ctgccccaaa gcatgtacct gctggtattt actcacagag cagagggcaa gtgggcacct    76380
ttggcagagc cgccagcctg tgaggtggtg cacccatcca cacagcctgc acagaaggtg    76440
ccctggagga gccggggaca ctcttgctca gaactgcgtc tcggagttga accgttgaca    76500
ccaagtcatt tagcaagtaa agggtctagg atttcccagc ttgtaattgc tgagttcagc    76560
tggatctgtt tgcatatccc agaggcagaa taaatgtact gaattcaact ccaagttctt    76620
tgttctcaga gtcctactta tgtctccgta actttgtaat ttgttttttc tgtgaaagtt    76680
tttgagcctt actgaagaag atctgaataa atttgagtct cttaccatgg gggcaaagaa    76740
gaagctcaag acccagctgg agctggaaaa gtgagtgtga agtgggtttt gaaacctgtg    76800 tttattttcca tttctcgtgt gccgaatgga gtgctgaggc ttccagtgct aaatactagt    76860
gattggatta gttcctgttg cttatccagt ccttagccat gcttttatt atttttattt    76920 atttattttt tgagacggat tattttttatt tatttatttt ttgagacgga gtctcgctct    76980
```

```
gtcgtgccca ggctggagtg cagtggtgca atctcggctc actgcaacct ctgcctctca    77040
ggttcaagcg attctcctgc ctcagtctcc caagtacctg ggattacagg cacccgccac    77100
cacgcctggc taatttttg tatttttaga agagaccggg ttttaccata ttggccaagc    77160
tgatctcaaa ctctggacct caggcgatct gcccgcctgg gcctcccaaa gtgctgggat    77220
tacaggcctg agccaccgcg cctggcctag tcatgctttt aaagttctac aaatgtgtct    77280
taggtttgac aggaaaggac ctttatagta aatttgacca atcagaatga gttccttgcc    77340
ttaatgctct gggggggaatt tccctgtggt gtggagtaga cccatctcga agtcgccctg    77400
tatcaaagcc gccctgtggt gtggagtaga cccgtcttga agccgcatgt gaggcagcac    77460
cagtaggcag tgctcacttg ttcctgtgct tgattatttc acaggagaa gtcagagaga    77520 cggtgcctga acccctcggc cccgccgctg gtcaccagca gtggtgtggc tcgagtgccc    77580
cccaccagcc acgtcgggcc cgtgcagtcg ggcgggggca gccatgcagc aggtgaacaa    77640
gggtgtgtcg ggcagatggg ttactcatac acagagaggg cccgtgtgtc gggcagatgg    77700
gttactcata cacagagagg gcccgtgtgt cgggcagatg ggttactcgt acacagagag    77760
ggcccgtgtg ccgggcaggt gggttactcg tacacagaga gggccggtgt gccgggcagg    77820
tgggttactc gtacacagag agggcccgtg tgccgggcag gtgggttact cgtacacaga    77880
gagggcccgt gtgccgggca ggtgggttac tcgtacacag agagggccgg tgtgccgggc    77940
aggtcggtta cgcagacaca gagagggcct tgtgttctgt ttgatcatta gatttcaaat    78000
cacacctatt tgatttttac attttaaat ctttatactc attttccatt aactattata    78060
gtctctgcca taagaaaatc gaagggacag ttggcttagg agctagaggg cagtcacctc    78120
cctgaagttg cttgggcaaa atgatcaggt ccagaaactg ccacagtgag agcgagcgcg    78180
tgggggtgag cagaaatgag atgggagtag cctgcgccca ccccccaccc caggactggt    78240
gcccagaggc cacgttttaa gtcagtgcct ttaatgttga cccatcagtg acatggttct    78300
ccatggacct tcctgctttg ggggacccctc agtctcagcg atttggtttt catcctcccc    78360
tctcagaaag ggcgggacac ctggcgcgct tgctccgttg tctcacaaga ggagccgggt    78420
tttcttcaca atagaaatcg gaggagcagt agctcaggag ggaaaaaaa aaacctggca    78480 ggatggattt taagtggtga tttgactgaa aagatctccg tgactcggcc ggcctcgtga    78540 gatgggggtgc ggtgtagtgt tgtgatagtt cctgggggtg cgctgggggt gcccttcaca    78600
gggcattgtt ctggggttga tggcgggggc cggcagggcc ctggctgagc gggtgttgag    78660
catcgctgcc atttgaatct ctgctgcatc cgtcaccgtg cggcctgggc cggcgtgttc    78720
gttttctgac tctcagagcc ctgcgtttcc ctggaaggag cacctgccga cagtgcgatg    78780
caggggcacg gggcgggctg agcctgcagg ggcgctagtt gatggctgct cctctgtccc    78840
ttttctgcag agctgcgggt ggaagtggag cagccccatc accagctgcc ccgggaaggc    78900
agttcctcgg agtactccag ctcctcctcc agcccatgg gggtacaggc ccgggaagag    78960
agctccgaca gcgctgagga gaatgacaga cgtaagggca cgtgcgcggc gctggctcga    79020
cctggcccag ctgtggaatg gcactgacca ctcttgtttc cctctctagg tgtggagatt    79080
cacttggaga gctctgacaa ggagaagccg gtgatgctgc tgaatcactt cacttccagt    79140
tccgccagac ccacggccca ggttctccct gtgcagaatg aggccagctc caatccatca    79200
ggccaccacc ccctgccccc gcagatgctg agcgcagcct cacacatcac acccatccgc    79260
atgctgaatt ccgtgcacaa gccggaaaga gggagcgcgg acatgaagct cctctcgtct    79320
tctgtgcact cactttttgtc tctagaagaa aggaataaag gatctggacc aagaagcagc    79380
```

```
atgaaagtgg acaagagctt tggcagcgcc atgatggacg tgctgcccgc gtccgcaccc    79440
caccagcctg tgcaggtcct ctctgggctt tcggagagca gctccatgtc acccacagtc    79500
tcctttggtc cccggaccaa agtcgtgcat gcatccacgc tggacagggt gctgaagaca    79560
gcacagcaac cggccctggt cgtggagacc agcacggccg ccacggggac gcccagcaca    79620
gtcctccacg ccgcccgtcc gcccatcaaa ctgctgctgt cgtcatctgt tcctgctgat    79680
tctgccattt ctgggcaaac ttcctgtcct aataatgtgc aaataagtgt gcccctgca    79740 ataataaacc cccggactgc tctgtacaca gccaacacca agttgccctt ttctgcaatg    79800
agcagtatgc cagtgggccc cctgcagggt ggcttctgtg caaacagcaa cactgcctct    79860
cccagcagcc acccctccac gtcctttgcc aacatggcca cgttgcccag ctgcccagcc    79920
cccagctcca gcccggcgct gtcctccgtc cctgaaagca gtttctatag cagcagtggc    79980
ggtggcggct ccacaggaaa cattcctgcc tcgaatccga accaccacca ccaccaccac    80040
catcagcagc cccggcacc cccgcagccc gccccacccc cgccaggctg cattgtgtgc    80100
acgtcctgtg gctgcagcgg cagctgcggc tcgagtggcc tgactgtcag ctacgccaac    80160
tacttccagc acccgttctc cggtccgtcc gtgttcacct tccccttctt gcccttcagt    80220
cccatgtgca gcagcggcta cgtcagcgcc cagcagtacg gcggcggctc caccttcccc    80280
gtcgtgcacg ccccttacag cagcagcggg accccagacc ctgtcctgag tgggcagtcc    80340
acgtttgccg tgccacccat gcagaacttc atggcaggga cagcaggggt gtaccagacc    80400
caaggactgg tgggcagtag caatggttcc agtcacaaaa agagcgggaa cctatcttgt    80460
tacaactgcg gggccactgg tcaccgcgcc caggactgca aacagccgtc catggacttc    80520
aaccggccag gtaagcgcgc gccatggccg cgcccaccag gctcccgcag gaccagtgca    80580
cacaaatgct tggtttttat gaagagtaaa cttctttctt tgtaaagcaa ataattttc    80640 gaatgctctt tgaaagcgcg tggaaatctt catgataggc cgtgaggtcc ccagaaggac    80700
tgctgttggg tctaaaacgg ccatgatgat ttcagacagc ctctggttct agaaggtgct    80760
tagccagtgt ggacagggcc tccctggact gccgtgtcct gattcgagcc cagagaggca    80820
cgtgtgaggg attcagtgct gcccctggc ttaacactgg ggccctcagg ctgtggcgca    80880
tcggcattcc ggaccctctg gggtggggct cgctgtcccc tctgccctc cctgccggcg    80940 cggctgtggg tgtggggc tgtcacccct cagccatgct gcatcttccg ttccctcctg    81000
ttttatctcc gctatttttt tgtctccttt agtcaaatcc cagtggatgt ctgatgtagt    81060
tgtaataggg ttcttcttgc tgtctgtttt ggaaacgggg gactgggaag gtgggtccca    81120
actctgacaa ctcatggtgc caccttgcca aagtcacttg atctctgcag acttccagtt    81180
gcttctaagg gttgcactag atctgtgatt ctcagacctg cctgtaacat cacgttcacc    81240
tggagagttt ttagaaacac gcctgctgac tcagcaggcc tgcaggcaag gtgggttgac    81300
aggcgctctg ccatgcgggc ccgggtgggc ctgtgcctcc cttcataaag ctggctgcat    81360
ctccagaggc acggggcact caccagcgct cacctgccct cacccagtga aggacgcat    81420 gttagagcag cccgcctgac gtgtgcagag cctgactccc agaggaagct cccaaagaaa    81480
aagatggtga acttttcctg agtcatttca ccccggtcag atttgataaa cttgtaaaat    81540
taggtcccat tttgcagggg caggaaggga gtagaaacgg tcaggatggg tggcctagat    81600
ttccagcacc agaatcttgc ccagtggctc tggacatgac tggacagatt ggtgttggt    81660 ggtgattcta cagtcattca aatttgacct cttttttccc ctctctctag gtacttttag    81720
```

-continued

```
gttgaaatac gcccctccag cagaaagtct ggactccaca gattgatatt tttctctggc    81780
aacagaacgt tattaagcca tggagacata aggaaaatta atacaaaac tgagaagtct     81840 agttgctgtt gagcttaatc tttttaatcc aaaggtgctt tacttttcct agactggata   81900
gaaaatctag cgtagaagtg catcaaactc gatttattgc caaaaccctg gattggagct    81960
tggtgtcaga actcgcctag tgggcatctc tgtggctggt gagatcggcc acctccactt   82020
ttggttgcag tgcagagacg ccatgtctcc cgaagagcat tgccatcact ggccctccta   82080
ggctcacacg tcaattccag ggcagctaca cgtggtctga atcgagaacc gagcttggag   82140
ttctccaagt ggagttccac ccgccggact cctgacaccc ctgggctagg aaaatgtcg    82200 actttgtttt gttctgttcc taaagtgatt agcactaatc tctgggattt ttaaggattg   82260
cactacagaa gaatgtaccc tgatgtaaat ctctgcggtt ctgggagcca aactcctctg   82320
agaacagtca gtgcaagaga ctccaataat ccatattgaa agagtcagca ccagcagagg    82380
ctactcgact taggacgcaa cagaggtttt agtatttcct tccctcctcc aagcacttgt    82440
agcagtttca ggttttaat tttttctgc aaataaatct aaactacgtt attaaataga     82500
aatagtttac tcgcaacaac ttaatttcta agggtccaag tcccagagaa tccatagtcg   82560
tcaaagcttt gagagtatct ttcttcccag ccagtcagtg gctttgagcc ctatcttcca   82620
ctacaaatga cctctcgagg ggggacggcg acagcgcggc tctgtgagtg gctgtgagga    82680
tgctgcacgt cctcagcaga gtttgcaagt tgctttatct cccacgggct ccccaagaac    82740
ctccaacccc gaggcttatc gctagcggat tcacacctga gacagacatt caacaatga    82800 tacagtcctg tcatttatca gcaaaagatt gggaattttc tcctgtcaac ttcttttgta   82860
ttaggctgtg tattgatagt taattccgtt aaaaattact tggaaaacag tgggaagtgg   82920
taggactctg gaagaggcca cacacccgag agctgcgaga tctgtgcaag tctggttttg   82980
gttaggtagt aataaaagtc ctcactgtag atctctaaat ttcaacccac ggaaatgaaa   83040
gccttttgtc tgaaatttac ggacttaaat cttcaaggtt aaaggaatt tctgctcaa     83100 ataatactct tatcgaaaat gctaaagtct tcaatgttaa aatactgatt ggtaaaatct    83160
tgcagttggg attttgcagt tggatatta ttttaaaaaa aattataata ttcagactat     83220
tcttaaaatg ggacaatcag cctcatgaaa aattgatgta aatcagaaga atacccctaga   83280 atgaggcctt gtgatgtgag cgttcaattt gaagagcagt tcctaacttc atagaaacta    83340
aagcagaaag ttgttacatt ttttttatga caggctttta gtagaatttt ttagttttat   83400
tttagttgaa ttttatttct atgcaatgca gaattaacag acctcttctc ctcatggtac    83460
acagtattac agtgttgaag taatggtgat gcttattaca acagctattt aggggaatgt    83520
tacgttgatc tcttaaattg taaacactac aaaatgtcaa aataatgaga actgacacaa    83580
ctttgcctta aagagtacta gactggacct tctcatatta cgtttaagga agacttagag    83640
tgttcattga tgtttacgat tttaatattt ctgaaggcca ttacagtggc ctggatatgt    83700
gctgaaagcc aaactttta attttttggt tttttaagc aaagaaatat tttaaataaa      83760
tcctatttca acactgaaat tgttgaaaac cgtctcataa caaaaggaaa aaacattgga    83820
atttttgttt tagtggtcag tatagggaa tgaaagcgtc tgttgttacc cacgtaacta    83880
ttttgataag tattagaggt taaccttaaa tccagcaaaa cattaaaaca gaaacttttc   83940
aacttggagc ctgccattca gcgttgaggt agatgagttc cgacactgtc acggctgtgt    84000
tcccagcagc gaaggcctct gcggagctgc cagtcgtctt gaacgtgcat gggcggcgtg    84060
tgacatctcc agggaggccg tccgaagtcg agaatcgtca gctgtaagta ggagctacac    84120
```

```
agcgcagaga aaatggaacc acccatccgt gaggcctctt tccggaggga gccgcacact    84180
tggacttgag agtttgccag cagcgagctc ggatgcatct ctccaaaagc caccaaggtc    84240
ggcgcgtctg aagagcgttt tgcggtcatc agacttcctc atctgaaaac acagaacata    84300
ctgaccctt caagtactta gtcatttcc tgaaagtgtg gtctgtttca gaatgctgtg     84360
gcaaccaggt aggtgtggca ctggccatgt gccacgtctt tgccctttgt agtctgtcag    84420
atattaaagt ttctaacct gtttttttaa tctccaagaa tggggaaagt ggaatgtaga    84480
gatggaagca gaacgtgatg tttggataca acagctattt aatcctttt tatttttaa     84540
gcaaaacact cagttttcta ccttattttc taatgttgat ttcatggtaa tactgacagt    84600
tggaagtgtt taacataaaa actcattgct aaagagcact gaggaaatgg gagctagcgc    84660
acttgtaata aaaataaaga caaatattt tcttgaatgc atatatgtga ttgggtattt     84720
taaaaaccag tatcatctgt catctccaaa agattacagg agtcagcttg ttaatacagt    84780
agtgttagta ggtctgtat ttttaattca gtacttagaa ttctaggtcc tttattgccc     84840
aaagtcagca cagttagttt ataccacaga ctctgtcttg gggcacagta gtgggcggg     84900
gtagtgactt tgcctaaaca tcacccagct ggaacagagg ctgagcgggg ctttaggcac    84960
ttgccagatg ggaactgggt tgcaccctcc ttgctccctg tcattttctt gtcactcttc    85020
ctgcttccca gtgttttatt ttatgccttg ctcgttgtac atcatgatga ctgatggtct    85080
tcaaggttgt gaggaaagcc gtctccctgc ttgactcgac tgctgtccca gaggagagtc    85140
ctgtgcgacc tgagcggggg tggctgccat ttccagcatg caggtgactt ccaaagaatg    85200
agtcaggtgg cactgaaagc catgggttct gaagaggcga atttgttgaa aagtcccaag    85260
ggtctgaatg aaagcatctt taatcaacac tcaacactcg caatattcta gaaaaccata    85320
tactgtgctg gttgaggcca aaggttaaca ttgctccact gttcaccaag gaaggggggca   85380
gtggccatcc gccgcggcct cacgtgcgtt gtaacaagcc ctcatcacat gtgtgagtct    85440
tacgtgcaca aaaagagaag gctttggtac tgaaactgga caccttgtgt actcgatacc    85500
ttcacagctt ctattggaca tattttcttt ttaggaatga aggaaaattc tcccattttt    85560
gagccattct tttgtcaatt ctacaaaatt gcatgtaact ttataaatat ttttaaaaga    85620
tatagttttg taaatattta atattccgct aatttgattt tgaattgtaa atgtcaagta    85680
ttctgttttt ggggttttta tgttttatta tactttgtta aaaaggacaa attgtacatt    85740
tttagaatgt ttttatgagt aaatttaatg tactgaaaat aaaattttta aaaaggctg     85800
```

<210> SEQ ID NO 6
<211> LENGTH: 1747
<212> TYPE: DNA
<213> ORGANISM: Homo sapiens

<400> SEQUENCE: 6

```
cagcgagagg gcgcgagcgg cggcgctgcc tgcagcctgc agcctgcagc ctccggccgg     60
ccggcgagcc agtgcgcgtg cgcggcggcg gcctccgcag cgaccgggga gcggactgac    120
cggcgggagg gctagcgagc cagcggtgtg aggcgcgagg cgaggccgag ccgcgagcga    180
catgggggac cgggagcagc tgctgcagcg ggcgcggctg gccgagcagg cggagcgcta    240
cgacgacatg gcctccgcta tgaaggcggt gacagagctg aatgaacctc tctccaatga    300
agatcgaaat ctcctctctg tggcctacaa gaatgtggtt ggtgccaggc gatcttcctg    360
gagggtcatt agcagcattg agcagaaaac catggctgat ggaaacgaaa agaaattgga    420
```

```
gaaagttaaa gcttaccggg agaagattga aaggagctg gagacagttt gcaatgatgt     480
cctgtctctg cttgacaagt tcctgatcaa gaactgcaat gatttccagt atgagagcaa     540
ggtgttttac ctgaaaatga agggtgatta ctaccgctac ttagcagagg tcgcttctgg     600
ggagaagaaa acagtgtgg tcgaagcttc tgaagctgcc tacaaggaag cctttgaaat     660
cagcaaagag cagatgcaac ccacgcatcc catccggctg ggcctggccc tcaacttctc     720
cgtgttctac tatgagatcc agaatgcacc tgagcaagcc tgcctcttag ccaaacaagc     780
cttcgatgat gccatagctg agctggacac actaaacgag gattcctata aggactccac     840
gctgatcatg cagttgctgc gagacaacct caccctctgg acgagcgacc agcaggatga     900
agaagcagga gaaggcaact gaagatcctt caggtcccct ggcccttcct tcacccacca     960
ccccccatcat cacccgattct tccttgccac aatcactaaa tatctagtgc taaacctatc    1020
tgtattggca gcacagctac tcagatctgc actcctgtct cttgggaagc agtttcagat    1080
aaatcatggg cattgctgga ctgatggttg ctttgagccc acaggagctc cctttttgaa    1140
ttgtgtggag aagtgtgttc tgatgaggca ttttactatg cctgttgatc tatgggaaat    1200
ctaggcgaaa gtaatgggga agattagaaa gaattagcca accaggctac agttgatatt    1260
taaaagatcc atttaaaaca agctgatagt gtttcgttaa gcagtacatc ttgtgcatgc    1320
aaaaatgaat tcacccctcc cacctctttc ttcaattaat ggaaaactgt taagggaagc    1380
tgatacagag agacaacttg ctcctttcca tcagctttat aataaactgt ttaacgtgag    1440
gtttcagtag ctccttggtt ttgcctcttt aaattatgac gtgcacaaac cttcttttca    1500
atgcaatgca tctgaaagtt ttgatacttg taacttttt tttttttttgg ttgcaattgt    1560
ttaagaatca tggatttatt ttttgtaact ctttggctat tgtccttgtg tatcctgaca    1620
gcgccatgtg tgtcagccca tgtcaatcaa gatgggtgat tatgaaatgc cagacttcta    1680
aaataaatgt tttggaattc aatgggtaaa taaatgctgc tttggggata ttaaaaaaaa    1740
aaaaaaa                                                                1747
```

<210> SEQ ID NO 7
<211> LENGTH: 245
<212> TYPE: PRT
<213> ORGANISM: Homo sapiens

<400> SEQUENCE: 7

```
Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
            20                  25                  30

Leu Asn Glu Pro Leu Ser Asn Glu Asp Arg Asn Leu Leu Ser Val Ala
        35                  40                  45

Tyr Lys Asn Val Val Gly Ala Arg Arg Ser Ser Trp Arg Val Ile Ser
    50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Asp Lys Phe Leu Ile Lys Asn Cys Asn
            100                 105                 110

Asp Phe Gln Tyr Glu Ser Lys Val Phe Tyr Leu Lys Met Lys Gly Asp
        115                 120                 125

Tyr Tyr Arg Tyr Leu Ala Glu Val Ala Ser Gly Glu Lys Lys Asn Ser
```

```
                    130                 135                 140
Val Val Glu Ala Ser Glu Ala Ala Tyr Lys Glu Ala Phe Glu Ile Ser
145                 150                 155                 160

Lys Glu Gln Met Gln Pro Thr His Pro Ile Arg Leu Gly Leu Ala Leu
                165                 170                 175

Asn Phe Ser Val Phe Tyr Tyr Glu Ile Gln Asn Ala Pro Glu Gln Ala
            180                 185                 190

Cys Leu Leu Ala Lys Gln Ala Phe Asp Asp Ala Ile Ala Glu Leu Asp
            195                 200                 205

Thr Leu Asn Glu Asp Ser Tyr Lys Asp Ser Thr Leu Ile Met Gln Leu
        210                 215                 220

Leu Arg Asp Asn Leu Thr Leu Trp Thr Ser Asp Gln Gln Asp Glu Glu
225                 230                 235                 240

Ala Gly Glu Gly Asn
                245

<210> SEQ ID NO 8
<211> LENGTH: 13111
<212> TYPE: DNA
<213> ORGANISM: Homo sapiens

<400> SEQUENCE: 8
gcggccgcgt ctcctccctc ggcgttgtcc gcggcgcgag ccacagcgcg cggggcgagc      60
cagcgagagg gcgcgagcgg cggcgctgcc tgcagcctgc agcctgcagc ctccggccgg     120
ccggcgagcc agtgcgcgtg cgcggcgcg gcctccgcag cgaccgggga gcggactgac      180
cggcgggagg gctagcgagc cagcggtgtg aggcgcgagg cgaggccgag ccgcgagcga     240
catgggggac cgggagcagc tgctgcagcg gcgcgcggctg ccgagcagg cggagcgcta     300 cgacgacatg gcctccgcta tgaaggcggt gagcgcgccg ggagcccggg cggctggccg     360 ggggggggcct ggcgttgggg agggacgggg atggccgcgg gcgcgttccc ctcccggcca    420
tgggcgaccc ggcgacccgg ctgggcgtgg ccgcccgccc gcccttagcc cgcgcttccc    480
gctcccgctg ggcgccccgc cacttcctga ggctgggccc agggtggggg atccgggagg    540
gtgcagttcg ggatcgcgaa ggcagccccg gaagggggcc gggccggtcg gggtcgccac    600
atcttagttc ggaacccggc cggggcagag gggtgcccta ggggacgcga aggagccgca    660
tttctcctag agcgtttcac cggacccggg ggctcccccct ctcgtcttcc tccgttcccc   720
aacttggaat aaagaatcac ctagtaagtg gcgccctgtc tcagctggtt ttctctgcca    780
cgacctgaag tctgcaattc cgatctgttt tgctctgctc gttcgaattg ttctggttcc    840
atcttcccac gcctgggggt ctggctttgt gtgcgaagac ccctttcctg cagtctaggc    900
gtggacgggg gcgggagagt gggcggaggg tgtgggcccc cactccacag ccccaggttt    960
gctgctgcgc tgtctgcttg gagattaaaa tgaaacgtga cttctaggtg agacgaatct   1020
gtgtgtcttt gcattcctga gaccctcata aatcgattct gcagcttctc ggtggatga    1080 gtcgtgccca gccacaccct agcaaaatac cgtgggtcac acaccacctg catttctgag   1140
ttccggttac catctcactc tctctccacg ttatttacg ttttctgtaa atgaatattt    1200
cctctccctg cgtcaaggtc acacagtggt agaacaactg cgaccaccaa cctatgttca   1260
gtgtacaacc tcctgagacc tgggaggatc cccttgaact ccgccttaga cctatacatt   1320
cagaaattcg gcggtgaga ctcagacatc tgcattgtaa ccagctctca caggcgattt    1380
ttagctggct taagtctgag aattactgcc catgattata gtaaatgtat cctttgctgg   1440
```

```
ccttttggag ggagttccga aaaaaaactg ccaatacaaa ggctccctaa aatcttaagt    1500
catttggaaa gctcatttga aggcttttga tgttaatatc agatgaaata tgtagttggg    1560
gccaatattt aggattgttc aggtaagaaa ggtgcttgaa gagttgcctt tcctctggtg    1620
tccttgttac acacataact gggtgtgttt ggaaaccagc aacaccgttg cccgtatgtt    1680
gatttgttgg tgatcttgac ttgagcacta ttagcatgct gttgtggtga ggcaggtttt    1740
cttccagacc gggggacggt ctaggtctgg aggctgaact ttatgtaatt caggggtcc     1800 tttaaaagaa aatctaaaat atagttttgc atatttttaca aaaatgggac tgacgaatgc   1860
atttccttgg aagggaccct gaaccttaat tttctgtggg ataaagctgc ctctgtccac    1920
agcaggtcac acttaagccc ctcctcccca gtaactgagt ggtgctggga ttatgcaggc    1980
tgaggcctct ccacacattt tcatgaagtg gttgctcacc ctctaagtga gacgtaaaga    2040
ctgcagtgtt cggagccctt tgggaaataa atgtggtgaa agaaaggag ggacgaggtt     2100 taaaggaagg ggaaatggag gttaaggaaa aatggctaga aggtgtgttc tggaacaatc    2160
agaaacctga ggcaacttga aatgggggaa aaaggcaaga atggagagat gttaccagaa    2220
cgaaatctag tttgagcaga gaaaagact ggctttctag taggcttgta aaatgctttc     2280
ctgcagcaag ctacttgtgt ccatagatct tctctggagg gttaaggtag ccttttgtaa    2340
accaaaggaa tctataatat ctatatttga aataattaat gagttggaaa agccacccag    2400
cgtagaagag tcaatccaag cttttaattct gccatctcag aatggtgata aaccatttct   2460
cccccatcat ctaaatggaa tatattgtgc ttataggtat tttctttaaa agaaaaaaaa    2520
gaatatattg gaagggactg gcaggggtca ctttccctgc taacttggtg tttgtagatt    2580
aaattcttaa tgttactggg atgactcagt ctctatgtta ttaatctcat cagccttaac    2640
taaggctttt ggaaagggtg taagtttcag taaccctctg ggtttacctg ggctttcttc    2700
agggctgggg aagggcaggt aagtagcctg ctgtagggag gatggagcag gacacatgtg    2760
ttaaggatat attctgatgc caccagtctg taaccttgaa acttacatct ggctttagg     2820 tcctctgaag tataaaacta gtgatgttgc tgttattaac aagtcagttt tgccttcagt    2880
cttctaactt gttttctgtt tccttcataa ttaaaatgct cacttgataa tactgccttc    2940
ctgtaatgat tgatgttcct cattctacca gcgtcacctg gaggacagtg ttggtaagct    3000
tgaagaaaaa tcgtgcatac tggaaacaat ggtcttgcct caaacctgtt gagaacttct    3060
cttccctgct tctctccata atttgaagaa gcaagaaatg tttctgaagt gaagcataaa    3120
ggagtatctt caagctctat ctcataccta ccagcttgca tagagtataa tagtgggaag    3180
aaatattgtg aaagattcta gaacctaagt cctttctagg ctaggcaatt ctaggctaca    3240
caattcgtag tctctgtaaa taccatttga taactgaaat aaacctataa agtgggatta    3300
aatgttagtc cagaagacta agtgatttaa ggaaagaggg aaaataacca gatagatttc    3360
tggtggatat tcatagacag acataatttc atcatgtatt atggccctaa gtcatctatt    3420
ttatattaaa acatagatgg taactgtaaa gttatcaaat gtaaaaatta ctgggctagc    3480
attgtgtttt aacactgata caccagttga ttacagtgtt gacagaaaac gggcagaaac    3540
acgtttaaag tacctgcaga atatatatat agaaatcttt ttttttttaat cagtgttgac    3600 caggttggcc tcgaacgtgt agcctcacct ccccgagtgc cagggcaacc ggcctgagcc    3660
acagcggctc cctagaaatc ttaagtgcag gaaacaaaac tacagtttaa ggaaacagga    3720
gtcgagagag aggggcattt ggcccaacca ctggcaaaag gctgttgttg caacaactgt    3780
gagattctgg gaagtgggga aatgagcagg tgctgtgtaa aagtgcacag ctgactgccc    3840
```

```
caggtgagac agatcagtgt cacagagagt aggaggattt tgaggtgtga ttagtatttt    3900
tttttttttt cttaaagaga tggtctcgtt ctggaaccca ggctggagtg cagtcgtggc    3960
acgatcataa ttcactgtag ccttgagctc ctgggctcaa gtgaacctcc tgagcagctg    4020
ggactacaga tgcatgccac cgtgcccagc taattattaa attgtataga caggatctct    4080
atatggtacc caagttggtc tcaaactcct ggcctcaagc agtcctcctg cctcagccta    4140
ttaaagtgct gggattacag gagtgagcta ccacacccaa ccagtaggaa atcttaaagc    4200
cacattgata ctacagtttg aaatatgtaa aaactaggga gctatgtttc ccactaactg    4260
ggcatttaaa atgtaatcgt ctttgaggaa ggaagaaggc tctggattat tcttgtaata    4320
gtttgaattt aaaaggtcct ttcaggtggg caaacagctt acgtggcttt cttgcactga    4380
aatagaaact gtagtcccca tgtgggtttg ggtccctgaa ttatcccag aagaacttcc    4440
acagtccgga actgactccc ttaaagaaac caaaaatgta ttttctttgg tggggatttt    4500
ctttagttgg tctttgtctg ggattttata tcagtgacag actgtagcgt cacacttttc    4560
cagaaatacg gtttcggaga gggtaccccct aacgtttat gtgtgtgtgt gttacattta    4620
gcaagtttat ataacatatt ttactttttt tttttttttt ttttttgaga cagtttcgct    4680
cttgttgccc aggctggagt acaatggagc aatctcggct ctctgcaacc tctgcctccc    4740
gggttcaagc aattctcctg cctcagcctc ccaagtagct gggattacag gcatgcacca    4800
ccatgccatg cccgcctaat tttgtatttt tagtagagat ggggtttctc catgttggtc    4860
aggctggtct tgaacacccg acctcaggtt atccacctgc ctcggcctcc caaagtactg    4920
ggattacagg cgtgagccac tgcgcttggt tagaacttat ttaactttt aggcacttgg    4980
taaacggtag ctgttagtcc atgtgtactt ttttttttgg tggggggggg agtcatgctc    5040
tgtcacccag gctggagtgc agtggcagga tcttggttca ctgcaagctc cgcctcctgg    5100
gttcacgcca ttctcctgtg tcagcctccc aagtagctgg gactacaggt gcccgccacc    5160
ttccatgtgt acattcttgt ttaacaattc aggataggta ctgttactcc cctttacaaa    5220
tgagactttc agaggttgat tttctcatgg tcaaacagct agtaagttgt gaattcaaga    5280
ttcaaactca aatttagagc tctcatttta accactatgt aacaatgccc catgaggcaa    5340
agggataata tgtctagtat acattctggt atattaacca ttgtcagcac tggtgactga    5400
aatccaagaa ctcttcataa gtgggcttac taaacaaata attttatctg ttgggtgcaa    5460
gtcattttt tttttccaaat acgattaaga acaatctgcc atttatgggt tttagctaca    5520
acagagaaac ataagaggga aactcacata tctggatttt gcttgttctg aaggcttgga    5580
ggcctttttt tttttttttt tttttttttt tttttttttt ttgcttaaca agtattgaa    5640
tttgagtttc tcctgagtta agaagtgcag gactatgtta catttatttt ggggtatttt    5700
aagaaattat ttcatattct tggcaccagt tgtttctcca tattgccttt aatgtatttt    5760
tctccctgca ccctttagta tatttttatg caggccccaa aatttctgtc tctaggttgc    5820
tggtaaaatt cctcctagtg tccaagtgga ggcagcttgt cttctgtccc agcattttgg    5880
tgctcctccc gccccactc ctggctgcag tggcattccc ttctgcggtg gtgagtgtta    5940
gcacttccaa tgatccgaac ctggcacagc ttctgaagcc ttcaattcgg atgcctctag    6000
ggacagtagc atgcagtaat gccattcaga tggtgttgta tttaatcctt gccaatcccc    6060
atgaaaatgt tcagttatgt caaaagcaag gcaaaaacag tctcttggct atacaagggt    6120
agctgtttta tttgactaaa atttagctta gagtggatgt tacttacccg aacttgcctg    6180
```

```
ctctgagctt gaagtttagc ctatttgtgg tcttacagaa ttgcagcctc atcctggtga      6240
ggataagggg ctcagcctga ccctggctgg tgatgttctt gcccagtggc ctgtaggact      6300
tggtctgttg gtggatatct ttccagcttg gggcaggcca ggcaagatcc tcacttccta      6360
agcattaact tgggaaagag ctcagcaagc tttcatccct ctagctcatt ttttgttttt      6420
ttgagacaga gtcttgctct gtcgcccaag ctggagtgca gtggcacagt cctggctcac      6480
tgcaacttcc acctcctggg ttcgagcgat tgtcatgtcc cacccaagta gctgggatta      6540
caggtgcacg ccaccatgcc cagctaattt ttgtatttttt agtagagatg gggtttctct      6600
atattgactg ggttggtgtc gtactccctg gcctcaagtg atccgcctgc cttggcctcc      6660
caaagtgctg ggattacagg tgtgagccat cacacctggc ccctcaaacc ctcaaactga      6720
cttttctcac acagacacac acacatacac gtacacacac acttctgcca aagaagctta      6780
aaggttttat gatgtggtta tgtttactta atcatgagaa tcatttactc atatcaaaag      6840
caagctggtt gatagcatgt aggtgtgggt agctataaag gatgagccca tagcatgtgt      6900
ggagctgtga aggatggcag catattcgag tgaggtagca ttacccctaa cttaggcagc      6960
tatggcctgg cagctcgggg gtggcatttt tgtttgctca gtgttacttt tgatgttgga      7020
tgtttcccag attgagaact ttaaattttc ctaaatagtc cctgtactgt ttttggcagt      7080
ggatctattt ttactcacac acatagtttt ttgccttgtg agtagtgggt ggaggccctt      7140
aggggttttt gggtaaatga atagtgtcat aggaagataa gtgaatgatc agcaggccag      7200 gtcattttttg acatttagta atgttggggg tagtcctgga gcagagaaaa tgtgtgaagt      7260
gagtgccctg gggtggggac taggtgtagc caaaggctgt ttggtcagga cgtgagtaaa      7320
actggctgac agggaagtcc aatccttaaa agaaatggag aggagggcct tgtgcatgg      7380 gaagagccca tcagtttaag gttgtccttc aggaaggtg taagtaggat tacagagggt      7440
gggaaggcag gcaggacacc tagaaagcag agaggctgtg agcaggggtg gcgaaacccc      7500
tggtttgtgg cccggtgaag actcagtgcc tagtgtggct acactgaggg aaggtgccgt      7560
gtggcagaaa tgactgttgt aatcttggtg ttagagcgga aagaggctga aaactattgt      7620
ctaggcctgt ctgtaaaatt ctgtcttgtt gttgcttcat gttcctgatt tgtgagatg      7680 cagcaaatgt gatttcatta gattttgcag atgatcttag gtagcatggt cggggcctgg      7740
agagcatcca ttactctgtg ttgccacccg gtgtttgcct ctcagtacag tttatgactg      7800 aactttttcat tagttctcct ggctcctgta ttttggtatt tgaagtgttg ggaactggtg      7860
ctaagtatca tccatcaaga ttggctatcc atcttttttgt tttaatggac tgtctgattt      7920
tacatgggtc tataattttc cagtctggga aaaactcagt tttctttagt tatctggtca      7980
agtagtaagc catcttcatt tcatgttttcc ttttgttaac tgaattataa cccaggagta      8040 ttaaaaata ctgtatttaa atgtatccag ttatttccta gttaggctct ggctggggta      8100
ttaggaacaa tatttgcttg ctgagatatg ttagtcaccc tcagctaatg ctgatagtga      8160
ttcattcaga ctggcaggca accagatgat ttttacataa acactaatac tcccagtaaa      8220 tgattttttct tgtgaaggtg tcatcataaa tactgcccag tagccttttt tggcagctta      8280
ttcctgatga gaaagaaata tgcttacaga tacacccaaa cttcacgtta gtaggaagcc      8340
ctgccacacc ttttattggt gcacaggaaa aacgaaatca tggaacattg gagctgaagg      8400
aggccttgga gatcatttgg gctaatcctg cttatttttac tttggatgtc caaaaaggtt      8460
gtgatttgtt taaggtcaca tagctagctc agactaaact tcagatgtct tgggtttaat      8520
aattataccg ccttttgtgt tatgcaagca ttctgtatta tacatacatg tatttcagat      8580
```

```
ttgtactcac tttaaatgat atactctggg aagttacctt ggtgtatctt tgccagtttc    8640
acagaagcag ctttgttagt cacaggagga agtatattgt gactccttat ggatattatt    8700
tgtattttaa tgccaaatgg ccttagttta attactacaa gatgaaagga gctctccaaa    8760
ttctgttgtt gccttatgct ttgttttatt gaatattgct ctagaaacgc aagtcattct    8820
agaggattca agcattctga aatttatcag aatatttggg atggaatttt gattcagaag    8880
tgttgttcgt taaagactaa agtagttact catcttttg tagttcataa gtgtgatgat    8940
tgggttttga catgcaggtg tgagatgtgc caccctcaaa ccttgttaca acatagacat    9000
gtgaccctct gatgtgggca aaaaagact aagttattaa atatttacaa agtctctatt    9060
ttccgtaaga aaatgtatgt aagtgtttaa aggcacttac tggaggagga aactagtggg    9120
gttataggtg ttcagctgga tttaagggga gcatggattg tagattcatg gtagactggg    9180
gcagatcaca gtgagaggta tggagactac taatgaatat gtgaggatga ataatgagaa    9240
ccctggcttg accagagtgg aggcagcacc cctggggaat ggtcaggata gctgttagcc    9300
aaagaccaca ctgaagaaag aagtgggtag gcaaaggaga gactttgcct gtgttaaggg    9360
tttgtagcag aagagtaggg gtcctgggga caggaaatg gagaaattaa gagtgagctg    9420
gtatttttat tttgtctggg gcttggggt agggaggact cagacaattg cttgttttac    9480
tttgtgagaa cttggcacgt tttctgattt ttacctgtaa taatgattac acttgctgct    9540
tatgtccttg aaccactaat tccccaaata aaccatcatt gttcatgatt tctgatactc    9600
cactgctcag tcttctcaat ccattttaag tgtgtctatt tgaatatgct attgataact    9660
ttccccaatg aacttggcct tttccctctg gaggtctgt ccttacagat tggttaagt    9720 aataccttt ttgtttagtg ttttatggtt tcctaagtgc tttgctttct tttttttcat    9780
tattgaaatt aaagaccttt tggataagca gagactgatt taataaaatt aaagacccttt   9840 accagtaggt catattaagg aatccctcta ctttagacga cacaccatct tttaagggct    9900
tgtgaaatgt cctgggtcaa tttaggaagt catttttcttt gcttgggccc agaccaactc   9960
tgttagcaac tctgttagga actcttgtta ggaaactctg ttagtttcct aggggtgct   10020 gaacctagta cgacaaactg gatagtttaa aataataaat gtattctctc atagttctgg  10080
acgctagaag tttgaaagtg aggtgtaggc aggccacgct ccctctgaag gctctaggga  10140
agaatccttc ctaggcactc tcccagcttc tggtggcttc tggcaaccct tggtgttcct  10200
tggcttgtag atgcgtcact ccagtctttg cctccactgt cacatggcat tcttcctgtg  10260
tgtgtgtcaa aatctcacta tccttataag gacacctgta attgcactta gggcacaccc  10320
taatgtccag tatgacttca tcttaactaa ttacatctgc aaagacccta tttccaaata  10380
agctcacatt cacaggaacc tagggtcaga acttcagcgt atcttttggc gggggataca  10440
gttcaaccac tgcaaagtct aataatgctc ttcctactaa ctgcatagct agttcacttg  10500
tagttggcat catggagaac taagggaagt taaagcttgt gaaatttaac tcttccactt  10560
aaaataattg atgcttccat ccttgatgac cagagtttcc tgtgaggtag gtcagagtac  10620
aacttcctgc tgagtagctg tgcttccttt cactaggagc tgggggtact ttcatgtcac  10680
ttatgaattg ttcttcattt tggttttggga gagggctggg agtatcagtt agggttccat  10740
gtgtagccac acagggcgaa gctctggcca ctggatctgt gtgatgttcc atctgatctg  10800
tgaagcccca ccatctgtta atgtgtattt gaggagtggt tggttctttc cagagtataa  10860
agctggaagc agagtctgga acacttccag tctgttgtct ttgaacattt gacaaaggga  10920
```

-continued

```
ccgtacgatc ttactgttca gagtatcttt tttttttttt tttttttctt ttgagacgga    10980
ggcttgctct gtcgctagct aggctggagt gcagtggcac gatctgggct cactgcaacc    11040
tccgggttca agagtttctc ttgcctcagc ctcccaagta gctgggacta caagcgcgtg    11100
ccaccacgcc cagctaattt ttgtattttt agtagagatg gggtttcacc atgttggcca    11160
gaatggtctc gatctcttga cctcatgatc tgcccgccct tggcctcctg aagtgctggg    11220
attacaggca taagccatcg cgcccggcct gttcagagta tcttttgcag aatggctgaa    11280
gctcgaggtt ttcttcttca ccattatgta ctgctgctgt acaaccttt cataattatc     11340
cttagtccca ttcctctacc aaggtgaaag caacatctta tcagacccga attatgaatt    11400
tctcaagccc ctatgatttt ctgttttggg tgccaagtat ttatctcttc tgttagacta    11460
tagtctttct tcacataggg ttcatgtcta tattggtttt atccatgggt ggttttatt     11520
ctccagagtg actgacctgt tcgtaattcc gttcttgaga aggattgttg attatgttga    11580
agggaaggct tcttaccaag atttcagat tttgctttca atgtttatct tttgggtt       11640
ttgcaggtga cagagctgaa tgaacctctc tccaatgaag atcgaaatct cctctctgtg    11700
gcctacaaga atgtggttgg tgccaggcga tcttcctgga gggtcattag cagcattgag    11760
cagaaaacca tggctgatgg aaacgaaaag aaattggaga agttaaagc ttaccggag      11820
aagattgaga aggagctgga acagtttgc aatgatgtcc tgtctctgct tgacaagttc     11880
ctgatcaaga actgcaatga tttccagtat gagagcaagg tgttttaccct gaaaatgaag    11940
ggtgattact accgctactt agcagaggtc gcttctgggg agaagaaaaa cagtgtggtc    12000
gaagcttctg aagctgccta caaggaagcc tttgaaatca gcaaagagca gatgcaaccc    12060
acgcatccca tccggctggg cctggccctc aacttctccg tgttctacta tgagatccag    12120
aatgcacctg agcaagcctg cctcttagcc aaacaagcct tcgatgatgc catagctgag    12180
ctggacacac taaacgagga ttcctataag gactccacgc tgatcatgca gttgctgcga    12240
gacaacctca ccctctggac gagcgaccag caggatgaag aagcaggaga aggcaactga    12300
agatccttca ggtcccctgg cccttccttc acccaccacc ccatcatca ccgattcttc      12360
cttgccacaa tcactaaata tctagtgcta aacctatctg tattggcagc acagctactc    12420
agatctgcac tcctgtctct tgggaagcag tttcagataa atcatgggca ttgctggact    12480
gatggttgct ttgagcccac aggagctccc ttttgaatt gtgtggagaa gtgtgttctg      12540
atgaggcatt ttactatgcc tgttgatcta tgggaaatct aggcgaaagt aatggggaag    12600
attagaaaga attagccaac caggctacag ttgatattta aaagatccat ttaaaacaag    12660
ctgatagtgt ttcgttaagc agtacatctt gtgcatgcaa aaatgaattc accctccca     12720
cctctttctt caattaatgg aaaactgtta agggaagctg atacagagag acaacttgct    12780
cctttccatc agctttataa taaactgttt aacgtgaggt ttcagtagct ccttggtttt    12840
gcctcttta attatgacgt gcacaaacct tcttttcaat gcaatgcatc tgaaagtttt     12900
gatacttgta acttttttt ttttttggtt gcaattgttt aagaatcatg gatttatttt      12960
ttgtaactct ttggctattg tccttgtgta tcctgacagc gccatgtgtg tcagcccatg    13020
tcaatcaaga tgggtgatta tgaaatgcca gacttctaaa ataaatgttt tggaattcaa    13080
tgggtaaata aatgctgctt tggggatatt a                                   13111
```

<210> SEQ ID NO 9
<211> LENGTH: 21
<212> TYPE: DNA
<213> ORGANISM: Artificial Sequence

```
<220> FEATURE:
<223> OTHER INFORMATION: siZCCHC14-1 siRNA

<400> SEQUENCE: 9
gucugauucu ucaauaacat t                                              21

<210> SEQ ID NO 10
<211> LENGTH: 21
<212> TYPE: DNA
<213> ORGANISM: Artificial Sequence
<220> FEATURE:
<223> OTHER INFORMATION: siZCCHC14-2 siRNA

<400> SEQUENCE: 10
gcauuuuaug uggagcgaat t                                              21

<210> SEQ ID NO 11
<211> LENGTH: 21
<212> TYPE: DNA
<213> ORGANISM: Artificial Sequence
<220> FEATURE:
<223> OTHER INFORMATION: siZCCHC14-3 siRNA

<400> SEQUENCE: 11
ccuucucacg uguugaaaat t                                              21

<210> SEQ ID NO 12
<211> LENGTH: 21
<212> TYPE: DNA
<213> ORGANISM: Artificial Sequence
<220> FEATURE:
<223> OTHER INFORMATION: siZCCHC14-4 siRNA

<400> SEQUENCE: 12
gaauaaauuu gagucucuut t                                              21

<210> SEQ ID NO 13
<211> LENGTH: 21
<212> TYPE: DNA
<213> ORGANISM: Artificial Sequence
<220> FEATURE:
<223> OTHER INFORMATION: siZCCHC14-5 siRNA

<400> SEQUENCE: 13
gcaaagugag uguugaaaat t                                              21

<210> SEQ ID NO 14
<211> LENGTH: 21
<212> TYPE: DNA
<213> ORGANISM: Artificial Sequence
<220> FEATURE:
<223> OTHER INFORMATION: siZCCHC14-6 siRNA

<400> SEQUENCE: 14
gcagcuucag aguccaagut t                                              21

<210> SEQ ID NO 15
<211> LENGTH: 21
<212> TYPE: DNA
<213> ORGANISM: Artificial Sequence
<220> FEATURE:
<223> OTHER INFORMATION: siZCCHC14-7 siRNA

<400> SEQUENCE: 15
gugacggaau uuauuucaat t                                              21
```

```
<210> SEQ ID NO 16
<211> LENGTH: 21
<212> TYPE: DNA
<213> ORGANISM: Artificial Sequence
<220> FEATURE:
<223> OTHER INFORMATION: siZCCHC14-8 siRNA

<400> SEQUENCE: 16
ccacguggau cuggacucat t                                              21

<210> SEQ ID NO 17
<211> LENGTH: 21
<212> TYPE: DNA
<213> ORGANISM: Artificial Sequence
<220> FEATURE:
<223> OTHER INFORMATION: siZCCHC14-9 siRNA

<400> SEQUENCE: 17
caaucccucc cuuucuaaat t                                              21

<210> SEQ ID NO 18
<211> LENGTH: 21
<212> TYPE: DNA
<213> ORGANISM: Artificial Sequence
<220> FEATURE:
<223> OTHER INFORMATION: siZCCHC14-10 siRNA

<400> SEQUENCE: 18
gaggucuugu ggucugauut t                                              21

<210> SEQ ID NO 19
<211> LENGTH: 21
<212> TYPE: DNA
<213> ORGANISM: Artificial Sequence
<220> FEATURE:
<223> OTHER INFORMATION: siZCCHC14-11 siRNA

<400> SEQUENCE: 19
agaccugaag ggauuaucat t                                              21

<210> SEQ ID NO 20
<211> LENGTH: 21
<212> TYPE: DNA
<213> ORGANISM: Artificial Sequence
<220> FEATURE:
<223> OTHER INFORMATION: siZCCHC14-12 siRNA

<400> SEQUENCE: 20
caauaacauc aguaaccaat t                                              21

<210> SEQ ID NO 21
<211> LENGTH: 19
<212> TYPE: RNA
<213> ORGANISM: Artificial Sequence
<220> FEATURE:
<223> OTHER INFORMATION: siZCCHC14-13 siRNA

<400> SEQUENCE: 21
ccucugaagu gacggaauu                                                 19

<210> SEQ ID NO 22
<211> LENGTH: 19
<212> TYPE: RNA
<213> ORGANISM: Artificial Sequence
<220> FEATURE:
<223> OTHER INFORMATION: siZCCHC14-14 siRNA
```

```
<400> SEQUENCE: 22
ggaccaaagu cgugcaugc                                             19

<210> SEQ ID NO 23
<211> LENGTH: 19
<212> TYPE: RNA
<213> ORGANISM: Artificial Sequence
<220> FEATURE:
<223> OTHER INFORMATION: siZCCHC14-15 siRNA

<400> SEQUENCE: 23
ccacguggau cuggacuca                                             19

<210> SEQ ID NO 24
<211> LENGTH: 21
<212> TYPE: DNA
<213> ORGANISM: Artificial Sequence
<220> FEATURE:
<223> OTHER INFORMATION: siYWHAH-1 siRNA

<400> SEQUENCE: 24
caagguguuu uaccugaaat t                                          21

<210> SEQ ID NO 25
<211> LENGTH: 20
<212> TYPE: DNA
<213> ORGANISM: Artificial Sequence
<220> FEATURE:
<223> OTHER INFORMATION: siYWHAH-2 siRNA

<400> SEQUENCE: 25
cacuaaacga ggauucuatt                                            20

<210> SEQ ID NO 26
<211> LENGTH: 21
<212> TYPE: DNA
<213> ORGANISM: Artificial Sequence
<220> FEATURE:
<223> OTHER INFORMATION: antisense oligo

<400> SEQUENCE: 26
gaaugaaccu cucuccaaut t                                          21

<210> SEQ ID NO 27
<211> LENGTH: 21
<212> TYPE: RNA
<213> ORGANISM: Artificial Sequence
<220> FEATURE:
<223> OTHER INFORMATION: antisense oligo

<400> SEQUENCE: 27
uguuauugaa gaaucagacc a                                          21

<210> SEQ ID NO 28
<211> LENGTH: 21
<212> TYPE: DNA
<213> ORGANISM: Artificial Sequence
<220> FEATURE:
<223> OTHER INFORMATION: antisense oligo

<400> SEQUENCE: 28
uucgcuccac auaaaaugcg t                                          21

<210> SEQ ID NO 29
```

```
<211> LENGTH: 21
<212> TYPE: DNA
<213> ORGANISM: Artificial Sequence
<220> FEATURE:
<223> OTHER INFORMATION: antisense oligo

<400> SEQUENCE: 29
uuuucaacac gugagaaggt a                                              21

<210> SEQ ID NO 30
<211> LENGTH: 21
<212> TYPE: DNA
<213> ORGANISM: Artificial Sequence
<220> FEATURE:
<223> OTHER INFORMATION: antisense oligo

<400> SEQUENCE: 30
aagagacuca aauuuauuca g                                              21

<210> SEQ ID NO 31
<211> LENGTH: 21
<212> TYPE: DNA
<213> ORGANISM: Artificial Sequence
<220> FEATURE:
<223> OTHER INFORMATION: antisense oligo

<400> SEQUENCE: 31
uuuucaacac ucacuuugct g                                              21

<210> SEQ ID NO 32
<211> LENGTH: 21
<212> TYPE: DNA
<213> ORGANISM: Artificial Sequence
<220> FEATURE:
<223> OTHER INFORMATION: antisense oligo

<400> SEQUENCE: 32
acuuggacuc ugaagcugct g                                              21

<210> SEQ ID NO 33
<211> LENGTH: 21
<212> TYPE: DNA
<213> ORGANISM: Artificial Sequence
<220> FEATURE:
<223> OTHER INFORMATION: antisense oligo

<400> SEQUENCE: 33
uugaaauaaa uuccgucact t                                              21

<210> SEQ ID NO 34
<211> LENGTH: 21
<212> TYPE: DNA
<213> ORGANISM: Artificial Sequence
<220> FEATURE:
<223> OTHER INFORMATION: antisense oligo

<400> SEQUENCE: 34
ugaguccaga uccacguggt t                                              21

<210> SEQ ID NO 35
<211> LENGTH: 21
<212> TYPE: DNA
<213> ORGANISM: Artificial Sequence
<220> FEATURE:
<223> OTHER INFORMATION: antisense oligo

<400> SEQUENCE: 35
```

```
uuuagaaagg gagggauugc c                                              21

<210> SEQ ID NO 36
<211> LENGTH: 21
<212> TYPE: DNA
<213> ORGANISM: Artificial Sequence
<220> FEATURE:
<223> OTHER INFORMATION: antisense oligo

<400> SEQUENCE: 36
aaucagacca caagaccuca a                                              21

<210> SEQ ID NO 37
<211> LENGTH: 21
<212> TYPE: DNA
<213> ORGANISM: Artificial Sequence
<220> FEATURE:
<223> OTHER INFORMATION: antisense oligo

<400> SEQUENCE: 37
ugauaauccc uucaggucua t                                              21

<210> SEQ ID NO 38
<211> LENGTH: 21
<212> TYPE: DNA
<213> ORGANISM: Artificial Sequence
<220> FEATURE:
<223> OTHER INFORMATION: antisense oligo

<400> SEQUENCE: 38
uugguuacug auguuauuga a                                              21

<210> SEQ ID NO 39
<211> LENGTH: 21
<212> TYPE: DNA
<213> ORGANISM: Artificial Sequence
<220> FEATURE:
<223> OTHER INFORMATION: antisense oligo

<400> SEQUENCE: 39
uuucagguaa aacaccuugg t                                              21

<210> SEQ ID NO 40
<211> LENGTH: 21
<212> TYPE: DNA
<213> ORGANISM: Artificial Sequence
<220> FEATURE:
<223> OTHER INFORMATION: antisense oligo

<400> SEQUENCE: 40
auuggagaga gguucauuca g                                              21
```

TARGETING HEPATITIS B VIRUS (HBV) HOST FACTORS

CROSS-REFERENCE TO RELATED APPLICATIONS

This application is a continuation application of and claims priority to U.S. application Ser. No. 15/268,119, filed on Sep. 16, 2016; which claims priority to U.S. Application Ser. No. 62/220,080, filed on Sep. 17, 2015. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on Sep. 22, 2017, is named 07917-0384002_SEQ.txt and is 165 Kb in size.

TECHNICAL FIELD

Described herein are methods of identifying host factors that modulate Hepatitis B virus (HBV) replication in mammalian, e.g., human cells, as well as factors identified by those methods, and methods of treating HBV infections by targeting those factors. Zinc finger, CCHC domain containing 14 (ZCCHC14) and Tyrosine 3-Monooxygenase/Tryptophan 5-Monooxygenase Activation Protein, Eta Isoform (YWHAH) are exemplary host factors.

BACKGROUND

HBV is an enveloped partially double stranded DNA retrovirus which infects hepatocytes subsequent to exposure of the host's mucous membranes or bloodstream. In adults, HBV typically causes a transient acute hepatitis; however, 5% of these infections become chronic, which in instances can progress to cirrhosis, hepatocellular carcinoma (HCC) and death. Infected neonates acquire HBV via transmission from their mothers and this results in high rates of chronic infection (>90%) and a ~25% risk of cirrhosis. Though an effective vaccine exists, it is estimated that nearly 2 billion individuals have been infected and of those 400 million are chronically infected (Hoffman and Thio, Lancet Infect Dis, 2007. 7(6): p. 402-9).

SUMMARY

Described herein is the discovery of mammalian host proteins that are required for HBsAg production and secretion, i.e., Zinc finger, CCHC domain containing 14 (ZCCHC14), and Tyrosine 3-Monooxygenase/Tryptophan 5-Monooxygenase Activation Protein, Eta Isoform (YWHAH), and their use as targets in anti-HBV therapy.

Provided herein are methods for treating a subject with an Hepatitis B virus (HBV) infection comprising administering to the subject a therapeutically effective amount of an inhibitory nucleic acid targeting zinc finger, CCHC domain containing 14 (ZCCHC14) or Tyrosine 3-Monooxygenase/ Tryptophan 5-Monooxygenase Activation Protein, Eta Isoform (YWHAH) mRNA.

Also provided are methods for inhibiting Hepatitis B virus (HBV) replication in a cell comprising contacting the cell with a therapeutically effective amount of an inhibitory nucleic acid targeting zinc finger, CCHC domain containing 14 (ZCCHC14) or Tyrosine 3-Monooxygenase/Tryptophan 5-Monooxygenase Activation Protein, Eta Isoform (YWHAH) mRNA.

Also provided are inhibitory nucleic acids targeting zinc finger, CCHC domain containing 14 (ZCCHC14) mRNA or Tyrosine 3-Monooxygenase/Tryptophan 5-Monooxygenase Activation Protein, Eta Isoform (YWHAH) mRNA for use in treating a subject with an Hepatitis B virus (HBV) infection or inhibiting Hepatitis B virus (HBV) replication in a cell.

In some embodiments, the ZCCHC14 mRNA comprises SEQ ID NO:1. In some embodiments, the YWHAH mRNA comprises SEQ ID NO:6.

In some embodiments, the inhibitory nucleic acid is selected from the group consisting of an antisense oligonucleotide; short interfering RNA (siRNA); and a short, hairpin RNA (shRNA). In some embodiments, the inhibitory nucleic acid is complementary to at least 8 consecutive nucleotides of SEQ ID NO:1 or 6. In some embodiments, the inhibitory nucleic acid is 8 to 30 nucleotides in length. In some embodiments, at least one nucleotide of the inhibitory nucleic acid is a nucleotide analogue or a 2' O-methyl. In some embodiments, the inhibitory nucleic acid comprises at least one ribonucleotide, at least one deoxyribonucleotide, or at least one bridged nucleotide. In some embodiments, the bridged nucleotide is a LNA nucleotide, a cEt nucleotide or a ENA modified nucleotide. In some embodiments, one or more of the nucleotides of the inhibitory nucleic acid comprise 2'-fluoro-deoxyribonucleotides, one or more of the nucleotides of the oligonucleotide comprise 2'-O-methyl nucleotides, one or more of the nucleotides of the oligonucleotide comprise ENA nucleotide analogues, and/or one or more of the nucleotides of the oligonucleotide comprise LNA nucleotides. In some embodiments, the nucleotides of the inhibitory nucleic acid comprise comprising phosphorothioate internucleotide linkages between at least two nucleotides or between all nucleotides.

A method of selecting a candidate compound, the method comprising: providing a test sample comprising zinc finger, CCHC domain containing 14 (ZCCHC14) protein or Tyrosine 3-Monooxygenase/Tryptophan 5-Monooxygenase Activation Protein, Eta Isoform (YWHAH) protein; contacting the test sample with a test compound; detecting binding in the sample between the test compound and ZCCHC14 protein or YWHAH protein; and selecting as a candidate compound a test compound that binds to ZCCHC14 protein or YWHAH protein. In some embodiments, the candidate compound is a candidate compound for the treatment of Hepatitis B virus (HBV). In some embodiments, the test compound is a small molecule.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 8B is a set of images showing cells transfected with the indicated siRNAs that were fixed, permeabilized and stained for HBsAg (green) and nuclei (blue). Image analysis software was used to determine the percentage of HBsAg expressing cells and the cell number. Representative images of two independent experiments are provided.

FIG. 9A is a set if images of HepG2-NTCP cells stably transduced with retrovirus expressing either the empty vector negative control (Vector) or a siRNA-resistant FLAG-tagged-YWHAH (YWHAH) and transfected either with non-targeting negative control siRNA (NT), a siRNA that targets a region shared among the HBV transcripts (HBV1) or either of two independent siRNAs (siYWHAH-1, siYWHAH-2) targeting the coding sequence of YWHAH. 72 h post transfection, the cells were infected with HBV. 7 days post infection the cells where stained for DNA (blue) and immunostained with an anti-HBsAg antibody (green).

DETAILED DESCRIPTION

Figure 1:
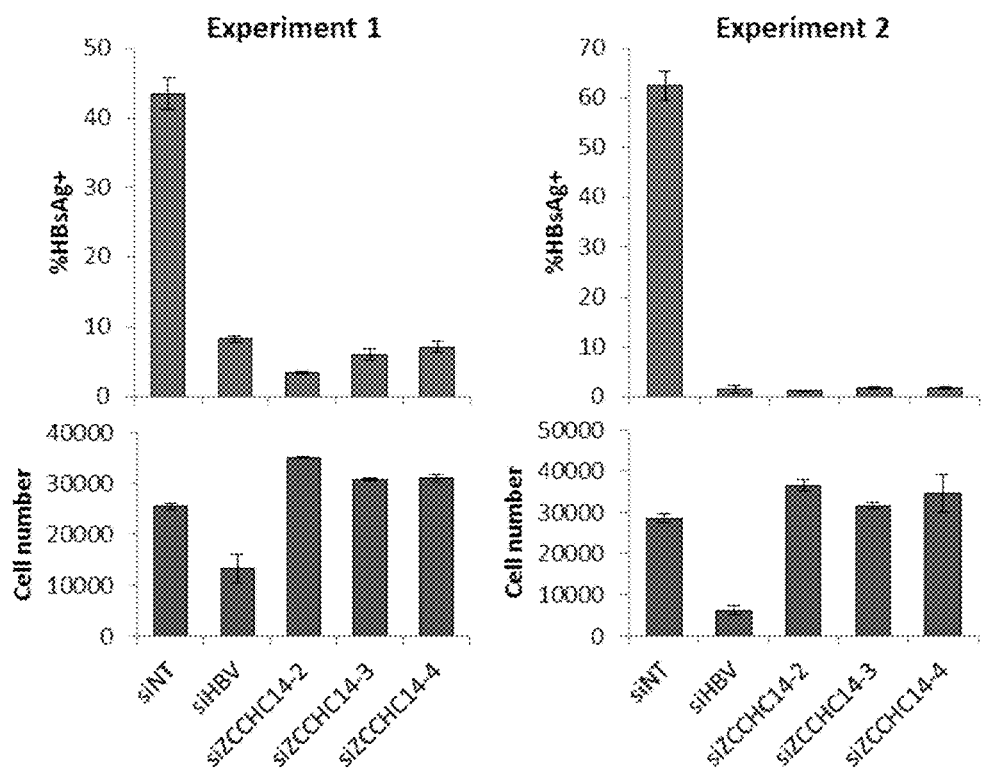
FIG. 1 is a set of four bar graphs showing data from two separate experiments, demonstrating that depletion of zinc finger, CCHC domain containing 14 (ZCCHC14) substantially reduced HBV surface antigen (HBsAg) expression.

While antiviral treatments exist for HBV, they fail to eliminate viral reservoirs. Patients therefore require lifelong therapy with the risk of viral resistance and/or hepatocellular cancer (HCC), the latter of which can occur even in the absence of cirrhosis. Consequently, a thorough understanding of the HBV lifecycle and the identification of new therapeutic targets for HBV would be useful. An improved grasp of host-viral interactions has been a longstanding goal of the virology community, with the hope that such insights will help treat and cure disease. Functional genomics represents a powerful strategy to define such host-virus interactions. We have used this strategy to identify host factors involved in the replication of HBV (HBV-HFs); we carried out a whole genome siRNA screen to identify HBV-HFs involved in the production and secretion of HBV surface antigen (HBsAg). This screen identified multiple host proteins that are required for HBsAg production and secretion. Described herein are two of the HBV host factors identified in this screen, zinc finger, CCHC domain containing 14 (ZCCHC14) and Tyrosine 3-Monooxygenase/Tryptophan 5-Monooxygenase Activation Protein, Eta Isoform (YWHAH), and their use as targets in anti-HBV therapy.

HBV Life Cycle

The lack of a robust cell culture system as well as the absence of previous genetic screening has resulted in many aspects of the HBV life cycle remaining poorly understood. Recently, the host receptor for HBV (NTCP) was identified (Yan et al., Sodium taurocholate cotransporting polypeptide is a functional receptor for human hepatitis B and D virus. eLife, 2012, 1); however other early events, including viral entry, uncoating, and delivery of the viral genome to the nucleus, remain undefined. What is known is that HBV enters cells and releases its partially double stranded DNA genome into the host cell's cytosol (Fields, B. N., et al., Fields Virology. 2007: Lippincott Williams & Wilkins. 1650). The viral DNA is comprised of a unit-length negative strand and a positive strand that is missing nearly one third of the genome. Through unknown mechanisms, this relaxed circular (rc) DNA is delivered to the nucleus, where it undergoes repair and circularization to form covalently closed circular DNA (cccDNA). Expression from unique promoters present in the cccDNA gives rise to four viral RNA transcripts. Through the use of alternative start sites, these mRNAs are translated into the five HBV proteins—HBeAg; the L, M, and S forms of the surface antigen (HBsAg); HBx; core; and pol. In addition, the transcript encoding core and pol serves as the pre-genomic (pg) template from which progeny genomes are produced. In the cytoplasm, the core protein forms the nucleocapsid and associates with pgRNA. Within these capsids, pol covalently links to pgRNA and reverse transcribes it to give rise to the rcDNA. Encapsidated genomes can then either reenter the nucleus, amplifying or maintaining the presence of cccDNA, or undergo envelopment by transit through the trans-Golgi network and subsequent release from the infected cell.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target ZCCHC14 or YWHAH nucleic acid and modulate its function. An exemplary target sequence for human ZCCHC14 is in GenBank at NM_015144.2 (SEQ ID NO:1), and encodes a protein having a sequence in GenBank at NP_055959.1 (SEQ ID NO:2). Another exemplary target sequence for human ZCCHC14 variant 2 mRNA is in GenBank at XM_005255858.3 (SEQ ID NO:3), and encodes a protein having a sequence in GenBank at XP_005255915.2 (SEQ ID NO:4). Genomic sequence encoding ZCCHC14 (GenBank Acc. No. NC_000016.10) is SEQ ID NO:5.

An exemplary target sequence for human YWHAH is in GenBank at NM_003405.3 (SEQ ID NO:6), and encodes a protein having a sequence in GenBank at NP_003396.1 (SEQ ID NO:7). Genomic sequence encoding human YWHAH is in GenBank at NC_000022.11 (SEQ ID NO:8).

In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (*Guide to Molecular Cloning Techniques,* 1987, Academic Press, New York); and Sambrook et al., *Molecular Cloning: A Laboratory Manual,* Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002). Exemplary siRNA/shRNA targeting ZCCHC14 can also be obtained commercially, e.g., from Santa Cruz Biotechnology, ABM, Ambion, Dharmacon, and other sources. Exemplary sequences include the following, which were used in the examples set forth below:

|  | | SEQ ID NO: | Antisense (5'→3') | SEQ ID NO: |
|---|---|---|---|---|
| siRNA targeting ZCCHC14 | | | | |
| Ambion, sense (5'→3') | | | | |
| siZCCHC14-1 (siRNA ID: S23202) | GUCUGAUUCUUCAAUAACAtt | 9 | UGUUAUUGAAGAAUCAGACca | 27 |
| siZCCHC14-2 (siRNA ID: S23203) | GCAUUUUAUGUGGAGCGAAtt | 10 | UUCGCUCCACAUAAAAUGCgt | 28 |
| siZCCHC14-3 (siRNA ID: s23204) | CCUUCUCACGUGUUGAAAAtt | 11 | UUUUCAACACGUGAGAAGGta | 29 |
| siZCCHC14-4 (siRNA ID: s529886) | GAAUAAAUUUGAGUCUCUUtt | 12 | AAGAGACUCAAAUUUAUUCag | 30 |
| siZCCHC14-5 (siRNA ID: S529887) | GCAAAGUGAGUGUUUGAAAAtt | 13 | UUUUCAACACUCACUUUGCtg | 31 |
| siZCCHC14-6 (siRNA ID: S529888) | GCAGCUUCAGAGUCCAAGUtt | 14 | ACUUGGACUCUGAAGCUGCtg | 32 |
| siZCCHC14-7 (siRNA ID: S529889) | GUGACGGAAUUUAUUUCAAtt | 15 | UUGAAAUAAAUUCCGUCACtt | 33 |
| siZCCHC14-8 (siRNA ID: S529890) | CCACGUGGAUCUGGACUCAtt | 16 | UGAGUCCAGAUCCACGUGGtt | 34 |
| siZCCHC14-9 (siRNA ID: S529891) | CAAUCCCUCCCUUUCUAAAtt | 17 | UUUAGAAAGGGAGGGAUUGcc | 35 |
| siZCCHC14-10 (siRNA ID: S529892) | GAGGUCUUGUGGUCUGAUUtt | 18 | AAUCAGACCACAAGACCUCaa | 36 |
| siZCCHC14-11 (siRNA ID: S529893) | AGACCUGAAGGGAUUAUCAtt | 19 | UGAUAAUCCCUUCAGGUCUat | 37 |
| siZCCHC14-12 (siRNA ID: S529894) | CAAUAACAUCAGUAACCAAtt | 20 | UUGGUUACUGAUGUUAUUGaa | 38 |
| Dharmacon, sense (5'→3') | | | | |
| siZCCHC14-13 (siRNA ID: D-014086-02) | CCUCUGAAGUGACGGAAUU | 21 | — | |
| siZCCHC14-14 (siRNA ID: D-014086-03) | GGACCAAAGUCGUGCAUGC | 22 | — | |
| siZCCHC14-15 (siRNA ID: D-014086-04) | CCACGUGGAUCUGGACUCA | 23 | — | |
| siRNA targeting YWHAH | | | | |
| Ambion, sense (5'→3') | | | | |
| siYWHAH-1 (siRNA ID: S14967) | CAAGGUGUUUUACCUGAAAtt | 24 | UUUCAGGUAAAACACCUUGgt | 39 |
| siYWHAH-2 (siRNA ID: S14968) | CACUAAACGAGGAUUCUAtt | 25 | — | |
| siYWHAH-3 (siRNA ID: S14969) | GAAUGAACCUCUCUCCAAUtt | 26 | AUUGGAGAGAGGUUCAUUCag | 40 |

The sequences can include one or more modifications as described herein.

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleotides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N ($CH_3$)—$CH_2$, $CH_2$—N($CH_3$)—N($CH_3$)—$CH_2$ and O—N ($CH_3$)— $CH_2$—$CH_2$ backbones, wherein the native phosphodiester backbone is represented as O— P—O—$CH_,$); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al, Helv. Chim. Acta, 1995, 78, 486). Other preferred modifications include 2'-methoxy (2'-0-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Delivery of siRNA In Vivo

Since 1998, when the first human RNAi-based clinical trials occurred, the number of clinical trials involving RNAi therapies targeting the liver has rapidly increased (Sehgal, A et al (2013) J. Hepatology 59: 1354-1359). To avoid rapid degradation of unmodified siRNAs in the blood and serum in vivo, chemical modification or conjugate formation (simple or poly-) may be used by those skilled in the art. Examples of modifications may include lipid carriers, such as liposomal vehicles (Kanasty, R et al (2013) Nature Mater. 12, 967-977); Watanabe et al (2007) J. Hepatol 47:744-50;

Aleku et al (2008) Cancer Res 68:9788-98; Moreira et al (2008) J. Nanosci Nanotechnol 8:2187-204; cationic carriers, such as cyclodextrin-based cationic polymers (Heidel et al (2007) Clin Cancer Res 13:2207-15) and biodegradable components (Dimitrova et al (2008). In some embodiments, liposome particles (Morrissey, D V et al (2005) Biotechnol 23:1002-1007), PEGylated nanoparticles (Carmona, S et al (2009) Mol Pharm 6:706-717), or Dynamic PolyConjugate (DPC) (Rozema et al (2007) PNAS 104: 12982-12987) may be used to deliver siRNAs to the liver. In some embodiments, this delivery system may feature reversibly masked polymers that are only revealed under specific conditions, such as the acidic environment of the endosome (Rozema et al (2007) PNAS 104: 12982-12987). In some embodiments, the delivery system may dependent on the attachment to a liver-specific receptor on the cell surface of hepatocytes, such asialoglycoprotein (Wu, J et al (2002) Front Biosci 7:d717-d725). In some embodiments, the target siRNA may directly be conjugated to cholesterol (Wooddell, C et al (2013) Mol Therapy 21:973-985). In some embodiments hydrodynamic intravenous injections and electrical pulsing may be used to directly deliver RNAi therapeutics (Morrissey et al (2005) Hepatology 41:1349-56; Golzio et al (2005) Gen Ther 12:246-51). RNAi therapeutics may also be delivered via electroporation of purified exosomes (Alvarez-Erviti et al (2011) Nat Biotechnol 29:341-345). For more information on in vivo delivery of RNAi, please see U.S. Ser. Nos. 12/479,747; 8,501,930, 8,017,804; 8,357,722; 8,314,227; and 7,371,404.

Pharmaceutical Compositions

The methods described herein can include the administration of pharmaceutical compositions and formulations comprising inhibitory nucleic acid sequences designed to target an RNA, optionally including one or more of the modifications described herein.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids.

Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy*, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, nontoxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Methods of Screening

Included herein are methods for screening test compounds, e.g., polypeptides, polynucleotides, inorganic or organic large or small molecule test compounds, to identify agents useful in the treatment of HBV.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, or purified ZCCHC14 or YWHAH protein, and one or more effects of the test compound is evaluated, e.g., the ability to bind to ZCCHC14 or YWHAH.

In some embodiments, the test sample is, or is derived from (e.g., a sample taken from) an in vivo model of HBV infection. For example, an animal model, e.g., a rodent such as a rat, can be used, or cells from the animal model.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on ZCCHC14 or YWHAH.

A test compound that has been screened by a method described herein and determined to bind ZCCHC14 or YWHAH, can be considered a candidate compound. A candidate compound that has been screened, e.g., in an in vivo model of a disorder, e.g., of HBV infection, and determined to have a desirable effect on the disorder, e.g., on viral titer or one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions. Candidate compounds that bind to ZCCHC14 or YWHAH can also be conjugated to a phthalimide moiety, e.g., to recruit ubiquitin to degrade ZCCHC14 or YWHAH proteins. See, e.g., Winter et al., Science. 348(6241):1376-81 (2015). These phthalimidated proteins can then be considered candidate therapeutic agents and screened in animal models or clinical settings as potential therapeutic agents.

Thus, test compounds identified as "hits" (e.g., test compounds that bind ZCCHC14 or YWHAH) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating HBV infection. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of HBV infection. The animal can be monitored for a change in the disorder, e.g., for an improvement in a parameter of the disorder, e.g., a parameter related to clinical outcome. In some embodiments, the parameter is viral titer, and an improvement would be a decrease in viral titer. In some embodiments, the subject is a human, e.g., a human with HBV, and the parameter is liver function or viral titer.

EXAMPLES

The invention is further described in the following examples, which do not limit the scope of the invention described in the claims.

Example 1. Identification of HBV Host Factors

Figure 6:
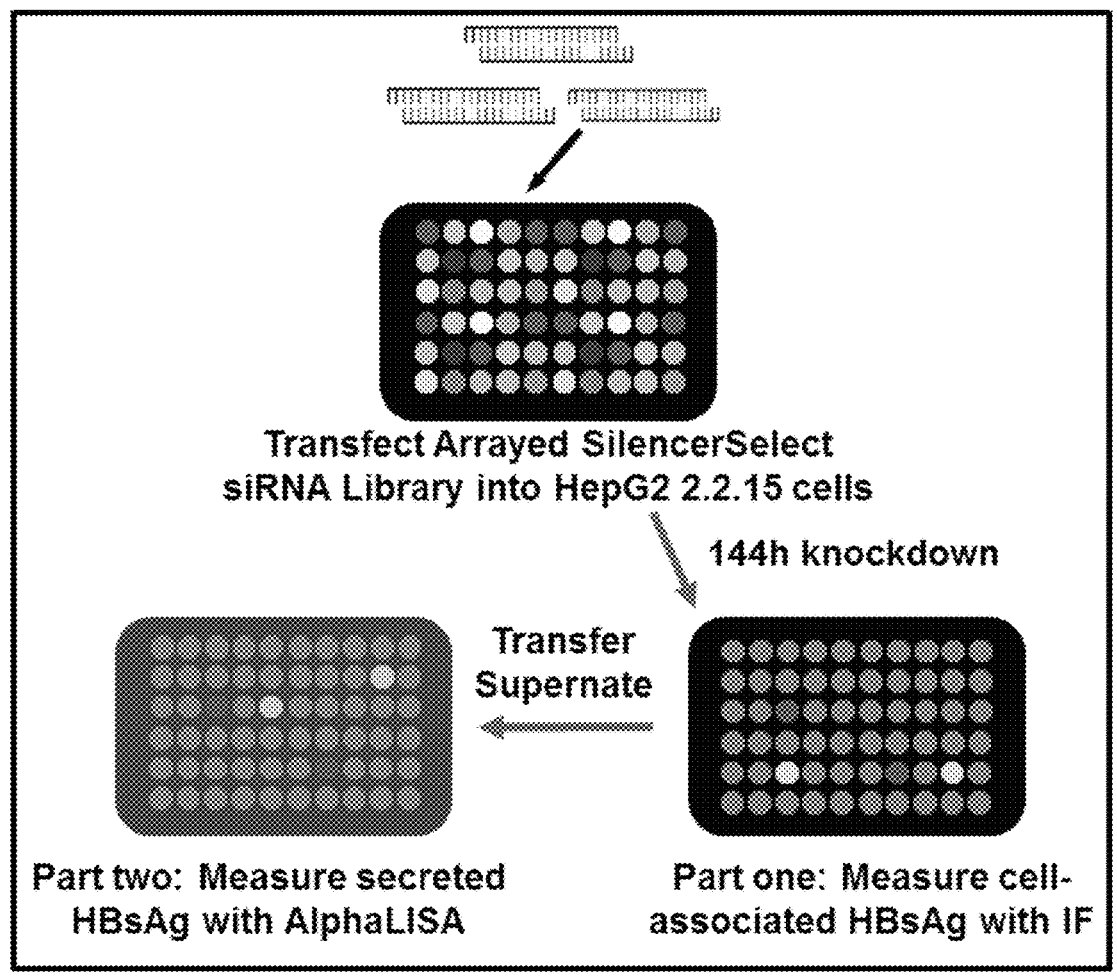
FIG. 6 is a schematic illustration of a two-part RNAi screen developed to find host factors that modulate the levels of cell-associated and secreted HBsAg.

A two-part RNAi screen was developed to find host factors that modulate the levels of cell-associated and secreted HBsAg (FIG. 6). For the screen HepG2 2.2.15 cells were chosen because they contain integrated HBV genomic DNA and constitutively express HBV mRNAs and package and secrete infectious HBV (Sells, M. A., M. L. Chen, and G. Acs, *Production of hepatitis B virus particles in Hep G2 cells transfected with cloned hepatitis B virus DNA*. Proceedings of the National Academy of Sciences, 1987. 84(4): p. 1005-1009). Therefore host factors required for these viral processes could be discovered using a siRNA screen. We optimized the screening assay using a negative control (NT) siRNA and a positive control siRNA (siHBV2), which targets a region common to all HBV transcripts. We used this assay to screen in triplicate a whole-genome siRNA library, Ambion Silencer Select (21,584 genes targeted by three siRNAs per gene screened as a pool. The screen was done by reverse transfecting the siRNAs at 50 nM final concentration into the HepG2 2.2.15 cells. After 144 h of siRNA-mediated knockdown the supernatant was removed and the siRNA-transfected cells were fixed, permeabilized, and immunostained for HBsAg expression and for nuclear DNA. The processed plates were then imaged on a scanning microscope and analyzed for percent infection and cell number using analysis software (part one). The supernatant from each well was then assayed in a well-by-well manner using a plate reader-based assay that detects HBsAg (part two). Part one of the screen was designed to detect HBV-HFs required for HBsAg transcription and translation, and part two also detected factors required for HBsAg+ HBV virion formation and budding. Pools were selected as hits if they altered HBsAg staining or levels in the supernatant to less than 50%, or greater than 200%, of the plate mean. siRNA pools which decreased cell number to 40% or less than the plate mean were removed from further consideration. Pools that scored in the primary screen then had their component siRNAs retested individually in the validation round.

We carried out the validation screening for all candidates from the entire screen (all 80 plates); these efforts identified multiple previously unrecognized high confidence candidate HBV-HFs. We selected high priority candidates from the second set of candidates and performed mechanistic investigations. Factors identified in the screen included ZCCHC14 and YWHAH.

Example 2. Validation of ZCCHC14 as an HBV Host Factor

To confirm that ZCCHC14 is an HBV host factor, the effects of targeting ZCCHC14 on levels of HBsAg, a surface antigen of HBV that indicates current infection, were evaluated.

Figure 2:
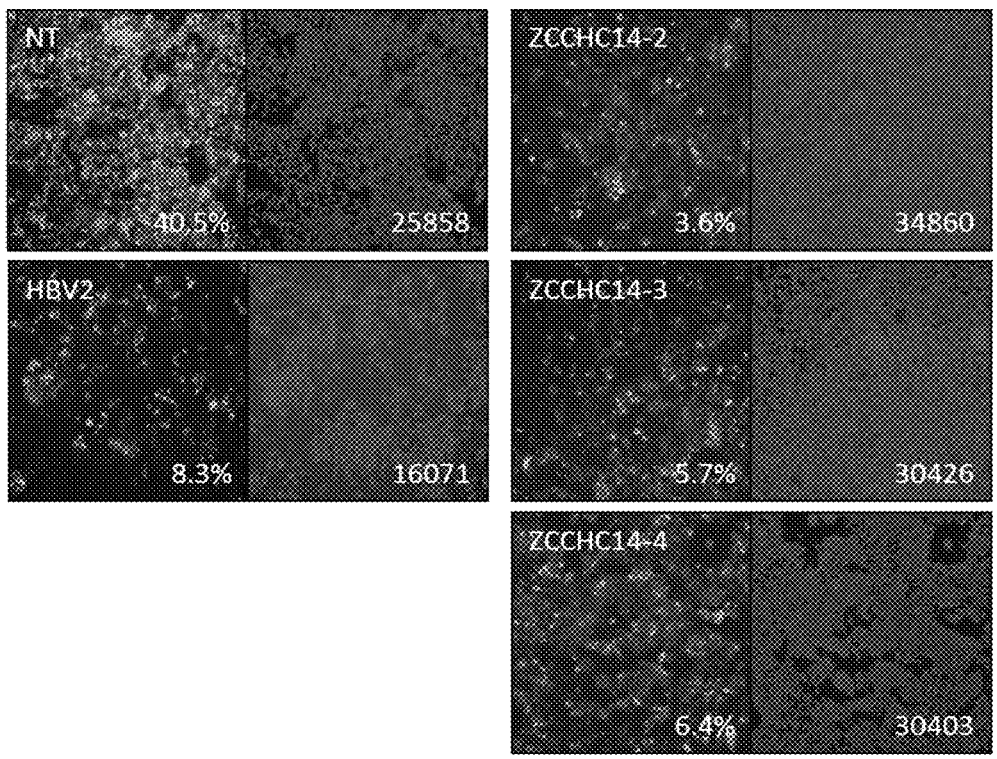
FIG. 2 is a set of five pairs of images of HepG2 2.2.15 cells transfected with a non-targeting siRNA (siNT), one against HBV, or one of three specific for ZCCHC14. At six days post-transfection, the cells were fixed and stained with antibodies against HBsAg (H25B10, green) and stained with DAPI (blue) to show host cell nuclei. Numbers shown indicate the percentage of cells staining positive for HBsAg and the total number of cells present.

HepG2 2.2.15 cells were transfected with a non-targeting siRNA (siNT), one against HBV, or one of three specific for ZCCHC14 (Ambion siRNAs 23202, 23203, or 23204). At six days post-transfection, the cells were fixed and stained with an antibody against HBsAg (H25B10, green), as a measure of HBV replication, and DAPI (blue) and examined by immunofluorescence. Data from two separate experiments is shown in FIG. 1, which demonstrates that depletion of ZCCHC14 substantially reduced HBsAg staining. As shown in FIG. 2, the percentage of cells staining positive for HBsAg (green) was greatly decreased by siRNA targeting, without significantly affecting the total number of cells present. This demonstrated that suppression of ZCCHC14 substantially reduced HBsAg expression.

Figure 3:
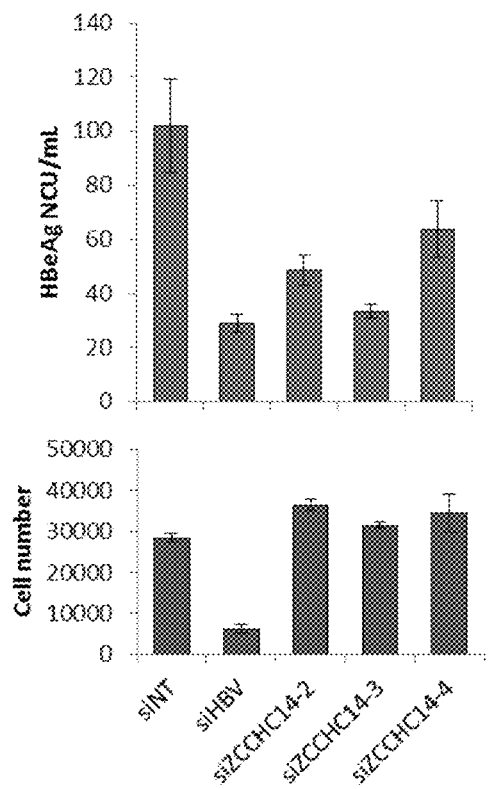
FIG. 3 is a pair of graphs showing that lowering ZCCHC14 levels reduces production of HBV e antigen (HBeAg). HepG2 2.2.15 cells were transfected with a non-targeting siRNA (siNT), one against HBV, or one of three specific for ZCCHC14.

The HBeAg is the extracellular form of the HBV c antigen (HBcAg), and is a marker of active viral replication. To determine what effect lowering ZCCHC14 levels would have on production of HBeAg, HepG2 2.2.15 cells were transfected with a non-targeting siRNA (siNT), one against HBV, or one of three specific for ZCCHC14. At six days post-transfection, the amount of HBeAg secreted by cells was determined by ELISA (AutoBio, CL0312-2). As shown in FIG. 3, lowering ZCCHC14 levels significantly reduced production of HBeAg.

Figure 4:
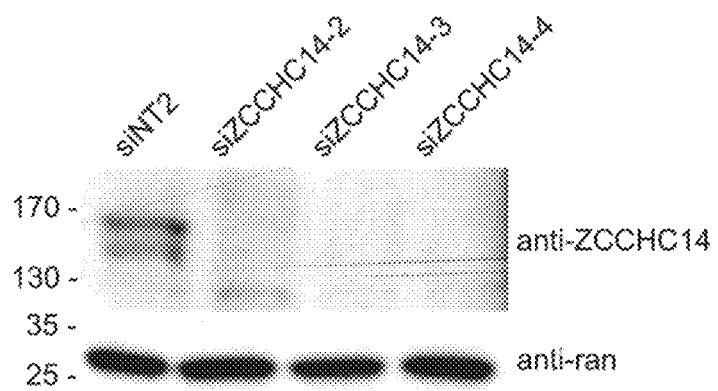
FIG. 4 is an image of an immunoblot for ZCCHC14 (Bethyl, A303-096A) or RAN (Sigma, anti-RAN1, loading control) in HepG2 2.2.15 cells were transfected with the non-targeting siRNA or siRNAs against ZCCHC14.

To show that the siRNAs against ZCCHC14 were reducing levels of ZCCHC14 protein, HepG2 2.2.15 cells were transfected with the non-targeting siRNA or siRNAs against ZCCHC14. At six days post-transfection, cells were lysed into Laemmli buffer, resolved by SDS-PAGE, and analyzed by immunoblot for ZCCHC14 (Bethyl, A303-096A) or ran (Sigma, RAN), as a loading control. As shown in FIG. 4, the siRNAs against ZCCHC14 induced a loss of ZCCHC14 protein to undetectable levels.

Figure 5:
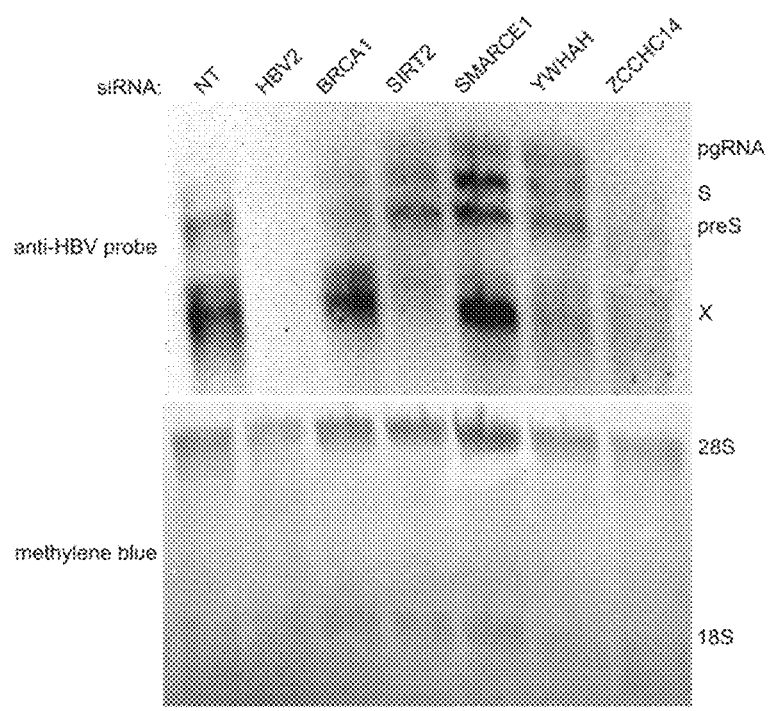
FIG. 5 is an image of a Northern blot showing that depletion of ZCCHC14 with siRNA markedly reduced levels of all HBV transcripts.

Finally, to determine what effect depletion of ZCCHC14 using siRNA would have on levels of all HBV transcripts, HepG2 2.2.15 cells were transfected with siRNAs as indicated above. At six days post transfection, total RNA was isolated from cells (RNeasy Plus, Qiagen) and 5 µg of RNA from each sample was resolved on a 1.2% agarose/2.2 M formaldehyde/MOPS gel. RNAs were transferred to a Hybond N+ membrane (GE Healthcare) by standard northern blotting. The membrane was then stained with methylene blue to detect 28S and 18S RNAs (used as loading controls) and subsequently probed with a digoxigenin-labeled oligonucleotide probe against HBV (DIG High Prime, Roche) to detect HBV mRNAs. The four distinct forms of HBV mRNA as labeled at right (pgRNA, S, preS and X). As shown in FIG. 5, depletion of ZCCHC14 using siRNA markedly reduced levels of all HBV transcripts.

Figure 8A:
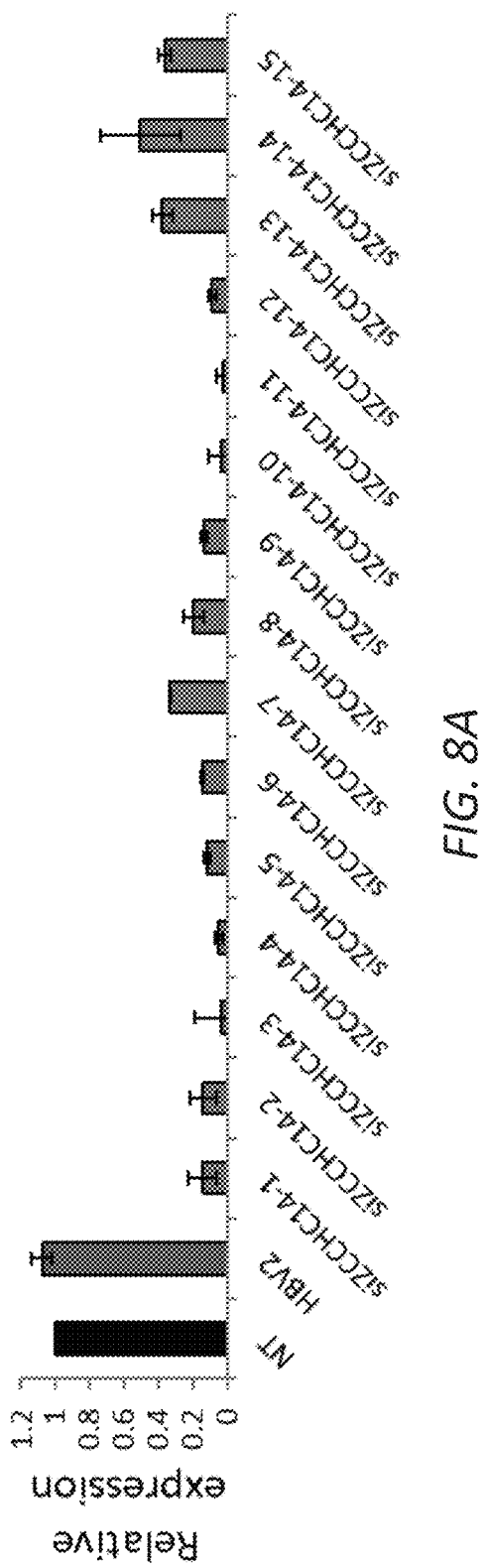
FIG. 8A is a graph showing levels of mRNA isolated from cells; qPCR was performed to assess the abundance of ZCCHC14 mRNA. Values indicate the mean of expression of two independent experiments±SD.
Figure 8B:
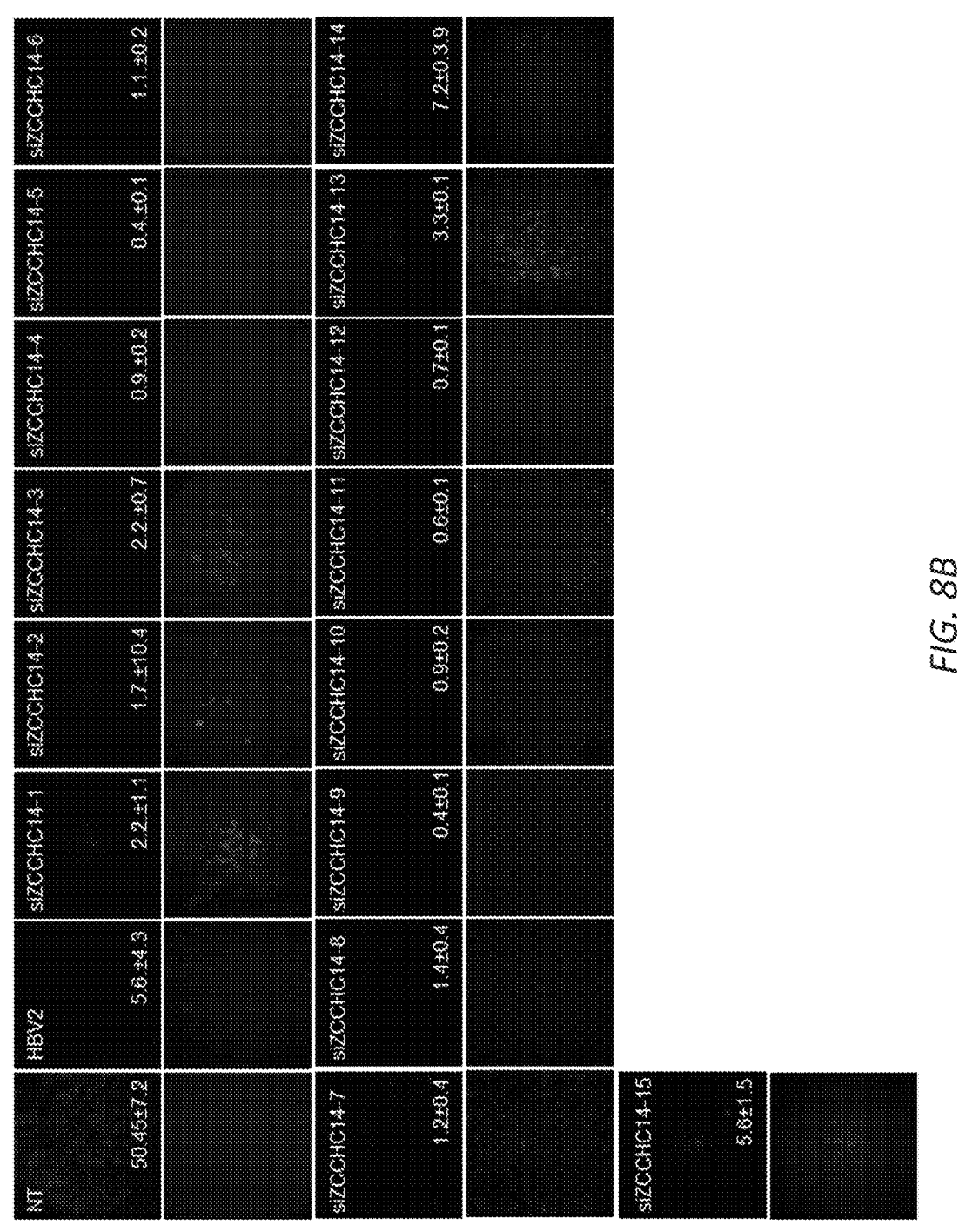
Figure 8C:
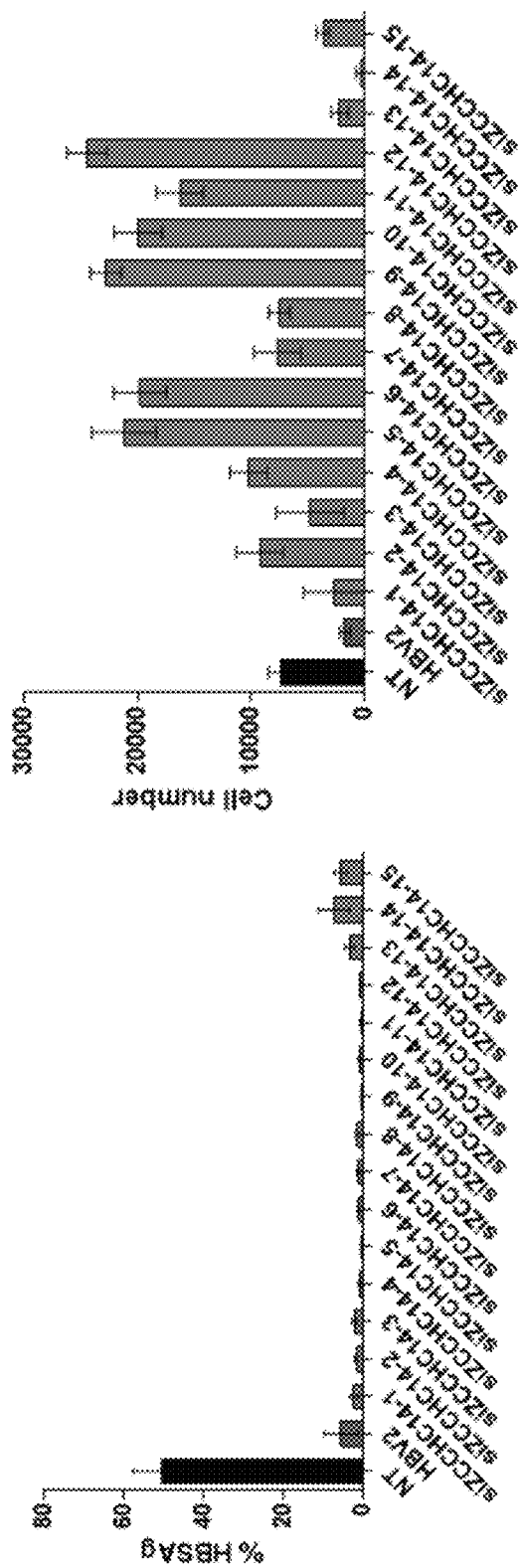
FIG. 8C is a pair of graphs showing quantitation of the experiments in FIG. 8B, indicating the percentage of HBsAg expressing cells or the cell number±SD.

HepG2.2.15 cells were transfected with 15 additional siRNAs targeting the coding sequence of ZCCHC14. At six days post-transfection, mRNA was isolated from cells and qPCR was performed to assess the abundance of ZCCHC14 mRNA. The results are shown in graph form in FIG. 8A. The cells were also fixed, permeabilized and stained for HBsAg and nuclei, and image analysis software was used to determine the percentage of HBsAg expressing cells and the cell number. The results are shown in FIGS. 8B-C. Interestingly, although all of the siRNAs were able to knock down levels of ZCCHC14 mRNA, they had differing effects on cell viability.

Example 3. Validation of YWHAH as an HBV Host Factor

Figure 7A:
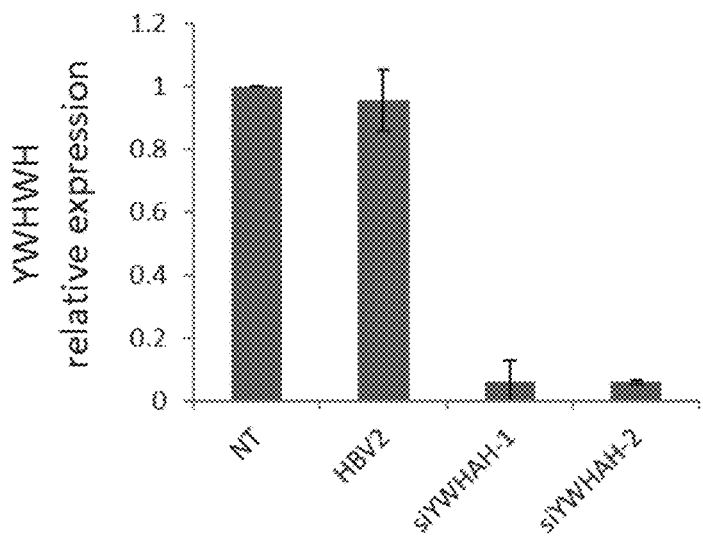
FIG. 7A is a graph of relative expression levels of mRNA isolated from cells transfected with the indicated siRNAs targeting the coding sequence of YWHAH for 120 h. NT=negative control non-targeting siRNA. Values represent the mean of expression of two independent experiments±SD. (B) Cells were fixed, permeabilized and stained for HBsAg (green) and nuclei (blue). Image analysis software was used to determine the percentage of HBsAg expressing cells and the cell number. Quantitation is shown below and indicates the percentage of HBsAg expressing cells or cell number±SD. Representative images of two independent experiments are provided.
Figure 7B:
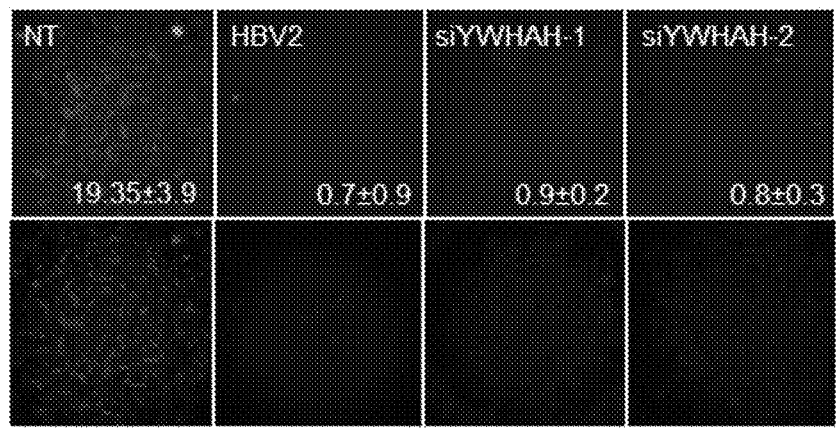
FIG. 7B is a set of images of cells from FIG. 7A that were fixed, permeabilized and stained for HBsAg (green) and nuclei (blue). Image analysis software was used to determine the percentage of HBsAg expressing cells and the cell number. Quantitation is shown in the graphs below and indicates the percentage of HBsAg expressing cells or cell number±SD. Representative images of two independent experiments are provided.
Figure 7B:
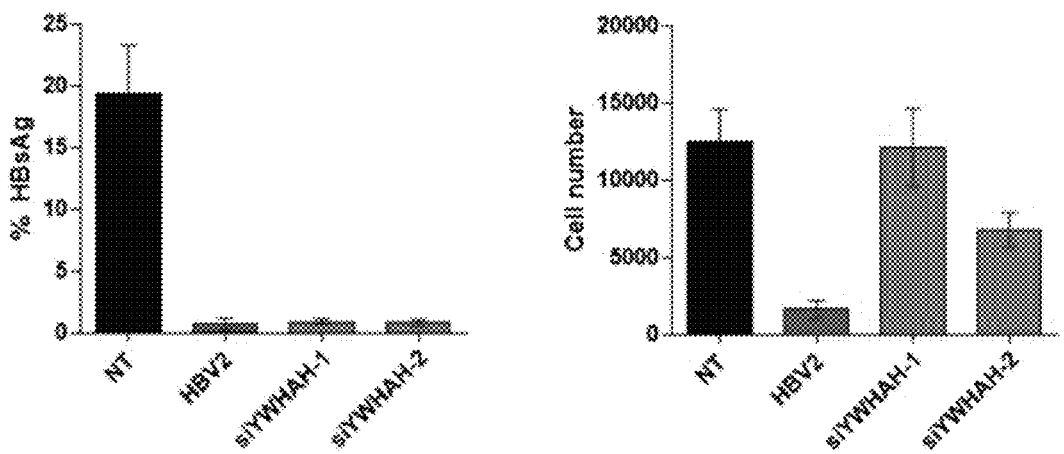

To confirm that YWHAH is an HBV host factor, the effects of targeting YWHAH on levels of HBsAg, a surface antigen of HBV that indicates current infection, were evaluated. To this end HepG2.2.15 cells, which are constitutively infected with HBV and thus express Hepatitis B surface antigen (HBsAg), were transfected with two siRNAs targeting the coding sequence of YWHAH. At six days post-transfection, mRNA was isolated from cells and qPCR was performed to assess the abundance of YWHAH mRNA after transfection with the indicated siRNAs. The results, shown in FIG. 7A, show a decrease in YWHAH mRNA as compared to HBV2.

The cells were also fixed, permeabilized and stained for HBsAg (green) and nuclei (blue). Image analysis software was used to determine the percentage of HBsAg expressing cells and the cell number. Quantitation is shown below and indicates the percentage of HBsAg expressing cells or cell number±SD. Representative images of two independent experiments are provided. These studies demonstrate that depletion of YWHAH produces a decrease in the levels of HBsAg in the siRNA transfected cells and confirms that YWHAH is important for HBsAg expression in the HepG2.2.15 cells.

Figure 9A:
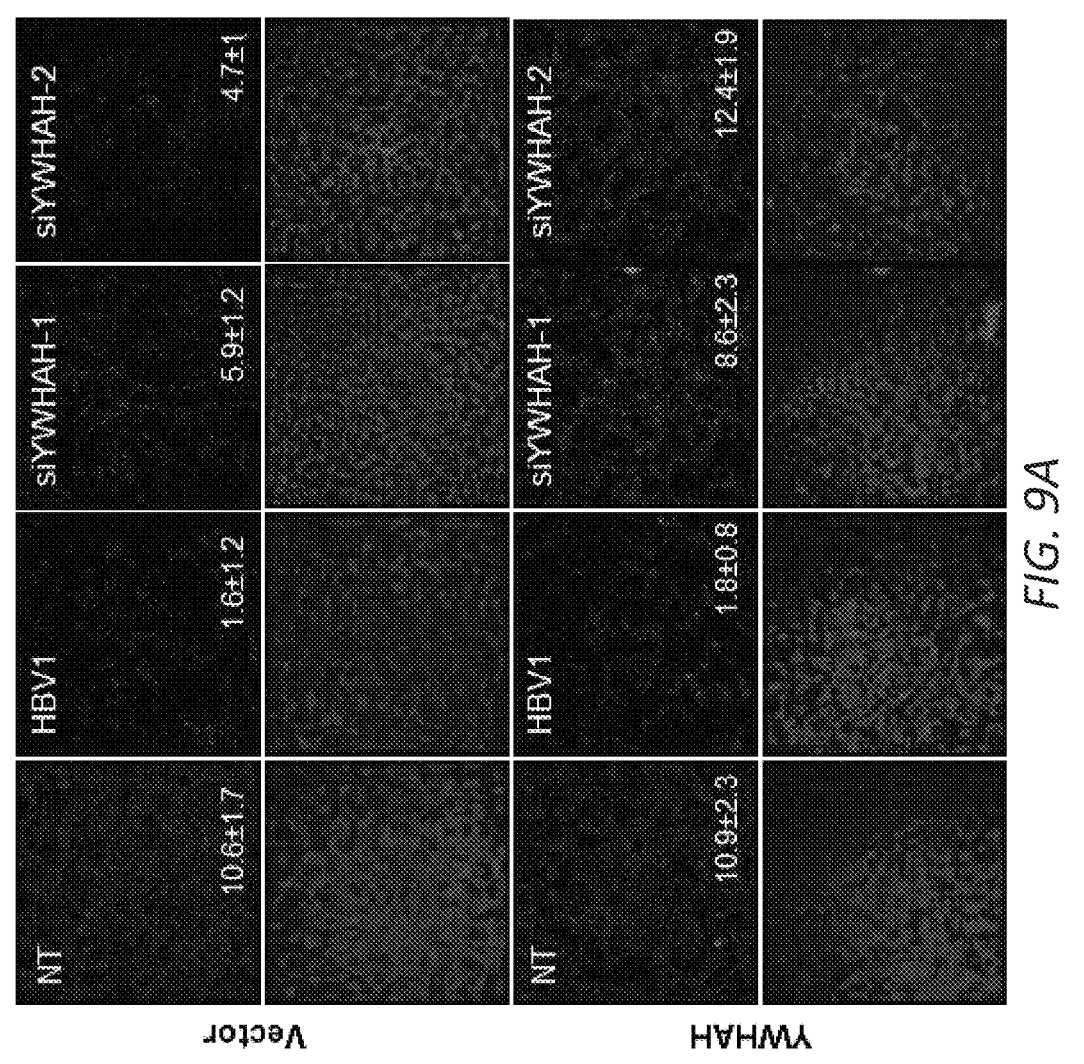
Figures 9B, 9C:
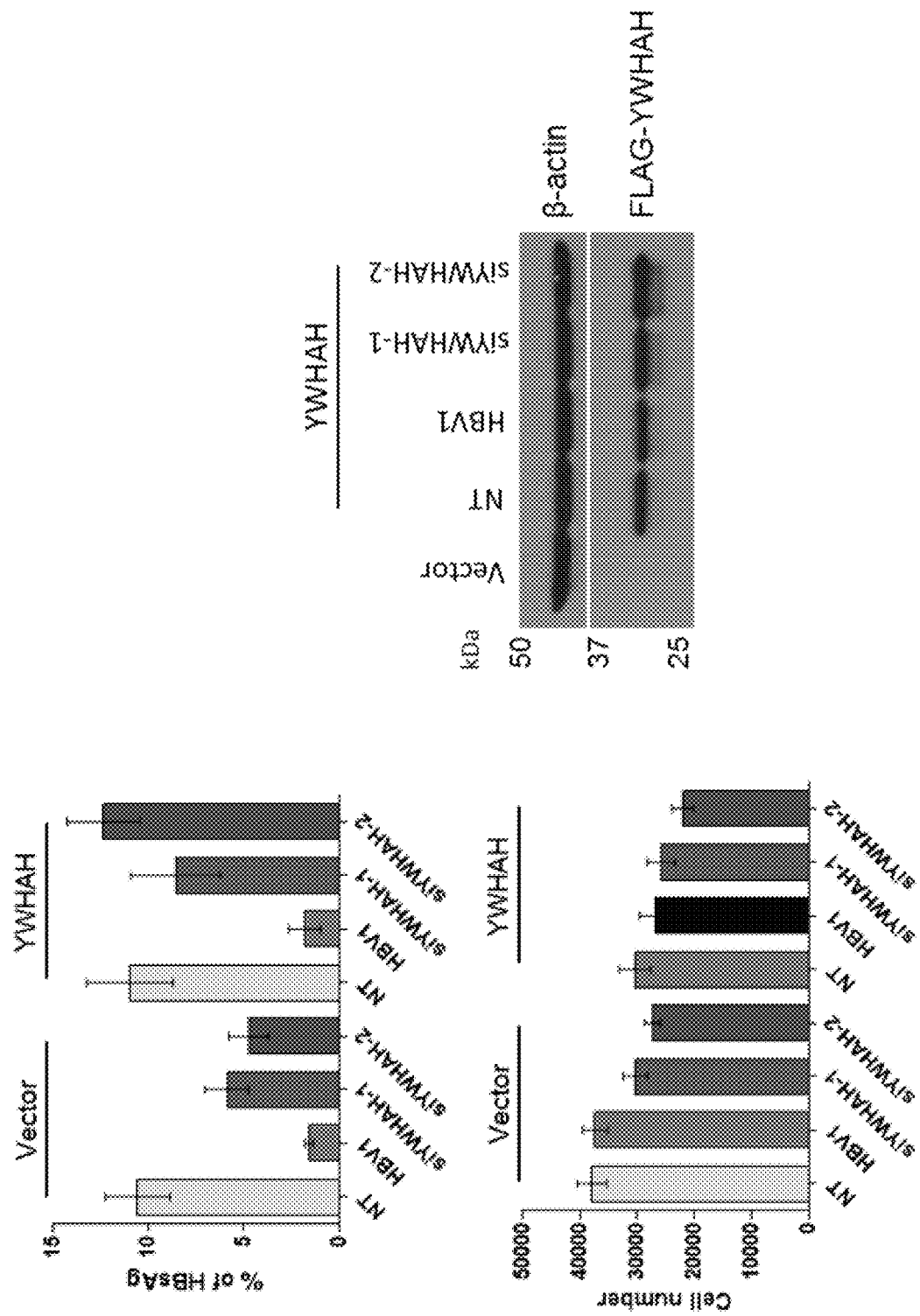
FIG. 9B is a graph showing quantitation of experiments in FIG. 9A. The percentage HBsAg expressing cells and the cell number are provided in the right panels and expressed as mean±SD.
FIG. 9C shows immunoblots of whole cell lysates from the HepG2-NTCP cells stably transduced with FLAG-YWHAH and transfected for 72 h with the indicated siRNAs (NT, HBV1 or two siRNAs (siYWHAH-1, siYWHAH-2) targeting the coding sequence of YWHAH) shown in panel A. YWHAH expression was determined using an anti-FLAG antibody. β-actin levels are shown as a loading control. kDa=kilodaltons.

To further validate the role of YWHAH in HBV replication, HepG2-NTCP cells which were stably transduced with retrovirus expressing either the empty vector negative control (Vector) or an siRNA resistant FLAG-tagged-YWHAH (YWHAH) were transfected either with non-targeting negative control siRNA (NT), a siRNA that targets a region shared among the HBV transcripts (HBV1) or either of two independent siRNAs (siYWHAH-1, siYWHAH-2) targeting the coding sequence of YWHAH. 72 h post transfection, the cells were infected with HBV. 7 days post infection the cells where stained for DNA (blue) and immunostained with an anti-HBsAg antibody (green). The results are shown in FIG. 9A. The quantitation of the percentage HBsAg expressing cells and the cell number are provided in FIG. 9B. These studies demonstrate that depletion of YWHAH produces a decrease in the levels of HBsAg in the siRNA transfected Vector cells but not in the cells that express a siRNA-resistant version of YWHAH and confirms that YWHAH is important for HBsAg expression in a fully infectious HBV assay using NTCP expressing human cells.

Immunoblots of whole cell lysates from the HepG2-NTCP cells stably transduced with siRNA resistant FLAG-YWHAH and transfected for 72 h with the indicated siRNAs (NT, HBV1 or two siRNAs (siYWHAH-1, siYWHAH-2) targeting the coding sequence of YWHAH) shown in panel A. YWHAH expression was determined using an anti-FLAG antibody. The results are shown in FIG. 9C.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising inhibitory nucleic acids targeting zinc finger, CCHC domain containing 14 (ZCCHC14) mRNA and inhibitory nucleic acids targeting Tyrosine 3-Monooxygenase/Tryptophan 5-Monooxygenase Activation Protein, Eta Isoform (YWHAH) mRNA, wherein the inhibitory nucleic acids comprise one or more modified bonds or nucleotides.

2. The composition of claim 1, wherein the inhibitory nucleic acids are selected from the group consisting of an antisense oligonucleotide; short interfering RNA (siRNA); and a short, hairpin RNA (shRNA).

3. The composition of claim 1, wherein the inhibitory nucleic acids targeting ZCCHC14 targets a ZCCHC14 mRNA comprising SEQ ID NO:1.

4. The composition of claim 3, wherein the inhibitory nucleic acids targeting ZCCHC14 targets are complementary to at least 8 consecutive nucleotides of SEQ ID NO:1.

5. The composition of claim 1, wherein the inhibitory nucleic acids targeting YWHAH targets a YWHAH mRNA comprising SEQ ID NO:6.

6. The composition of claim 5, wherein the inhibitory nucleic acids targeting YWHAH are complementary to at least 8 consecutive nucleotides of SEQ ID NO:6.

7. The composition of claim 1, wherein the inhibitory nucleic acids are each 8 to 30 nucleotides in length.

8. The composition of claim 1, wherein at least one nucleotide of the inhibitory nucleic acids is a nucleotide analogue or a 2' O-methyl.

9. The composition of claim 1, wherein the inhibitory nucleic acids comprise at least one ribonucleotide, at least one deoxyribonucleotide, or at least one bridged nucleotide.

10. The composition of claim 9, wherein the bridged nucleotide is a LNA nucleotide, a cEt nucleotide or a ENA modified nucleotide.

11. The composition of claim 1, wherein one or more of the nucleotides of the inhibitory nucleic acids comprise 2'-fluoro-deoxyribonucleotides, one or more of the nucleotides comprise 2'-O-methyl nucleotides, one or more of the nucleotides comprise ENA nucleotide analogues, and/or one or more of the nucleotides comprise LNA nucleotides.

12. The composition of claim 1, wherein the nucleotides of the inhibitory nucleic acids comprise phosphorothioate internucleotide linkages between at least two nucleotides or between all nucleotides.

* * * * *